(12) United States Patent
Iliff

(10) Patent No.: US 6,817,980 B2
(45) Date of Patent: *Nov. 16, 2004

(54) AUTOMATED DIAGNOSTIC SYSTEM AND METHOD INCLUDING DISEASE TIMELINE

(75) Inventor: Edwin C. Iliff, La Jolla, CA (US)

(73) Assignee: First Opinion Corporation, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/446,339

(22) Filed: May 27, 2003

(65) Prior Publication Data

US 2003/0199740 A1 Oct. 23, 2003

Related U.S. Application Data

(63) Continuation of application No. 09/785,046, filed on Feb. 14, 2001, now Pat. No. 6,569,093.
(60) Provisional application No. 60/182,176, filed on Feb. 14, 2000.

(51) Int. Cl.[7] .................................................. A61B 5/00
(52) U.S. Cl. ........................................ 600/300; 128/920
(58) Field of Search ................................ 600/300–301; 702/19; 705/1–4; 379/106.1; 128/920–925, 897–898; 235/375; 706/924

(56) References Cited

U.S. PATENT DOCUMENTS

| | | | |
|---|---|---|---|
| 5,255,187 A | * 10/1993 | Sorensen | .................... 600/300 |
| 5,594,638 A | 1/1997 | Iliff | |
| 5,660,176 A | 8/1997 | Iliff | |
| 5,711,297 A | 1/1998 | Iliff | |
| 5,724,968 A | 3/1998 | Iliff | |
| 5,794,208 A | 8/1998 | Goltra | |
| 5,802,495 A | 9/1998 | Goltra | |
| 5,812,984 A | 9/1998 | Goltra | |
| 5,823,949 A | * 10/1998 | Goltra | ........................ 600/300 |
| 5,868,669 A | 2/1999 | Iliff | |
| 5,910,107 A | 6/1999 | Iliff | |
| 5,935,060 A | 8/1999 | Iliff | |
| 5,974,389 A | * 10/1999 | Clark et al. | ..................... 705/3 |
| 6,022,315 A | 2/2000 | Iliff | |
| 6,071,236 A | 6/2000 | Iliff | |
| 6,113,540 A | 9/2000 | Iliff | |
| 6,206,829 B1 | 3/2001 | Iliff | |
| 6,234,964 B1 | 5/2001 | Iliff | |
| 6,246,975 B1 * | 6/2001 | Rivonelli et al. | ........... 128/920 |
| 6,270,456 B1 | 8/2001 | Iliff | |

\* cited by examiner

Primary Examiner—Charles Marmor
Assistant Examiner—Michael Astorino
(74) Attorney, Agent, or Firm—Knobbe Martens Olson & Bear LLP

(57) ABSTRACT

Structure-based processing includes a method of diagnosing diseases that works by arranging diseases, symptoms, and questions into a set of related disease, symptom, and question structures, such as objects or lists, in such a way that the structures can be processed to generate a dialogue with a patient. A structure-based processing system organizes medical knowledge into formal structures and then executes those structures on a structure engine to automatically select the next question. Patient responses to the questions lead to more questions and ultimately to a diagnosis. An object-oriented embodiment includes software objects utilized as active, intelligent agents where each object performs its own tasks and calls upon other objects to perform their tasks at the appropriate time to arrive at a diagnosis. Alternative symptoms, synergies, encoding of patient responses, multiple diagnostic modes, disease profiles or timelines, and the reuse of diagnostic objects enhance the processing of the system and method.

9 Claims, 37 Drawing Sheets

2700

| | COMMON MIGRAINE | | CLASSIC MIGRAINE | | CLUSTER HEADACHE | | SUBARACHNOID HEMORRHAGE | |
|---|---|---|---|---|---|---|---|---|
| HEADACHE DISEASE SYMPTOM MATRIX (DSM) SHOWING TWO COLUMN SCORING, SYNERGIES, AND HAI vs. VAI | | | | | | | | |
| CONSULTATION BEGINS IN HAI AND ASKS QUESTIONS HORIZONTALLY, I.E., ACROSS THE ARRAY | | | | | | | | |
| HAI MODE .........>>> HISTORY OF THE PRESENT ILLNESS (NOTE: IN HAI, SOME ACTUAL, SOME ALTERNATIVE) | Actual | Alternative | Actual | Alternative | Actual | Alternative | Actual | Alternative |
| Throbbing pain? | 30 | | | 25 | -20 | | -30 | |
| Nausea 1? | | 20 | 35 | | | -20 | 40 | |
| Nausea 2? | 35 | | 30 | | | -20 | 35 | |
| Nausea 3? | 40 | | | | 35 | -40 | | 50 |
| Vomiting? | | 30 | | 40 | -20 | | | 25 |
| Unilateral? | 30 | | 30 | | 40 | | -20 | |
| Prodromal? | -40 | | | 50 | -30 | | -30 | |
| Aura with visual changes? | 10 | | 30 | | -30 | | -25 | |
| If you have an aura, is the headache on the opposite side? | | 10 | | 30 | 0 | | 0 | |
| Photo phobia? | | 25 | 30 | | -10 | | 40 | |
| Horner's syndrome? | 0 | | 0 | | 50 | | -20 | |
| Recurrent up to once a month? | 20 | | | 20 | 20 | | -20 | |
| Recurrent in clusters? | 0 | | 0 | | 50 | | -30 | |
| AT THIS POINT, THE DSM MAY SEE THAT THE SCORE FOR CLASSIC MIGRAINE IS RAPIDLY ACCUMULATING AND THE SYSTEM WILL START ASKING QUESTIONS DOWN THE "ACTUAL" COLUMN FOR CLASSIC MIGRAINE | | | | | | | | |
| VAI MODE VVVVVVVVVVVVVVVVV | | | | | | | | |
| Family history of migraine? | | 30 | 40 | | 0 | | | 0 |
| Feel "sick" afterwards? | 40 | | 45 | | | -10 | | 0 |
| Treated successfully with ergot? | | 20 | 40 | | 20 | | | 0 |
| (NOTE: IN VIA ALL CLASSIC MIGRAINE QUESTIONS ARE ACTUAL) | | | | | | | | |
| THE PATIENT COULD BE GIVEN THE CHOICE HERE OF GOING BACK AND RE-ANSWERING ALL OF THE QUESTIONS ABOUT CLASSIC MIGRAINE SUBSTITUTING THE "ACTUAL" LANGUAGE FOR THE ALTERNATIVE LANGUAGE. THIS IS NOT RECOMMENDED BUT IN THIS WAY, NO MATTER WHAT DISEASE THE PATIENT HAS, IF IT COVERED, THE PATIENT WILL INTERACT WITH A DIALOG CREATED BY A WORLD CLASS EXPERT. | | | | | | | | |
| THE SYNERGY WEIGHTS ARE ADDED BELOW (NOT SHOWN) | | | | | | | | |
| Simultaneous Synergies | | | | | | | | |
| Sequencing Synergies | | | | | | | | |
| Onset - Offset Analysis | | | | | | | | |
| Summation Synergies | | | | | | | | |
| | Actual | Alternative | Actual | Alternative | Actual | Alternative | Actual | Alternative |
| DIAGNOSTIC SCORE OF BOTH COLUMNS .........> | 165 | 135 | 280 | 200 | 50 | -70 | -60 | 75 |
| | COMMON MIGR | | CLASSIC MIGR | | CLUSTER | | SUBARACHNOID HEM | |
| DIAGNOSTIC SCORE TOTAL .........> | 300 | | 480 | | -20 | | 15 | |
| | | | THE DIAGNOSIS | | | | | |
| DSMhai3.xls | | | | | | | | |

This page demonstrates a type of question that lets the patient specify visually when a given set of symptoms occurred. The indicated Onset/Offset times are captured and used to adjust the diagnostic scores.

2810  Time (hours) after First Significant Symptom 0  1  2  3  4  5  6  7  8  9  10

2812 — ANOREXIA
2814 — NAUSEA
2816 — EPIG PAIN
2818 — RLQ PAIN 0  1  2  3  4  5  6  7  8  9  10

Use the mouse to slide symptoms left and right to indicate when they occurred

SUBMIT — 2820

FIG. 28

AUTOMATED DIAGNOSTIC SYSTEM AND METHOD INCLUDING DISEASE TIMELINE

PRIORITY

This application is a continuation of U.S. application Ser. No. 09/785,046, filed Feb. 14, 2001, now U.S. Pat No. 6,569,093 entitled AUTOMATED DIAGNOSTIC SYSTEM AND METHOD INCLUDING DISEASE TIMELINE. The benefit under 35 U.S.C. §119(e) of U.S. provisional Application No. 60/182,176, filed Feb. 14, 2000, entitled "AUTOMATED DIAGNOSTIC SYSTEM AND METHOD" is hereby claimed.

RELATED APPLICATIONS

The subject matter of U.S. patent applications: application Ser. No. 09/785,037, filed Feb. 14, 2001 and entitled "AUTOMATED DIAGNOSTIC SYSTEM AND METHOD INCLUDING SYNERGIES", now issued as U.S. Pat. No. 6,468,210; application Ser. No. 09/785,045, filed Feb. 14, 2001 and entitled "AUTOMATED DIAGNOSTIC SYSTEM AND METHOD INCLUDING ENCODING PATIENT DATA", now issued as U.S. Pat. No. 6,475,143; application Ser. No. 09/785,043, filed Feb. 14, 2001 and entitled "AUTOMATED DIAGNOSTIC SYSTEM AND METHOD INCLUDING MULTIPLE DIAGNOSTIC MODES", now issued as U.S. Pat. No. 6,524,241; application Ser. No. 09/785,047, filed Feb. 14, 2001 and entitled "AUTOMATED DIAGNOSTIC SYSTEM AND METHOD INCLUDING ALTERNATIVE SYSTEMS", now issued as U.S. Pat. No. 6,527,713; and application Ser. No. 09/785,044, filed Feb. 14, 2001 and entitled "AUTOMATED DIAGNOSTIC SYSTEM AND METHOD INCLUDING REUSE OF DIAGNOSTIC OBJECTS" are related to this application.

BACKGROUND OF THE INVENTION

1. Field of the Invention

The field of the invention relates to computerized medical diagnostic systems. More particularly, embodiments of the present invention relate to a computerized system for time-based diagnosis of a patient's medical complaint by use of dynamic data structures.

2. Description of the Related Technology

Health care costs currently represent a significant portion of the United States Gross National Product and are generally rising faster than any other component of the Consumer Price Index. Moreover, usually because of an inability to pay for medical services, many people are deprived of access to even the most basic medical care and information.

Many people delay in obtaining, or are prevented from seeking, medical attention because of cost, time constraints, or inconvenience. If the public had universal, unrestricted, and easy access to medical information, many diseases could be prevented. Likewise, the early detection and treatment of numerous diseases could keep many patients from reaching the advanced stages of illness, the treatment of which is a significant part of the financial burden attributed to our nation's health care system. It is clear that the United States is facing health-related issues of enormous proportions and that present solutions are not robust.

Previous attempts at tackling the healthcare problem have involved various forms of automation. Some of these attempts have been in the form of a dial-in library of answers to medical questions. Other attempts have targeted providing doctors with computerized aids for use during a patient examination. These methods involve static procedures or algorithms. What is desired is an automated way of providing to a patient medical advice and diagnosis that is quick, efficient and accurate. Such a medical advice system should be modular to allow expansion for new types of medical problems or methods of detection.

SUMMARY OF THE INVENTION

Structure-based processing is a method of diagnosing diseases that works by arranging diseases, symptoms, and questions into a set of related disease, symptom, and question structures, such as objects or lists, in such a way that the structures can be processed to generate a dialogue with a patient. Each question to the patient generates one of a set of defined responses, and each response generates one of a set of defined questions. This establishes a dialogue that elicits symptoms from the patient. The symptoms are processed and weighted to rule diseases in or out. The set of ruled-in diseases establishes the diagnosis. A structure-based processing system organizes medical knowledge into formal structures and then executes those structures on a structure engine, such as a list-based engine, to automatically select the next question. The responses to the questions lead to more questions and ultimately to a diagnosis.

In one aspect of the present invention there is a method of automatically diagnosing a medical condition by use of a predicted timeline of symptoms, the method comprising accessing a plurality of timelines which are each representative of a typical pattern of a disease, automatically asking one or more questions of a patient so as to elicit a chief complaint, automatically receiving answers from the patient in response to the questions, automatically identifying a disease corresponding to the chief complaint, correlating the chief complaint to a timeline for the disease, automatically asking one or more questions to elicit the onset time of a symptom on the timeline for the disease, adding an incremental weight to a cumulative score for the disease if the symptom is established, and establishing the diagnosis when the cumulative score exceeds a predetermined threshold.

In another aspect of the present invention there is a method of automatically diagnosing a medical condition of a patient by use of a predicted timeline of symptoms, the method comprising generating a plurality of timelines which are each representative of a typical course of a disease via a characteristic pattern of symptom attributes over time, and automatically selecting a particular disease based on a pattern of symptom attributes associated with a patient being similar to the timeline associated with the particular disease.

BRIEF DESCRIPTION OF THE DRAWINGS

FIG. 27 is a diagram of an exemplary disease-symptom matrix.

FIG. 28 is a diagram of an exemplary generic disease timeline.

FIG. 32b is a flowchart of a mode switching feature using the symptom elements of FIG. 32a.

DETAILED DESCRIPTION

Figure 1:
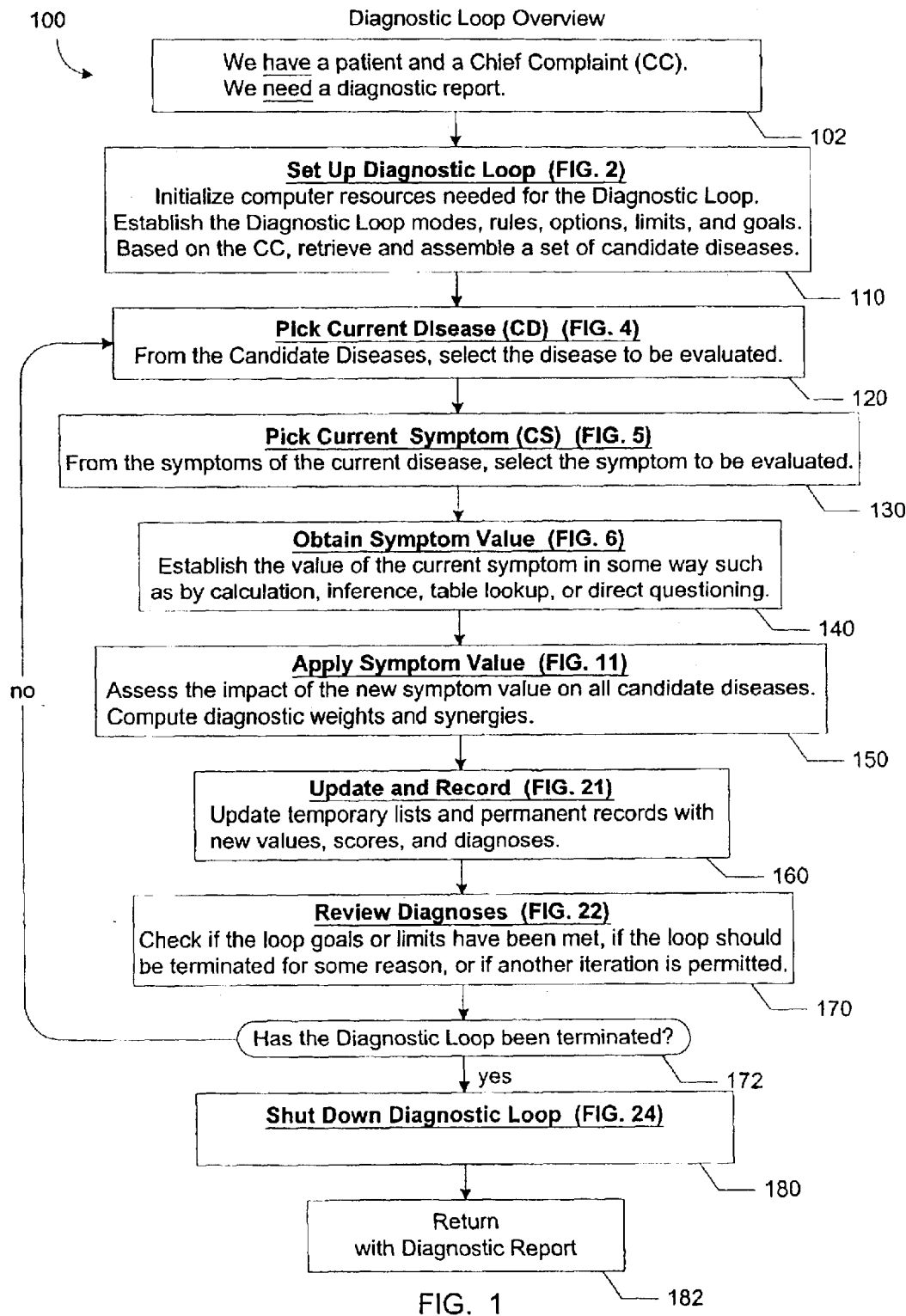
FIG. 1 is a flowchart of one embodiment of a diagnostic loop performed by a structure-based engine of a medical diagnostic and treatment advice system.

The following detailed description presents a description of certain specific embodiments of the present invention. However, the present invention may be embodied in a multitude of different ways as defined and covered by the claims. In this description, reference is made to the drawings wherein like parts are designated with like numerals throughout.

The detailed description will begin with an overview of the specific embodiments followed by a description of each of the drawings. The overview is partitioned into the following sections: Terminology, Object-based Medical Diagnosis, Object-based Method, Disease Object, Symptom Object, Valuator Object, Question Object, Node Object, List-based Engine Concepts, Dynamic Rules and Goals, Dynamic Momentum, Horizontal Axis of Inquiry (HAI), Vertical Axis of Inquiry (VAI), Alternative Symptoms, Disease Timeline, Spectrum of Terms/PQRST Code, and Synergy.

I. Terminology

The terms presented in this section include text to assist in understanding their meanings. Nonetheless, nothing in this section is meant to limit the meanings attributed to each word.

Patient

At some point in everyone's life, there are situations that create a real health problem, one that requires medical attention and treatment. The health problem may, for example, be caused externally, by slipping on a bar of soap in the shower, being scratched by a cat, lifting a child in an awkward manner, inhaling some airborne bacteria, being stung by a mosquito that carries malaria, or getting into a traffic accident. Or the problem may arise internally, by some tiny tube clogging up, some organ being overloaded, some tissue degenerating with age, some anatomic system getting too much of one chemical and not enough of another, or some cells deciding to grow unchecked into a cyst or a tumor, for instance. The person with the health problem is called the patient, in order to distinguish him or her from other persons involved in the case, such as the patient's friends and relatives, doctors and nurses, therapists and pharmacists, lawyers and insurance agents and HMOs.

Disease

There are many words for the general concept of someone being sick. A patient may be said to have an abnormality, affliction, ailment, anomaly, cause, complaint, condition, disease, disorder, illness, indisposition, infirmity, malady, problem, or sickness. We use the word disease. Some diseases, such as pregnancy, can actually be joyous news to the patient.

Symptom

As the disease progresses and evolves in the patient, it creates various direct and indirect effects that can be noticed by the patient or externally observed or measured. These signs of disease also have various names in medicine, such as complaint, effect, indication, manifestation, presentation, problem, sign, or symptom. We use the word symptom.

Doctor

A person with symptoms, i.e., a patient, typically seeks help from someone trained in medicine, who may be any one of the following: attendant, clinician, dentist, doctor, expert, healthcarer, MD, medic, midwife, nurse, ophthalmologist, optician, paramedic, physician, practitioner, professor, provider, psychiatrist, specialist, surgeon, or technician. For our purposes, we use the word doctor in its most general sense of someone who is trained and experienced in at least some aspect of medicine, as opposed to the general lay public that has no formal medical training.

Examination

In real-world medicine, the doctor usually examines the patient to determine the extent of the symptoms and to make other observations that the patient is not trained to notice. In the automated medical world of the present diagnostic system, physical examination is necessarily secondary, since the patient is always remote from the "doctor". One partial solution is to train the patient (or an associate) to perform self-examination at home, perhaps with the aid of an examination kit. Another partial solution is to refer the patient to a doctor or to a lab for a specified examination or test. This is often done in real-world medicine, when—for example—a doctor refers a patient to a specialist, or sends the patient to a lab for a special test or examination.

Laboratory Test

Some symptoms can only be measured by special chemical, electronic, or mechanical devices which require a specially equipped laboratory and trained lab technicians. Such labs typically obtain a sample of the patient's body fluids or tissue, called a specimen. They analyze the specimen and report the results to the doctor. A key to understanding lab tests is that one must ask the lab what test to perform. Contrary to public opinion, a lab does not just test "for everything." There are perhaps 1500 different lab tests, and the lab will perform only what is requested. So it is important for the doctor to determine which test to request, and this, in turn, depends on the diagnosis.

With new monoclonal antibody and polymerase chain reactions (PCR) tests, an ever-increasing number of laboratory tests can be performed by the patient or an assistant at home. Examples would be urine pregnancy tests, a urine dipstick to detect leukocyte esterase, and nitrates to diagnose a urinary tract infection. Diabetics prick their skin to get a small amount of blood so that a home glucometer can determine their blood sugar level and, thus, how much insulin to take.

A home diagnostic kit is available that provides the most current technologies, and may be referenced during consultations with the patient if the patient has one.

Imaging Modality

Some symptoms can be observed by devices that display some part of the body as an image. The best known of these is the x-ray. Others are ultrasound, CAT scan, MRI scan and PET scan. Imaging modalities typically require the presence of the patient to take a "picture" of some part or all of the body. The imaging lab takes the picture and may have a resident specialist who interprets the image for the doctor. In any case, the results of the imaging study are forwarded to the doctor.

Session

In the automated method utilized by the present diagnostic system, the patient contacts the system by phone, the Internet or some other communication mechanism. The patient interfaces with the system, so that the system plays the role of the doctor, and no human doctor is involved. One such consultation may be called a session.

Question

In the automated approach used by the present diagnostic system, most of the information about a health problem is obtained during a session, by asking the patient (or someone speaking for the patient) questions. Asking a question typically involves a number of elements such as introducing a topic, giving background, defining terms, suggesting approximations, asking the actual question, and instructing the patient how to indicate the response ("press 1 for yes; press 2 for no"). Thus, question generally includes all of these elements. When reference is made to the actual question, the term question text may be used.

Valuation

In addition to questions, health data can be obtained by various computational algorithms such as sorting and searching, comparing and matching, mathematical or graphical calculations, logical inferences, or looking up data in tables and databases. In the automated method, the word valuation may be used for all computations of health data that do not involve the patient. A simple example is to classify the patient's age into labels used in diagnoses, such as Newborn, Infant, Child, Teenager, Adult, Senior, and so on. Once the system obtains the patient's age from the patient, it does not need to ask the patient whether he or she is a teenager; this can be done internally, using valuator objects.

Diagnosis

In real-world medicine, after the doctor has accumulated the necessary health data from and about the patient, the doctor makes a diagnosis, which means that the doctor identifies the patient's sickness for the purpose of treatment. For every chief complaint, the doctor knows a differential diagnosis, which is a relatively short list of possible diagnoses. After the doctor has accumulated the necessary health data from and about the patient, the doctor has at the least, a patient specific differential diagnosis, and hopefully "the" diagnosis. In the automated method of the diagnostic system, the software establishes the (differential) diagnosis by comparing the patient's symptoms to its database of diseases and symptoms.

Treatment

When the doctor has established the diagnosis, the doctor can take steps to heal the patient. As always, there are many words for this such as advice, counseling, first aid, health care, healing, intervention, medication, nursing, prescription, rehabilitation, surgery, therapy, and treatment. For all of these, this document may use the word treatment.

Disease Management

Some diseases may require continuing treatment and repeated examinations for months or years, or even for the patient's lifetime. Such long-term treatment is called disease management.

Object

In computer software terms, an object is combination of data and processes that manipulate the data. The data are said to be "encapsulated," meaning that they are hidden, so that a user of the object only sees processes that can be invoked. Using an object's processes, one can then manipulate the data without having to know the exact location and format of the data. When more than one copy of the object is required, one can make copies of the data, but use the same process set to manipulate each of the copies as needed. This set of processes can then be thought of as an "engine" that controls or represents the objects'behavior, whether there are 10 or 10,000 object copies.

II. Object-Based Medical Diagnosis

This section describes a new diagnostic paradigm that uses software objects to establish a broad, generalized software environment for medical diagnosis, which is used to define and develop the programming elements of medical diagnosis. The objects are then used to guide and control the diagnostic process, to conduct the patient interview, to perform related analytical tasks, and to generate the diagnoses. A software object is a fundamental software structure that can be used to organize the processes and data of a computer program in such a way as to make possible very complicated applications. This description will discuss novel uses of object oriented programming (OOP) in medical diagnosis, such as the use of software objects for the purpose of fully automated medical diagnosis, the entire/overall method of dynamically assembling the components of diagnosis in the form of objects, and then letting the objects interact to compute a diagnosis.

Defining and creating software objects is well-known to any programmer trained in object-oriented programming. Using an OOP-capable compiler, the programmer defines the data that represent the object and the actions that the object can perform. At run time, the program creates an object, supplies the data that define the object, and then manipulates the object using the object actions. The program can create any number of objects as needed. Each object can be independently initialized, manipulated, and destroyed.

III. The Object-Based Method

In the object-based (OB) method discussed here, software objects are used as active, intelligent agents that represent all of the players and all of the data in suitably organized roles. It is important to note in this metaphor that all of the disease objects, which are "specialists" for a single disease, are allowed to monitor the questions and answers of other objects.

One key concept of the OB method is to think of disease and symptom objects as representing the medical experts inside the computer. If we ask the Appendicitis Disease Object to look at a patient, the object looks at the patient data, notes that the patient does indeed complain of abdominal pain and nausea—but then "notices" the appendectomy scar! Obviously, appendicitis can be ruled out,; but instead of shrugging its shoulders and giving up, the Appendicitis Disease Object now invokes another disease object that is an expert in, say, Small Bowel Obstruction. That object takes a look, asks some questions, and passes the patient on to still other disease objects. In effect, a huge number of diagnostic experts are gathered at the patient's bedside, and each object gets a turn at evaluating the patient data in terms of its own symptom pattern.

As an actual patient symptom set is built up, disease objects judge themselves and judge the likelihood of other diseases. The emergent effect is a patient interview and a diagnostic evaluation that—by design—constantly stays focused on the most likely set of diseases of the patient. Carefully focused questions are used to eliminate or reduce the likelihood of diseases, to promote others into the "realm of suspicion," and to expand the search in a promising direction, based on the data being obtained from the patient.

Object Overview

A software "object" is basically a data structure plus associated processes that can do things with or for or to the data. An important property of an object is that the object's data can be hidden behind the object's processes, so that the outside user of the object can only see and use object processes that can be invoked to access the data. The object is said to "hide" data; it provides the powerful ability of decoupling the world that uses an object from the object itself.

Now assume an object is a "smart doctor". Not one that knows everything about medicine, but just one that knows about, say, "Malaria Vivax in immunocompetant female of child-bearing age that is resident of Upper Gabon". This object knows nothing about anything other than everything about one tiny portion of one specific disease. Next, this disease object is trained to diagnose a patient. It is free to access the patient's medical record, to ask the patient questions, to ask for certain lab tests, and to compare the patient to other patients in the same household or region (e.g., to detect infection or epidemic). In true OOP fashion, the disease object does not actually ask the patient, but it calls a Symptom Object which calls a Question Object, which uses a Node Object, which interfaces with a Patient Object, which interfaces with the Communication Object which interfaces with the Port Object and so on. One of the objects, somewhere down the hierarchy actually displays a message on a screen, or speaks a question into a telephone modem, or sends a question on a fax machine.

Suppose thousands of disease objects have been defined, each with a well-defined, different, specific disease in mind. One disease object is not necessarily matched with one disease, but divide each disease into its major phases. Define Appendicitis as, say, three disease objects: (1) early, pre-RLQ-Pain Appendicitis, (2) middle Appendicitis, from RLQ pain to Rupture, and (3) late, post-rupture Appendicitis. Let these three objects interview a patient and compete with each other as to the condition of the patient.

Now define thousands of symptom objects, each for a different specific symptom. Again, divide complex symptoms into less complex ones, so that they build on each other. Define Cough into, say, 12 types that patients can identify and doctors can use to diagnose. Define fever into useful levels. Define pain into PQRST codes.

Now define a Diagnostic Engine Object, much like the List-Based (LB) Engine described in U.S. Pat. No. 5,935,060, which is smart enough to pit these objects against each other, in a race to be the first to diagnose itself. The engine is built to be smart enough to switch among the disease and symptom objects, so that nobody monopolizes the diagnosis. It is smart enough to know when to stop, to know when it is used for testing and when an emergency patient is online.

The following objects are described as examples of the kinds of objects to be utilized by the system.

A. Disease Object

A Disease Object (DO) is a software object that represents an abnormal health state (illness, disease, disorder, cause) which we collectively call a "disease." It is used in the method to establish the likelihood that the specified disease exists in the current patient.

The object's data are the basic properties of the disease and its runtime state flags, such as:

the name of the disease, its identification code, its prevalence in the patient population, a list of the component symptoms, a list of symptom values and their diagnostic weights, a list of alternative symptom values and their weights, a list of synergies and their weights, threshold values to be used, a list of symptom values established in the patient, the diagnostic score for the current patient.

The object's actions are the numerous functions and procedures needed by the system to manipulate a disease, such as processes to:

pre-test the disease elements, print the disease elements for review/editing by the author, reset the disease for a new patient,
load disease data from the patient medical record (PMR),
diagnose the disease in the current patient,
report the diagnostic score,
write disease data to the PMR.

One of the Disease Object's built-in procedures is called "Diagnose"—a function that diagnoses the current patient for the disease in question. This function invokes the Valuate function of one or more symptom objects, which in turn invoke valuator objects to establish the value of symptoms by looking in the PMR, by calculating a formula, or by invoking a question object to ask the patient a question. Perhaps a better way to present the diagnostic object is as a medically-trained software robot, an idiot savant that knows everything there is to know about only one disease, and knows how to sniff it out in a patient.

The DO is used to capture all that is known about a given disease from an author and other sources, and to diagnose the disease in a patient at run time. The DO can also be used to represent several related diseases that share common symptoms but diverge at some level of detail. For example, Malaria Falciparum, Malaria Ovale, Malaria Vivax, and Malaria Malariae might be combined into a DO Malaria and used to establish or rule out the basic symptoms of malaria before getting into details.

The DO can be used to subdivide a complicated disease into smaller diseases. For example, is might be useful to divide Malaria into (1) Malaria in non-immunocompetant patients and (2) Malaria in immunocompetent patients, to capture the different detailed manifestations of the disease in these patient types.

B. Symptom Object

A Symptom Object (SO) is a software object that represents a patient health item (sign, symptom, complaint, presentation, manifestation, finding, laboratory test result (home or remote), interpretations of an imaging study) which is collectively called a "symptom." It is used in the system to describe patient health in terms that the LB system can use for diagnosis.

The object's data are the basic properties of the symptom and its runtime state flags, such as:
the name of the symptom,
the type of symptom values (numeric, words, graphic),
the valid symptom values (NONE, LOW, MEDIUM, HIGH),
the name of the valuator object used to elicit the values,
the actual (runtime) values, over time, in the current patient.

The object's actions are the numerous functions and procedures needed by the system to manipulate a symptom, such as processes to:
pre-test the symptom elements,
print the symptom elements for review/editing by the author,
reset the symptom for a new patient,
read/write past symptom data from/to the PMR,
valuate, i.e., establish the symptom value in the current patient,
report the symptom value,
report time-based synergy values (onset/offset, slope, trend, curve, area).

The SO may be thought of as a sort of software robot that knows everything about one specific symptom, how to establish at a specified time in the patient, and how to report it as specific values.

One view of the SO is as the fundamental unit of medical diagnosis, the quantum that is used to interface theoretical knowledge about disease to actual manifestation of disease in the patient.

Another view is that the SO plays the role of the variable in the "script language" of the method. By weighting them, the author establishes values of variables to look for, and by summing the value weights, the system finds the diseases of interest to the author.

The basic use of the SO is to encapsulate all that is known about a given symptom, at any point in the patient's lifetime. Symptom values are the units that are weighted in assessing the presence of disease in the patient. The SO can also be used as a syndrome, to collect several symptoms that have medical significance as a group.

A symptom object describes the data and processing elements of any data item that can contribute to diagnosing a patient's disease. In real-world medical terms, a symptom object is known (depending on its context) as a symptom, sign, complaint, observation, test result, manifestation, report, presentation, and so on. In programming terms, a symptom object is a variable that can take on a specified range of values in a patient.

Having said that, it is very important to understand that a Symptom Object is not limited to the classic signs and symptoms of medicine. While classic symptoms (e.g., pain, fever, headache) obviously play a significant role in scripts, the Symptom Object is also used to manipulate other data that somehow contribute to diagnosis, such as the patient's habits, culture, environment, and even education. In addition, symptom objects can be used to build artificial internal data structures as necessary. Thus, a symptom object can be used to define special groups of symptoms (syndromes, if you will), or to control the exact sequence in which the system elicits certain symptoms from the patient, or simply as convenient software containers that perform some computations or a table lookup to obtain a value. The Symptom Object is the "work horse" of scripting, and this is reflected by the fact that many symptom objects are collected into a central system database that can be shared by all script authors, via the Internet.

A symptom object consists of the software elements needed to calculate a "value" that is used for diagnosing a given disease. Values are typically obtained by asking the patient one or more questions, but they can be obtained in other ways as well:
by accessing the patient's medical record,
by accessing the patient's responses to previous questions in this session,
by logical reasoning, using specified implication formulas,
by mathematical computation, using specified formulas.

If a symptom value has been established by other means (such as from the medical record or by implication), the question will not be asked. For example, once the patient's birth date is known, the patient's age will not have to be asked again.

In alphabetical order, exemplary aspects of a Symptom Object are as follows:

| | |
|---|---|
| Answerability | probability that the patient knows the symptom |
| Class | what kind of symptom this is (history, sign, custom, logic.) |
| Documentation | description and development history of the symptom object |
| ICD | ICD-9CM code for the symptom |
| Keywords | search words to find symptom object in the index |
| Label | name of the symptom object (not the symptom) |
| Location | where the symptom can be obtained |

| | -continued |
|---|---|
| Name | formal medical name of the symptom |
| Onset_Offset | special onset/offset attributes |
| Persistence | how long a value is good for, once obtained |
| SNOMED | classification code for indexing the entire medical vocabulary, including signs, symptoms, diagnoses, and procedures |
| Synonyms | alternate names of the symptom |
| Trending | special trending information such as the changes in severity of a symptom with time or the evolution of symptoms in a disease process |
| Valuator | label of the object that actually obtains the symptom values |
| Value | current value of symptom |
| Value_Date | date of last Value |
| Value_Time | time of last Value |
| Value_Type | operational type of the value (integer, real, text, discrete) |

C. Valuator Object

A Valuator Object (VO) is a software object that represents the actions required to establish the value of a symptom in a patient at a specified time.

The VO data are the basic properties of the symptom and its runtime state flags, such as:

the type of valuation used (question, formula, graph, table), the type of value reported (numeric, words, graphic), the valid symptom values (NONE, LOW, MEDIUM, HIGH), if applicable, the question object to be used, if applicable, the mathematical or logical formula used, if applicable, the graph, or table, or database to be used.

The VO actions are the functions and procedures needed by the system to manipulate a value, such as processes to:

pre-test the valuator, print the valuator formulas for review/editing by the author, establish the value in the current patient, report the value.

The basic use of the VO is as an interface between the symptom and the patient level of abstraction. The VO can be used to present dummy patients to the LB system for testing. The VO can be used to switch among lookup tables, based on global system control setting. The VO makes an object out of an action, a common use of objects, so that we can globally describe and control the actions that take place at some lower level.

D. Question Object

A Question Object (QO) is a software object that describes the software elements required to establish a mini-dialog of questions and responses with the patient, in order to obtain a symptom value. It is the task of the QO to select the appropriate question set, to invoke the appropriate node objects that actually question the patient, and to report back the patient's response. A QO is a type of valuator object that specializes in interaction with a patient.

The Question Object is the point in defining a script where the author actually writes a script, albeit typically a very short one, that is focused on asking about one specific symptom. This mini-script is broken down into separate node objects, each of which presents a Preamble, a Question, and a set of labeled Buttons to the patient, and obtains a response from the patient. The QO data are those elements required to ask a question and obtain a response from a patient, such as the list of node objects to be used.

The object's actions are the functions and procedures needed by the system to manipulate a question, such as processes to:

pre-test the question and node elements, print the question elements for review/editing by the author, ask the question and report the response, specify the actual natural language text to be used, establish the user interface required for the current platform, invoke a node object to actually ask the question and report the response.

The QO is another interface object, used to separate the questioner from the language used to question the patient. The basic use of the QO is to handle the details required to present a (possibly complex) question to an online patient. The QO can be used to change the educational level of the question text (Question Roller). The QO can be used to change natural language used to speak to the patient.

E. Node Object

A Node Object (NO) is a software object that describes the software elements required to ask a single, well-defined question of the patient and to return the response selected by the patient. It is the task of the NO to present the required data to the GUI in a form that will appear user-friendly manner on the user display, to wait an appropriate amount of time for a user response, to possibly re-prompt the user, and to ultimately return the user's response.

Node objects operate at the lowest level of the script hierarchy; they interface to the operating system's user interface. Computation depends on the platform used. For a Windows operating environment, the node would display an appropriate window containing sub-windows for the Preamble and Question Text. Next it would display the requisite number of buttons and display the form to the user. When a button is pressed by the user, the node object returns the index number of the response.

The NO data are those elements required to ask one detailed question, obtain a response, and return the index number of the response. The NO's actions are the functions and procedures needed by the system to display a question to the user, such as processes to:

pre-test the node elements, print the node elements for review/editing by the author, display the question and report the response.

The NO is another interface, between the script objects and the patient. The basic use of the NO is to handle the low-level details required to "talk" to a patient. The NO can be used to port an application to another hardware platform or operating system. The NO can be used to "fake" a patient by taking inputs from a test file and writing outputs to a test result file. The NO can be used to log all questions to, and responses from, the patient, time-stamped to the nearest hundredths of a second if necessary. One of the reasons for defining Node Objects as well as Questions Objects is that the entire system can be translated into other languages by translating all of the Node Objects.

IV. List-Based Engine Concepts

In one embodiment of the invention, the List-Based Engine (LBE) is one embodiment of the diagnostic processing method. It is a program that, essentially, takes a set of diseases (more precisely a collection of disease descriptions, symptom definitions, and question specifications) and processes them against one specific patient.

The patient is typically a human that can conduct an interactive dialog with the system and can respond to questions posed by the system. Alternatively, the patient may be represented by a medical record in which some or all symptoms already have values, so that the system simply sifts the values and scores the diseases accordingly. For test purposes, the patient may even be represented by a computer program that is "playing patient" in order to test the system's ability to respond to abnormal situations such as unexpected key presses, extensive response delays, contradictory answers, requests for repeating a question, and abnormal termination of a session.

For a specific run or session, the system begins its work by gathering a set of candidate diseases that it is supposed to diagnose. This initial candidate list is most likely assembled by a module that has analyzed the patient's Chief Complaint and selected appropriate diseases from a database that is indexed by chief complaint. In the absence of a chief complaint, the system can just start with all the diseases it finds in a given project file, where an author wants to test a newly created or edited script.

Once it has a list of candidate diseases, the system's job is to process these diseases, typically by asking questions and accumulating diagnostic scores for each disease until some specified system goal is reached. This system goal is expressed by the system "Mission" setting, which can specify various goals such as "run all diseases" or "run until the first disease is ruled in" or "run until 10 minutes have passed", and so on. The default system mission is to "run all diseases until all symptoms have been evaluated".

Diagnostic Loop

In one embodiment, the system uses a "diagnostic loop" to process the current disease list. Portions of the diagnostic loop have been described in Applicant's U.S. Pat. No. 5,935,060, which is hereby incorporated by reference. The diagnostic loop consists of a series of iterations in which the system considers its mission in the light of the latest status of all candidate diseases. Depending on the mission, the system can perform all kinds of special calculations and evaluations during this loop. The loop actually consists of several nested loops that may involve recursion to evaluate subordinate symptoms.

Current Disease

In one embodiment, during the diagnostic loop, the first aim of the system is to determine which disease it should evaluate next, based on its mission. The mission might be to "evaluate the disease with the highest score", or "evaluate the disease with the highest diagnostic momentum", or "evaluate any random disease". The default mission is to evaluate the next disease as originally given in the candidate list.

Current Symptom

In one embodiment, once it has a "current disease", the next system aim is to determine which symptom of the current disease it should evaluate next. The mission might be to "evaluate the symptom that can add the highest weight to the score of the current disease". A more complex mission might be to "evaluate the symptom that will advance the score of the most diseases". The default mission is to evaluate the next symptom in the symptom list of the current disease.

Current Evaluation

In one embodiment, evaluating a symptom consists of establishing the value of the symptom for a specified date and time in the patient's life. How this is done depends on the type of symptom and on the type of the valuator object defined for the symptom. A symptom may already have a valid current value in the patient's medical record. For example, the patient's gender may already be in the medical record, in which case the system obtains it and continues.

The patient may already have supplied the symptom value during the current session in the context of a question for some other disease. Again, the system obtains the symptom value from the current session record. (This feature avoids asking the patient the same question in the process of evaluating different diseases.) Many symptoms are evaluated by running a Question object, i.e., asking the patient one or more questions. Symptoms may use a Logic object to evaluate a value; this means that the system parses and runs a logic formula, such as "if patient has symptom value A and has symptom value B, then the value of this symptom is C". To evaluate this symptom, the system would (recursively) evaluate symptoms A and B and then establish C, if appropriate.

Scoring

In one embodiment, after the system establishes a new symptom value, it updates the scores of all candidate diseases. Depending on the description of each disease, scoring can consist of simply adding the weight corresponding to the new current symptom value, or it can involve adding special synergy weights based on the values of other symptoms, or on the timing of symptoms. Scoring can also include establishing probabilities of diagnosis, which typically depend on the existence of several symptom values, sometimes in a defined time order. Finally, scoring includes evaluating the scores of diseases against various thresholds. Depending on the system goals, a disease may be placed into a special category based on its score. For example, a disease may be deemed "ruled in" when its score reaches or exceeds a specified threshold, or it may be placed on a special diagnostic momentum track if its score is increasing more rapidly than other disease scores. The default system goal is to add the symptom weights to all applicable disease scores.

Continuation

In one embodiment, after the system has updated the scores of all diseases, it determines how to continue by considering the set of new scores. Again, the system's goals can specify different actions for the system, such as "stop when any score exceeds 1000" or "stop when the diagnosis has been ruled in" or "stop when the system has the five most likely diagnoses" or "stop when ten minutes have elapsed". The default goal is to run until all symptoms of all diseases have been evaluated.

A. Dynamic Rules and Goals

In one embodiment, the system is designed so that the rules, limits, and goals that govern the diagnosis can be changed at run time. The system may use tables of rules and goals and limits, of which the applicable set is selected as needed.

For example, at the top of the diagnostic loop when the system selects the next disease to be considered, it can use any one of a number of rules such as "Select the disease that:
- is the most life-threatening disease remaining to be diagnosed,
- shares the most symptoms with other diseases,
- has the highest current diagnostic score,
- has the highest current change in diagnostic score,
- has the fewest unresolved symptoms,
- is next in some order specified by the author."

Similarly, when the system selects the next symptom with a disease, it can choose it based on various dynamic modes or control variables.

The patient him/herself can set certain boundary conditions on the consultation. Several examples include:
- a patient who has only 20 minutes to talk
- a patient who wants only to exclude a certain disease ("e.g., my friend had a headache like mine, and he was diagnosed with brain tumor")

B. Diagnostic Momentum

In one embodiment, the "diagnostic momentum" is the rate of change of the diagnostic score of a candidate disease. It provides a measure of how fast a given disease is accumulating diagnostic weights, compared to other competing candidate diseases. The system tracks the score and the momentum for all candidate diseases and can use this information to change the diagnostic mode. Note that the use of various synergy weights will add extra weight to diseases with many matching symptoms, so that positive feedback is established that tends to favor diseases with many matching symptoms and thus to converge rapidly on one disease (see e.g., Sequencing Synergy and Summation Synergy).

As the LB method diagnoses, it tracks for each disease the latest diagnostic score, the last change in the score, and the name of the disease with the largest momentum during the current iteration of the diagnostic loop.

Since the name of the disease with the highest momentum is available at all times to the LB engine, it can be used to guide the diagnostic process itself and to check whether any goals or limits or decision points have been reached. It provides the LB method with feedback that lets it feel its way along a diagnostic path in a manner that is strongly driven by the patient's responses. For example, the faster a disease is approaching the diagnostic threshold, the more intensely the LB method can focus on disease.

This feature simulates the manner in which a human doctor sifts his knowledge of disease based on what s/he is learning about the patient's condition. As the symptom pattern begins to match the pattern of a specific disease, the doctor will ask questions designed to confirm (or reject) this disease.

The advantage of the momentum feature is that it (1) quickly de-emphasizes many less relevant diseases, (2) minimizes questions asked of the patient, and (3) cannot be done as rapidly and as precisely by the human doctor as by the computer.

C. Horizontal Axis of Inquiry (HAI)

In one embodiment, the system conducts its diagnostic inquiries along various "axis", i.e., lines of investigation or focus directions. We call two of these strategies the Horizontal Axis of Inquiry (HAI) and the Vertical Axis of Inquiry (VAI). This section focuses on the HAI. Note: The "inquiry axis" terminology relates to the manner in which the system selects the next focus symptom. The terminology derives from the Disease/Symptom Matrix (DSM) metaphor, in which a table is formed by arranging the candidate diseases as side-by-side columns (hence "vertical") and the component symptoms as rows (hence "horizontal"). See the DSM figure. In database terminology, fields are arranged along the vertical, and records arranged along the horizontal. The Horizontal Axis of Inquiry (HAI) strategy is a diagnostic mode that focuses on quickly eliminating inapplicable diseases from a large list of candidates. HAI is typically used early in a diagnostic session, when the system has numerous candidate diseases and selects focus symptoms based more on how many diseases contain the symptom than on how effective the symptom will be in identifying one disease.

Other diagnostic methods have one and only one method. The present invention, by contrast, allow many different modes of inquiry, which are themselves dependent on the progress of the diagnosis. In both the HAI and VAI strategies, the LB engine updates the scores of all candidate disease scores with the responses obtained from the patient. Thus, the differences in these strategies relate primarily to how the system selects the next focus symptom, not how the candidate disease scores are updated.

In the HAI mode, the Alternative Symptom (AS) feature will typically be activated, so that fewer and more general questions tend to be asked. In the VAI mode, the AS feature may or may not be activated, depending on the need for more detailed responses from the patient.

The choice between HAI and VAI strategies is very important because it permits general "sifting" of many candidate diseases as well as focusing on diagnosis of one specific disease, at a detail level where the patient can—indirectly—interact with the script author, a world specialist on that disease. Other medical diagnostic systems typically interact at one and only one level with the patient.

The decision which one of these (or some other) strategies or modes to select can be programmed to depend on any number of variables. For example:

it may be specified by the process that calls the system;

it may be modified based on the goal selection routine that runs early in the consultation;

it may be switched based on the Diagnostic Score or Momentum reached by one or more diseases;

it may be switched by various computations related to the Chief Complaint or the First Significant Symptom;

it may be switched based on a new response by the patient, which negates or significantly modifies a previous response.

In the HAI strategy, the system searches the list of candidate diseases and their symptom lists to find symptoms shared by many diseases. It selects such a shared symptom and evaluates it, typically by asking a question, or by evaluating a formula or a logic structure. Then it updates every disease with the new value of the symptom, and adds the appropriate weights to each disease score.

In the HAI strategy, the system can sort the candidate diseases by the number of shared symptoms to prepare for an efficient subsequent elimination process. For example, by establishing the gender of the patient, the system can eliminate all gender-specific disease. The HAI strategy permits the system to partition the candidate diseases into useful classes so that it can focus on promising classes first. For example, it might partition diseases into the following categories: urgent, serious, common, or it might partition diseases into promising (high probability that the diagnosis is among them), intermediate and low probability.

D. Vertical Axis of Inquiry (VAI)

The Vertical Axis of Inquiry (VAI) strategy is used to examine one candidate disease in detail, so that the system selects the next focus symptom repeatedly from the same disease. This strategy is intended to give one specific disease that has scored significantly the chance of establishing itself as a diagnosis. The VAI strategy is equivalent to letting the script author (1) ask several successive questions about this disease and (2) ask his or her preferred questions, in cases where the patient has previously answered Alternative Symptoms.

In the VAI strategy, the LB engine evaluates the various symptoms of one disease. Symptoms can be selected in various orders, depending on the engine mode. In one embodiment, the script author may prescribe a sequence in which symptoms are evaluated, but this can be overridden by first asking for symptoms that carry the most weight, or for symptoms that are the easiest or fastest for the patient to answer. The system selects such a shared symptom and evaluates it, typically by asking a question, or by evaluating a formula or a logic structure. Then it updates every disease with the new value of the symptom, and adds the appropriate weights to each disease score.

In the VAI strategy, a patient who has earlier answered questions using Alternative Symptoms (see there) can now have the opportunity to be asked the symptoms which the author defined. This has the effect of "fine-tuning" the answers to the specific disease at the point when the disease is becoming a contender. In this way, a patient can be promised that no matter what disease they have (if the system covers that disease) they can be guaranteed to interact with a dialogue created by a world-class specialist in that disease.

The VAI strategy can be set to use only the author's own symptoms, instead of accepting the (normally alternative) symptoms of other authors. This means that the system can (perhaps at the patient's request) re-ask all symptoms using only the authors' own questions. This, in turn, means that the patient's entire consultation on a given disease can ultimately be conducted using the world expert on the disease. This gives the LB method the ability to shift from the broad, generalizing viewpoint (where it accepts all alternative symptoms) to the narrow, specific viewpoint, where the world expert's questions phrasing may help to distinguish among close diseases.

The HAI and VAI strategies are part of the central processes for symptom selection of the system, specifically the LB Diagnostic Loop. The decision which one of these (or some other) strategies or modes to select can be programmed to depend on any number of variables. For example, it may be specified by the process that calls the LB engine; it may be switched based on the Diagnostic Score or Momentum reached by one or more diseases; it may be switched by various computations related to the Chief Complaint or the First Significant Symptom; it may be switched based on a new response by the patient, which negates or significantly modifies a previous response.

The VAI and HAI strategies permit the system to vary its diagnostic focus from the general to the specific. In the early stages, the engine knows little about the patient and must ask the best general questions that quickly eliminate large numbers of candidate diseases. But after applying the HAI strategy for a while, if the diagnostic momentum of some disease D reaches a specified level, the engine can then switch to the VAI strategy to focus diagnosis on disease D, to the momentary exclusion of all other diseases. It is important to note that all of the disease object (experts) "monitor" all of the questions and answers generated by other disease objects. After applying VAI for a while, disease D may emerge as the "front runner", or it may fade, being outstripped by one or more other disease scores. One of these may then become the driver of another VAI round, or the diagnostic strategy may revert to HAI if no disease has a clear lead.

There is a powerful holistic effect when various LB features such as Disease Momentum, Dynamic Goals, HAI, VAI, Alternative Symptoms, and Synergy Weighting are combined. Consider how the LB engine sifts the candidate diseases and converges on the appropriate ones: As one disease gains score and momentum in the HAI strategy, this triggers a shift to VAI strategy. If the system is "on the right track", the VAI strategy will rapidly confirm that several key symptoms of that disease are present in the patient. Through the various Synergy weights, this confirmation will increase the score and the momentum, and reinforce the cycle to converge on the focus disease as a diagnosis. In one embodiment, the symptom weights may be increased when the system is operating using the VAI strategy. This feature allows the system to accommodate Bayesian probabilities in the evaluation process. On the other hand, if the system is "on a cold trail", the VAI strategy will fail to confirm additional symptoms, the disease score will lag behind those of other diseases (which are being updated in parallel) and the system will soon abandon this fruitless pursuit and either return to the HAI strategy, or select another disease for a VAI inquiry.

E. Alternative Symptoms

In one embodiment, the Alternative Symptom feature of the LB method lets a disease author specify a set of symptoms that are alternative to a specified symptom for the purpose of diagnosis. The invention lets an author specify alternative symptoms that can take the place of the author's preferred or specified symptom, perhaps with a different weight. The feature is designed to solve the problem that different authors may prefer different ways of asking a patient about the same symptom, yet we do not want the patient to have to answer questions about the same symptom over and over.

The LB engine is programmed with alternate modes that either do or do not permit symptom alternatives. When permitted, the system accepts the value of any alternative symptom as the value of a symptom; if not permitted, the system requires the asking of the author's specified symptom, even if this requires asking the patient certain questions a second time. One goal of the LB diagnostic method is that, no matter which disease the patient has, he or she will be asked questions by a world-class specialist in that disease. This feature mimics how human doctors interview a patient: In the early part, the doctor asks broad questions that determine the general overall nature of the patient's disorder. Once one disease emerges as a likely diagnosis, the doctor asks more specific questions that confirm or reject the hypothesis to some degree. Finally, when the most likely diagnosis seems almost obvious, the doctor asks even more detailed questions in order to repeat, emphasize, seek more details, add confirming symptoms, and so on. These final question may well repeat questions asked earlier, perhaps to give the patient a final chance to confirm earlier responses.

The Alternative Symptoms feature gives the patient the option to go back and answer questions exactly as worded by the original disease script author, or to simply accept the questioning by the alternative symptoms. This is analogous to a computer user who installs an application who can either insist on a "custom installation" or accept the "typical installation".

At scripting time, when the author of a disease script first lists the component symptoms of the disease, the author can either specify brand new symptoms, which the author writes from scratch, or specify existing symptoms, which the author retrieves from a database of stored or archived symptoms that is shared by all authors. This initial symptom set becomes the author's preferred or specified symptoms, which the author prefers to be asked of the patient. Next, the author reviews the symptom database to see which symptoms are so "close" to his/her specified symptoms that they can serve as alternatives. The author lists these alternative symptoms and assigns some diagnostic weight to them. One author's specified symptom is another author's alternative symptom. Thus all symptoms are specified symptoms to some author, who is responsible for maintaining their currency.

Each of the authors may be linked by a data communications network such as the Internet. When a new symptom object is created by Author A, a copy of the new symptom object is instantly "sent" to the authors of the diseases in which his symptom is also used, e.g., Author B. This then would be an alternative symptom for Author B. Author B then assigns a weight for the disease he is authoring when this new alternative symptom is used in a question.

At run time, the system can either allow or disallow the use of alternative symptoms. If the system is in the alternative symptom mode, and the system is seeking the value of specified symptom S1, it may accept the value of any alternative symptom in its place. The effect is that, if the patient has already been asked about any alternative symptom S2, S3, or S4, the system will not ask the patient again, but will accept the alternative symptom and its weight. If the system is not in the alternative symptom mode, when the system seeks the value of specified symptom S1, it will proceed to ask the questions associated with symptom S1.

The Alternative Symptom feature eliminates redundant questioning of the patient and permits the author to group symptoms together that have the same impact on his disease. The Alternative Symptom feature lets the author control how she or he wants to focus on symptom details, i.e., on the quantization of symptoms. For high-level diagnosis, a high level of quantization may be sufficient; at a later time, the author may need more precise details, such as to distinguish between close variants of a disease.

In one embodiment, the system symptom database may contain several thousand symptom script elements, written independently by several hundreds of authors. Many of these symptoms may be the same, or be acceptably similar variations of each other. Without Alternative Symptoms, the system would load all candidate diseases. In the course of running them, the engine might encounter some of these similar symptoms several times. The effect would be to ask the patient the same question in many different ways, which would be inefficient and would not engender confidence. But with the Alternative Symptom feature, after the system evaluates any one of the alternative symptoms, the other symptoms in the set will not be asked.

A benefit of the object-based system having Symptom Objects and using the Alternative Symptom feature is that Symptom Objects and their underlying objects, e.g., Valuator Objects, Question Objects and Node Objects, can be "reused". In one embodiment, the author of a new disease script can reuse previously written and debugged objects by a few steps, which may include, for example, renaming one or more of the objects and assigning alternative weights. This object reuse capability permits faster coding, testing and release of new disease scripts.

F. Disease Timeline

In one embodiment of the invention, the Disease Timeline may be a chart or graph that describes how each symptom of the disease manifests itself over time in a typical patient. The timeline is a characteristic "pattern" of the disease that can be used as a reference for comparisons of the patient's actual symptom time chart.

This aspect of the invention relates to pure medical knowledge about a disease; it is independent of any one patient. This aspect is "theoretical", in contrast to a Symptom Time Chart, which relates to the "actual" symptom values as experienced by a patient over time.

The timeline is for a generic occurrence of the disease, to serve as a base reference. It can be scaled to fit a given patient.

At design time, the author of a disease object describes the typical course of the disease in terms of how and when its symptoms typically arise (onset), vary, and subside (offset) over time. This timeline starts with the First Significant Symptom (FSS) of the disease, and all timings are based on the start of the FSS. Note that the FSS may be different than the patient's chief complaint.

One embodiment utilizes a Gantt chart that records the times of the appearance, disappearance, overlap, and other aspects of the component symptoms. Initially, the author might only choose three time points for each symptom; later, more and more points can be added. A typical goal is an hour-by-hour description of the disease.

At run time, the system matches the patient to the script. Appendicitis may be used as an example disease to walk through a simple diagnosis. Assume that the author has chosen to describe the disease as follows: The first symptom is often (though not always) anorexia, so this symptom is the origin for the timeline. Anorexia, then, occurs at 0 hour. At hour 1, one typically expects nausea. At hour 3, one expects epigastric pain to become noticeable to the patient. By hour 8, one can expect the pain to be migrating to the right lower quadrant of the abdomen, and so on.

At run time, when a patient enters the system, the system preferably asks when the chief complaint started. In one embodiment, the system then selects the script that is nearest in time. So, here is a patient with appendicitis calling the diagnostic system; she or he may, of course, be at any stage along the disease timeline. Usually an appendicitis patient waits until she or he has abdominal pain before seeing a doctor. So, let's say our patient presents abdominal pain of a given severity as the chief complaint.

The system (in HAI mode) then searches all candidate scripts for abdominal pain of our patient's severity. It finds the appendicitis script, which indicates where a patient with that severity should be placed along the time line. The disease object can now compute the time offset required to match the patient, and can "place" or "match" the patient to that point in time in the appendicitis script.

Sooner or later, the LB system will let the appendicitis script ask another symptom. The script will ask the patient about earlier nausea or anorexia, and—if the patient confirms—will add weight to the score of appendicitis. At some point, the rising score will trigger the system to switch to VAI mode, and to ask about several more symptoms from the appendicitis script. This may rapidly pile on more weight, and the appendicitis diagnosis would then exceed threshold and would be ruled in. If not, the system will know what symptoms should appear next, and let the patient know.

The chart, graph or timeline described above may also be referred to as a predetermined template of symptom characteristics. One or more of the established symptoms may have symptom characteristics that arise (onset) or subside (offset) over time so as to match the predetermined template. If so, additional weight is added to the score for the particular disease. Furthermore, if the onset or offset characteristics match the predetermined template and a set of the established symptoms occur in a specified sequence over time, still more additional weight is added to the score for the particular disease. Thus, it can be seen that when certain symptom conditions are met, the score of a particular disease may rapidly reach the disease threshold and be ruled-in or diagnosed.

A disease needs time to "declare itself." On one hand, the longer one waits in a disease process, the more certain they can be of the diagnosis; on the other hand, one wants to make the diagnosis as soon as possible to begin appropriate treatment.

The author actually has two "clocks". One clock is related to the appearance of the Chief Complaint, the other clock is related to the appearance of the First Significant Symptom. The HAI mode uses the CC clock, while the VAI mode uses the FSS clock, which is more accurate, but cannot be used until one has a tentative diagnosis.

See FIG. 28 for an exemplary screen shot of a user interface for specifying the order of a particular set of symptoms so as to establish the First Significant Symptom. The user may for example, slide symptom bars along the time axis to indicate their particular symptom history. The user would then click on the "submit" button which causes the new symptom occurrence times to be captured and then evaluated by the system.

The author can also use the symptom timeline as a characteristic pattern of symptom magnitudes. This is useful in describing and differentiating diseases based on their symptom patterns.

G. Spectrum of Terms/PQRST Code

In one embodiment of the invention, the PQRST Code is a comprehensive method for capturing and encoding a patient's verbal description of a symptom. It is particularly suitable for highly subjective symptoms that are hard to quantify, such as the patient's overall health, the characterization of a particular pain, or the expression of a mental state or emotion. The key invention here relates to the "Vocabulary of Diagnosis." This refers to the ability of the LB method to let an expert author use the exact vocabulary she or he has developed over years of experience in questioning the patient. In the real world, certain words used by patients to describe pain are classic indicators of specific disease. In the LB world, this is implemented by letting the patient select from a pick list of words that are then associated with a predetermined diagnostic weight. The PQRST Code may be used to track changes in other health data such as lesions, masses, discharges, body functions, mental states, emotions, habits, addictions, and so on.

Pain is a subjective experience of the patient. It is diagnostically highly useful, yet practically very hard to describe in sufficiently useful detail. The PQRST Code is a comprehensive method for encoding a patient's description of pain, and for using the pain code for diagnosis in the LB method, and for other purposes such as Advice, Prescription, Treatment, Pain Management, and Disease Management. In the LB diagnostic method, the PQRST Code may be used to encode subjective symptom descriptions, to capture changes in symptom descriptions, and to analyze changes over time. Not only may the PQRST Code itself be composed of hundreds of elements, but the possible uses of the code in medical automation are manifold. The PQRST Code is directed to manipulating medical knowledge in an automated way. The basic idea is using word spectra and pick lists to capture a patient's subjective description of some health experience. The PQRST Code may then be used to detect symptom changes, slopes, trends, areas, and so on, where change is the key. The PQRST Code feature includes picking words from a word spectrum at two points in time, and then analyzing the significance of the change, and using this to give extra weight to one diagnosis. This feature places words in the spectra that do show how a particular aspect of pain is likely to change over time, and then does the second evaluation and gives extra weight to one diagnosis because it manifested the expected change.

The PQRST Code feature includes methods for:
 describing some 20 aspects of pain,
 obtaining these aspects from the patient,
 encoding and decoding these aspects as a single PQRST code,
 using the PQRST code in diagnostic and other contexts.

At the global level, for all authors and all script, we define some 20 aspects of pain, such as Quality, Severity, Location, Size, Symmetry, Timing, Localizability, and Migration aspects. For each aspect, we further define a word spectrum that consists of a set of words commonly used by patients to describe that aspect of pain. For example, the Quality of pain might be described in terms of "pinprick, knifing, tearing, fullness, tightness, pressure." The Severity of pain would be rated by the patient on a scale of 0 to 10. Word spectra are, of course, different for different aspects of a symptom. Non-pain symptoms might rank some aspect like "Age" along a numeric scale such as 0–7, 8–22, 23–65, and 66 and over. Another spectrum might use words such as NONE, LOW, MEDIUM, HIGH to characterize an aspect. Or, a word spectrum might consist of a vocabulary of descriptor words such as PULSING, POUNDING, HAMMERING, TAPPING. The script author defines diagnostic weights for each word of a spectrum. At run time, a given spectrum is presented as a pick list from which the patient can choose. The patient picks one word from the list, and the system adds the associated diagnostic weight to the score.

The PQRST Code feature permits authors to apply the vocabulary of diagnosis that they have developed over years of experience. A script can use several word spectrum symptoms to build up a PQRST Code that summarizes the state of health of a patient at some time "t". This code can be stored in the patient medical record (PMR) for later use. This is another example where a symptom object specialized for word spectra may be defined. The script can collect a PQRST Code for different times T1, T2, T3. The script can then analyze the changes in code over time, and assign weights for significant symptom changes over time. The script can use the PQRST code to compute synergies based on slope, trend, area, volume, and other properties.

Frequently during the same consultation, the severity of the patient's symptoms is trended. In addition, many PQRST array spectra can be asked at the beginning and at the end of the same consultation. The reenter function (second consultation for the same disease process) and the reenter function (third consultation for the same problem) are used in concert with the PQRST array to evaluate the evolution of the disease process to make the diagnosis.

Each author is able to use or re-use the word spectra that are already created. Each spectrum is typically 7 to 11 adjectives that are carefully selected. For example, if a patient's epigastric pain (location) which cannot be localized (localizability) moves (migration) to the right lower quadrant (location) and now is easy to localize (localizability), the patient has appendicitis.

The diagnostic system can collect and publish medical statistics on the "vocabulary" that is used in diagnosis. The diagnostic system can use the vocabulary as a "digitized medicine" to fine-tune scripts and their actions.

The following is an example of PQRST Code that tracks the nature of a discharge, instead of a pain. The Mallory-Weiss syndrome consists of a partial thickness tear in the very inferior aspect of the esophagus. It is caused by severe vomiting. Hence a patient who is vomiting food at time "t" and vomiting food with blood in it one hour later has Mallory-Weiss syndrome, compared with a patient with a gastric ulcer, who would have blood in the vomit from the beginning. Therefore, a symptom built around PQRST encoding of vomit contents will detect the addition of blood and add the appropriate synergy weight to the Mallory-Weiss disorder.

H. Synergy

In one embodiment of the invention, and in the context of automated medical diagnosis, "synergy" means adding extra diagnostic weight to a disease if a symptom occurs in the patient in a specified manner, intensity, anatomic location, frequency, sequence, combination with other symptoms, or similar pattern. The synergy concept provides a way for an automated diagnostic system to take into account the symptoms of a patient viewed as a holistic pattern that can be used to incrementally refine the ranking of a disease for the purpose of diagnosis.

The word "synergy" may have the meaning of "combined effect." It refers to accounting for the special additional impact on diagnosis of the fact that a symptom is occurring, changing, or interacting with other symptoms in the patient in some well-defined manner with respect to time, anatomic space, quality, sequence, frequency, combination, mutual causation, and so on. In short, the synergy concept implements in software the medical fact that the diagnostic significance of a combination of symptoms is much greater than the significance of each of the symptoms in isolation.

For example, applied to the LB diagnostic method, the synergy concept significantly enhances the capabilities of the method, because the weighting mechanism of the LB method can be used to detect and account for the presence of synergy in the patient's reported symptoms. In fact, synergy allows the LB engine to dynamically adjust the very diagnostic process itself after every response from the patient.

The synergy invention approximates the cognitive process of a human medical expert by providing for non-linear weighting of symptoms, by incrementally adding small weights to account for fine differences in patient health states, by fine-tuning the diagnosis, and by dynamically guiding the diagnostic process itself into productive channels.

Using synergy, the symptom object of the LB method becomes a smart process that does not just store symptom values, but that can perform dynamic intelligent internal analysis of how the symptom behaved over time in the patient, which generates useful diagnostic information in its own right.

In the context of certain embodiment of the LB diagnostic method, the word "synergy" has the normal dictionary meaning of "combined operation or action". Again, it refers to measuring the special, additional impact of several symptoms or symptom changes being present at the same time or in some prescribed sequence. The synergy concept implements in software the real-world medical fact that the diagnostic significance of a syndrome is much greater than the significance of its component symptoms in isolation.

As detailed later for every individual synergy type, the synergy concept significantly enhances the LB method, so that special health conditions and their changes in a patient can be:

- detected by suitable questioning or computation, and
- assigned diagnostic weights in advance, then
- combined logically and mathematically, and
- used to score candidate diseases, which are
- used to rank candidate diseases, which are finally
- used to select those diseases that the patient most likely has.

The system diagnostic methods include a novel and non-obvious way to compute a medical diagnosis. By this method, an medical script author can describe in advance certain specific health conditions and effects in a patient which tend to be less obvious and more difficult to detect by other methods. In certain embodiments of the present automated medical diagnosis system, synergy means special manifestations in the anatomic systems, over time, of patient-specific symptoms and patient-driven verbal descriptions of symptoms. The synergy invention mimics human cognition by providing for non-linear weighting of diagnoses by incrementally adding fine differences in health states, by fine-tuning the initial diagnoses, i.e., by allowing the medical judgments of the script authors to be implemented in an automated manner. Synergy allows the LB engine to watch and to dynamically adjust the very diagnostic process itself after every response from the patient.

Recall that the LB method defines a "symptom" as any patient data item that can affect diagnosis. Therefore, all of the mechanisms used by the LB method to select, evaluate, and record the impact of symptoms are available and used to handle synergies. At script writing time, authors define synergies and assign weights to them like any other symptom. If the author intends to weight the, say, symmetry of onset and offset, the author defines a symptom and a question that will elicit the information directly from the patient or indirectly from other data such as the value of other symptoms. At run time, the LB engine, whether in the Horizontal Axis of Inquiry or in the Vertical Axis of Inquiry, selects symptoms, evaluates them, and—if applicable—adds the associated weight to them.

One feature of the LB method that bears noting, is that it diagnoses disease by assigning "weights" to the patient's symptoms and then uses the weight accumulated by a set of candidate diseases to determine which disease(s) the patient most likely has. The basic weight assigned is for the mere presence or absence of a symptom. Now, under the synergy concept in certain embodiments, there are two additional ways to analyze more detailed aspects of symptoms. First, for each individual symptom, the system can diagnose based on whether it is "first" for a given disease, and on the manner in which the symptom starts, varies, and stops. Second, when several symptoms are present, the system can diagnose based on their presence as a combination, their sequence and extent of overlap in time, and their relationship to (and change in) the anatomic systems of the patient. In other words, these synergistic weights are "refinements" of the fundamental weighting. They specify in detail the considerations for which the LB method can add extra diagnostic weights to a disease. This idea is referred to as "synergy weighting"; it reflects the fact that more detailed knowledge about one or more symptoms of a patient can be used to refine and focus the diagnosis.

The following table lists several type examples of synergy that can be implemented. The examples are, of course, not exhaustive; they can be extended to any special pattern of one or more symptoms occurring in a patient.

| Synergy Type | This synergy adds weight to a disease if it detects that ... |
|---|---|
| Symptom Presence | patient has symptom A (the basic weighting concept) |
| Symptom Level | symptom A has specific value (PAIN SEVERITY = 8 out of 10) |
| Time-Based Synergy | symptom A varies, cycles, pulsates, comes/goes, repeats |
| Onset/Offset Slope | symptom A starts or stops at a specified rate |
| Onset/Offset Trend | the rate of symptom A is changing in a specified way |
| Onset/Offset Symmetry | symptom A starts and stops in a similar manner |
| First Significant Symptom (FSS) | patient has the same FSS as defined for the disease |
| Simultaneous | patient has a specified symptom set A, F, J, and R. |

-continued

| Synergy Type | This synergy adds weight to a disease if it detects that ... |
|---|---|
| Sequencing | symptoms A and B occur in a specified sequence |
| Overlap Synergy | the length of time that symptoms A and B occur together |
| Integral Synergy | the area under the curve of, for example, plotting the severity of a patient's pain over time |

The following sections relate to describing and weighting specific synergy types in certain embodiments of the invention.

1. Symptom Presence Synergy

Symptom presence synergy assigns basic diagnostic weight to a candidate disease if a given symptom is present. At design time, the author can assign a weight to a symptom if it is present. For example, if the patient has a smoking history of ten pack-years, the disease EMPHYSEMA may get 50 points; if the patient recently went on a jungle expedition, the disease MALARIA may get 50 points. At run time, the system determines if the symptom is present in the patient and assigns a weight to all diseases for which the symptom has been pre-defined with a weight.

Knowing the presence of symptoms, even without a value or time reference, can help to select candidate diseases for subsequent diagnosis. Thus, a different set of candidate diseases can be selected initially for a patient complaining of COUGH than for a patient complaining of BACKPAIN.

2. Symptom Level Synergy

Symptom level synergy assigns diagnostic weight based on a level of a symptom present in a patient. At design time, the author defines several levels for a symptom, and weights for significant levels, such as:

| | |
|---|---|
| SEVERITY = 0 | 0 points; |
| SEVERITY = 1 | 10 points; |
| . | |
| . | |
| . | |
| SEVERITY = 9 | 250 points; |
| SEVERITY = 10 | 350 points. |

At run time, the system determines: (1) if the symptom is present and (2) at what level and, if so, (3) adds the corresponding weight to the disease score.

The author can define symptom magnitude with any appropriate resolution. This is obviously very useful in describing diseases more precisely in terms of their symptom patterns.

3. Time-Based Synergy

Time-Based Synergy is the ability of the LB method to analyze the manner in which a symptom varies over time in the patient, and to assign extra diagnostic weight to selected diseases based thereon. The way in which a symptom varies over time has great diagnostic significance. One example is pain over time. The concept of using word spectra with a series of graded adjectives has also been introduced, so that the words selected by the patient indicate varying degrees of symptom intensity. This synergy type includes the general ability to use various aspects of a symptom time series to aid in, or refine a, diagnosis.

As described earlier, the symptom and valuator objects can be programmed with functions that compute (or ask the patient for) various time-based statistics such as onset, offset, slope, trend, curvature, area, etc. At run time, when a script requires a time-based statistic for a given symptom, the symptom object invokes its valuator object to compute them. Such computed values then become separate symptom values that can be weighted and scored like any other symptom values. Using this synergy type, the symptom/valuator object becomes a smart process that does not just store symptom values, but that can perform dynamic, intelligent, internal analysis of how the symptom behaved over time in the patient, which generates useful diagnostic information in its own right.

The script author can distinguish or differentiate among candidate diseases based on when a symptom occurs in the patient, or on how the symptom varies over time in the patient. The author can use the actual symptom time variations to assign extra diagnostic weights to a disease.

One of the key features of the LB method is that it can use the time when symptoms occur and change to help diagnose the patient. This outperforms many other automated diagnostic methods.

4. Onset/Offset Analysis Synergy

In one embodiment of the invention, onset/offset analysis synergy adds extra diagnostic weight to a disease if a given symptom exhibits onset and/or offset in a specific manner. The type of onset and offset of a symptom can convey great diagnostic information. The following description is for onset analysis synergy; a similar description applies to offset analysis synergy.

At design time, the script author specifies for each disease:

(1) that a given symptom's onset is to be synergy weighted, (2) the onset types that can be used to select added synergy weight, (3) the synergy weights to be added depending on the onset type.

At run time, in the phase where the system is adding synergy weights to candidate diseases, the system:

(1) detects that a given symptom's onset is to be synergy weighted, (2) obtains the actual onset type for the symptom, (3) compares the actual onset type to the pre-defined type, (4) selects the onset synergy weight that corresponds to the actual type, (5) adds the selected onset synergy weight to the disease score.

Two examples of this synergy are as follows: 1) the sinusoidal relationship of severity of pain in colic, 2) the "stuttering" start of unstable angina.

5. Onset/Offset Slope Synergy

In one embodiment of the invention, onset/offset slope synergy adds extra diagnostic weight to a disease if a given symptom begins and rises to a maximum in a defined manner. The following description is for onset synergy; a similar description applies to the manner in which a symptom ends, or its offset.

At design time, the script author specifies for each disease:

(1) that a given symptom's onset is to be synergy weighted, (2) the onset slope threshold(s) to be used for selecting the synergy weight, (3) the synergy weights to be added depending on the magnitude of the onset slope.

At run time, in the phase where the system is adding synergy weights to candidate diseases, the system:

(1) detects that a given symptom's onset is to be synergy weighted, (2) obtains the actual onset slope for the symptom, (3) compares the actual onset slope to the pre-defined slope threshold(s), (4) selects the onset synergy weight that corresponds to the actual slope, (5) adds the selected onset synergy weight to the disease score.

The nature of the onset (and offset) of a symptom can convey great diagnostic information. For example, a headache that starts suddenly and is very severe has more chance of being a sub-arachnoid hemorrhage than a severe headache that comes on gradually. In vascular events such as a myocardial infarction, the onset of pain is very sudden, that is, the slope of a line plotting severity versus time will be nearly vertical. The sudden onset of vomiting and diarrhea in Staph food poisoning contrasts to other causes of gastroenteritis and food poisoning.

6. Onset/Offset Trend Synergy

In one embodiment of the invention, the onset (or offset) "trend" of a symptom refers to whether the symptom curve at that time point is linear or exponential, i.e., rising (or falling) at a constant rate or at an increasing or decreasing rate. This is referred to as "linear or exponential". The following description is for onset trend synergy; a similar description applies to the manner in which a symptom ends, or its offset.

At design time, the author specifies for each disease:

(1) that a given symptom's onset's curve trend is to be synergy weighted, (2) the onset trend threshold(s) to be used for selecting the synergy weight, (3) the synergy weights to be added depending on the trend of the onset slope.

At run time, in the phase where the system is adding synergy weights to candidate diseases, the system:

(1) detects that a given symptom's onset trend is to be synergy weighted, (2) obtains the actual onset trend for the symptom, (3) compares the actual onset trend to the pre-defined trend threshold(s), (4) selects the onset synergy weight that corresponds to the actual trend, (5) adds the selected onset synergy weight to the disease score.

The shape of the onset (and offset) curve of a symptom can convey diagnostic information. In one embodiment, the diagnostic system uses a Runge-Kutta curve-fitting algorithm to identify the type of curve under consideration. Other algorithms are used in other embodiments.

7. Onset/Offset Symmetry Synergy

In one embodiment of the invention, onset/offset symmetry synergy assigns extra diagnostic weight if the onset and offset curves (or slope if the relationship is linear) of a given symptom exhibit defined symmetry characteristics.

At design time, the script author specifies for each disease:

(1) that a given symptom's onset and offsets are to be weighted for symmetry, (2) the parameters that define various symmetry relationships, (3) the synergy weights to be added for a given symmetry relationship.

At run time, in the phase where the system is adding synergy weights to candidate diseases, the system:

(1) detects that a given symptom's onset/offset symmetry is to be synergy weighted, (2) obtains the actual onset and offset slopes and trends for the symptom, (3) converts the actual slopes and trends into pre-defined symmetry parameters, (4) selects the symmetry synergy weight that corresponds to the actual data, (5) adds the selected weight to the disease score.

Onset and offset symmetry is important in making several diagnoses. For example, when a patient has a kidney stone that passes into the ureter (the tube connecting the kidney to the bladder), the patient experiences the sudden onset of very severe (and colicky) pain. In addition, when the stone passes into the bladder, the pain symptom frequently disappears as suddenly as it came on.

8. First Significant Symptom (FSS) Synergy

In one embodiment of the invention, first significant symptom (FSS) synergy assigns extra diagnostic weight to a disease if the patient's FSS matches a list of possible FSSs for the disease. This synergy reflects the script author's real-world experience as to which symptoms tend to be the first ones noticed by a patient.

At scripting time, a disease script author creates a special list of symptoms that a patient might notice first, and associates a weight with each symptom. For example, for Appendicitis:

| | |
|---|---|
| Anorexia | 50 |
| Nausea | 30 |
| Epigastric Pain | 10 |

At run time, if the patient reports that Nausea was the first symptom she or he noticed, the system will add 30 diagnostic points to the diagnosis of Appendicitis (and similarly add some weight to all other diseases that show Nausea in their FSS tables).

The key is that we use the information that the patient has a specific symptom first to advance those diagnoses that match the patient. We already added points to the disease for just having this symptom; now we add extra weight for it being first. That's the meaning of FSS synergy.

9. Simultaneous Synergy

In one embodiment of the invention, simultaneous synergy assigns extra diagnostic weight to a candidate disease if two or more of its symptoms are present in the patient over a given time period.

At design time, for each disease, the script author can define any number of special symptom combinations as well as an associated diagnostic weight that should be added to the disease score if the combination is present. The disease author may use a Gantt chart to appreciate the simultaneous, sequential and overlapping synergies.

At run time, for each disease, the system:

(1) tracks the symptoms actually present in the patient, (2) determines if any pre-defined symptom combination is present, and—if so—

(3) adds the associated weight to the score of the disease.

Simultaneous Synergy can be used very effectively by a script author to describe a disease in terms of syndrome, and to characterize how various syndromes contribute to the disease.

10. Sequencing Synergy

In one embodiment of the invention, sequencing synergy assigns extra diagnostic weight to a candidate disease if two or more of its symptoms are present in the patient in a specific time sequence.

At design time, for each disease, the Script author may define any number of special symptom sequences, with associated diagnostic weights to be added to the disease score if the patient exhibits the symptoms in the specified order.

At run time, for each disease, the system:

(1) establishes an absolute start time for every symptom, (2) tracks the symptoms actually present in the patient, (3) detects if any author-defined sequence is present, (4) determines whether the symptoms are present in the pre-defined time order, (5) if appropriate, adds the sequence weight to the score of the disease.

11. Overlapping Synergy

In one embodiment of the invention, overlapping synergy assigns extra diagnostic weight to a candidate disease if two or more of its symptoms are present in the patient at the same time for a specified amount of time.

At design time, for each disease, the author can define any number of special overlap symptom combinations, an overlap threshold, and a diagnostic weight that should be added to the disease score if the symptom combinations overlapped in time for at least the specified threshold time.

At run time, for each disease, the system:

(1) tracks the symptoms actually present in the patient, (2) detects if any author-defined overlapping symptoms are present, (3) computes for how long the symptoms overlapped in time, (4) checks if the actual overlap meets or exceeds the specified overlap threshold, (5) if applicable, adds the specified overlap weight to the score of the disease.

12. Integral (Area) Synergy

In one embodiment of the invention, integral synergy assigns extra diagnostic weight for the total amount of a symptom over a specified time period. At design time, the author assigns diagnostic weight for the amount of a symptom that a patient has reported over a time interval. At run time, the system (1) tracks the time chart of the symptom values, (2) computes the total symptom value (i.e., integrates the symptom curve) between two time points, and (3) if appropriate, adds an area synergy weight to the disease score.

The amount of a symptom over time gives information regarding biological and chemical body functions and reactions, which, in turn, have diagnostic value. An example is the amount of pain a patient has suffered between two points in time. The integral synergy weight helps the system automatically recognize those patients that can benefit from strong analgesics, for example. In addition to diagnosis, this synergy could also be used for pain management. It could identify those patients who perhaps cannot, or do not, identify themselves as needing narcotic analgesics.

V. Descriptions of the Drawings

The software described by the following drawings is executed on a structure-based engine of a medical diagnostic and treatment advice system such as described in Applicant's U.S. Pat. No. 5,935,060. One embodiment of a structure-based engine is the list-based engine, but other embodiments may be implemented.

Referring now to FIG. 1, one embodiment of a diagnostic loop portion 100 of a medical diagnostic and treatment advice (MDATA) system, that may include a List-Based Engine (LBE), will be described in terms of its major processing functions. Note that treatment advice may be optionally provided. However, the diagnostic aspect of this system is the main focus of the invention. Each function is further described with an associated figure.

When the system starts, it assumes that another, off-line data preparation program has prepared a suitable database of medical diagnostic data in the form of disease and symptom objects, DOs and SOs respectively, and has assigned diagnostic weights to specific symptom values for each disease, and to special combinations or sequences of symptom values (called "synergies"). When a patient (who may access the system via a data communications network such as the Internet) presents a medical complaint to the MDATA system to be diagnosed, the system first retrieves all of the relevant disease objects from its database and assembles them into a candidate disease list. The system then uses the diagnostic loop to develop a diagnostic profile of the candidate disease list.

Inside the diagnostic loop, the system selects a current disease and symptom to pursue. Then the system obtains the value of the symptom for the current patient, calculates the weights associated with that value, and updates the scores of all affected candidate diseases with the weights. The updated scores are then used to re-rank the diseases and to select the disease and symptom to be evaluated in the next iteration. In this manner, as the loop continues to iterate, the system builds up a diagnostic profile of the candidate diseases for the current patient. The loop can be interrupted at any point, and the then-current diagnostic profile examined in order to adjust the system parameters and continue the loop, or to terminate the loop, as desired. At the end of the loop, a diagnostic report is prepared that summarizes the actions taken and the results computed.

The diagnostic loop 100 begins at state 102, where prior processing is assumed to have established a chief complaint for the current patient and a diagnostic report needs to be determined. Moving to function 110, the system acquires the computer resources required for the diagnostic loop. In this function, the system acquires computer memory as needed, creates required software objects, and sets variables to their initial values based on the current options, limits, and diagnostic goals. The system also creates a list of diseases that are to be used as the initial candidates for diagnosis. Moving to function 120, the system selects one disease from the list of candidate diseases. This disease becomes the current focus disease, i.e., the disease for which a symptom is to be evaluated. Moving to function 130, the system selects one symptom from the list of symptoms associated with the current disease. This symptom becomes the current focus symptom to be evaluated in the patient. Moving to function 140, the system evaluates the current symptom in the patient by suitable means such as questioning the patient, using logical inferences, mathematical computations, table lookups, or statistical analysis involving other symptom values. Moving to function 150, the system updates all candidate diseases that use the current symptom with the new symptom value obtained in function 140. Moving to function 160, the system updates all working lists and records with new values, scores, and diagnoses. Moving to function 170, the system reviews the progress of the diagnosis to decide whether another iteration of the diagnostic loop is required. Proceeding to a decision state 172, the system tests whether the diagnostic loop is to be terminated e.g., by user direction. If not, the system moves to function 120 for another iteration; otherwise, the system moves to function 180, where the system saves appropriate values computed in the diagnostic loop and destroys all temporary data structures and objects required for the diagnostic loop. Continuing at state 182, the system returns a report of the diagnostic results.

Figure 2:
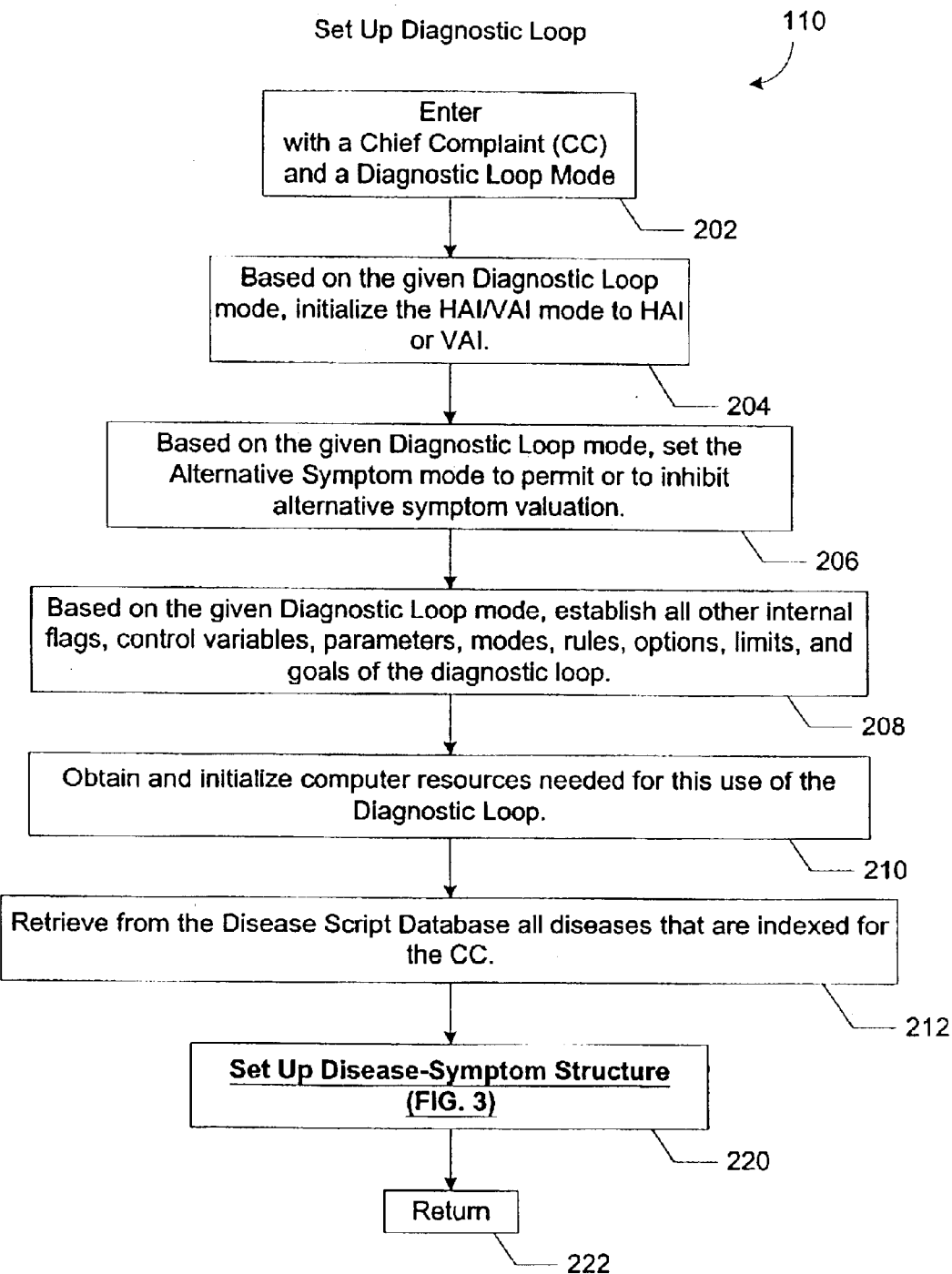
FIG. 2 is a flowchart of the Set Up Diagnostic Loop function shown in FIG. 1.

Referring now to FIG. 2, the Set-up Diagnostic Loop function 110 previously shown in FIG. 1 will be described. Function 110 acquires the computer resources and sets up the data structures needed for the diagnostic loop 100 (FIG. 1). The system is designed to be fully adaptive to its environment, and must initialize various memory structures to prepare for processing. In an object-based embodiment, this preparation includes the creation of various objects. Each object has an initialization function that allows the object to initialize itself as needed.

Function 110 begins with entry state 202, where a chief complaint and a diagnostic mode have been established by prior processing. The chief complaint will be used in state 212 to retrieve associated diseases. The diagnostic mode will be used throughout function 110 to control detail processing. Moving to state 204, function 110 initializes the HAI/VAI mode to either HAI or VAI, depending on the HAI/VAI mode desired for this operation of the diagnostic loop. In HAI mode, the system will consider all of the candidate diseases to select the next focus symptom; in VAI mode, the system will use only the list of symptoms of the current focus disease.

Moving to state 206, function 110 initializes the Alternative Symptom mode to either permit or inhibit alternative symptom valuation, depending on the Alternative Symptom mode desired for this operation of the diagnostic loop. If alternative symptoms are permitted, the system will later accept alternative values in place of the specified symptom value. If alternative symptoms are inhibited, the system will later insist on evaluating the specified symptom. Moving to state 208, function 110 initializes other internal variables that support the loop processing such as control flags, option indicators, loop limits, and loop goals. The exact variable and value of each variable depends on the particular code embodiment chosen for the computer program. Moving to state 210, function 110 obtains and initializes special computer resources required for this operation of the diagnostic loop. The details of this initialization depend on the code embodiment chosen for the computer program. For example, if an object is used to represent the list of candidate diseases, state 210 creates and initializes an empty candidate disease object; but if a relational table is used to represent the list of candidate diseases, state 210 creates and initializes an empty table to contain the candidate diseases. Moving to state 212, function 110 retrieves from the disease database all those diseases that exhibit the chief complaint being diagnosed and (if available) the patient's symptom time profile (FIG. 28).

As part of the off-line data gathering and preparation process, every disease in the disease object database is associated with at least one chief complaint and with a time profile of symptoms. This association is used here to retrieve the list of diseases that constitute the initial candidate set. By "candidate" disease is meant any human disease, as yet unidentified, that has some probability of being the patient's illness, based on the symptoms and the chief complaint indicated by the patient. Moving to a function 220, various internal working structures required to efficiently perform such detailed processing as sorting, searching, and selecting subsets of diseases and symptoms are initialized. Function 220 is further described in conjunction with FIG. 3. Moving to state 222, function 110 returns control to the process that called it, in effect moving to function 120 of FIG. 1.

Figure 3:
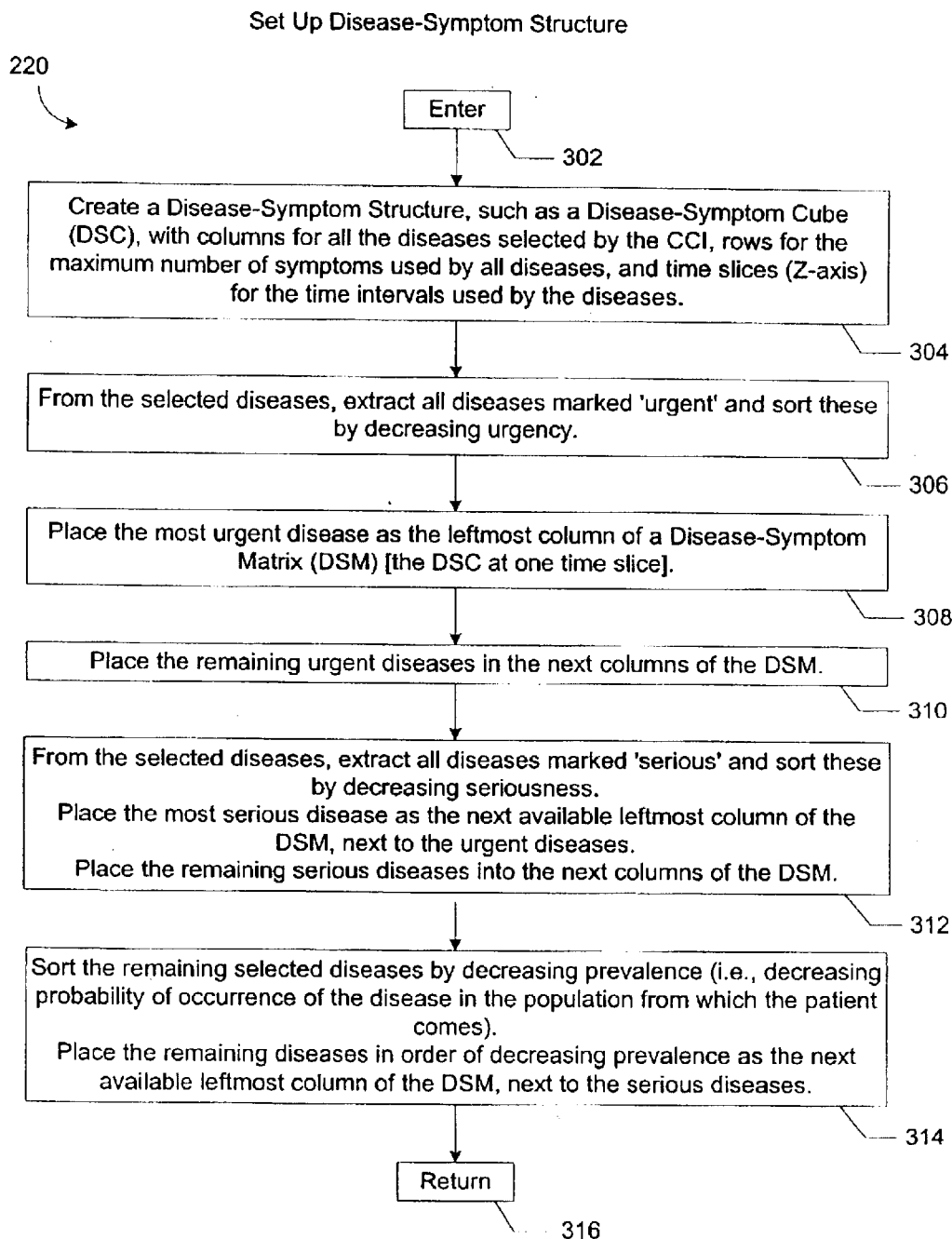
FIG. 3 is a flowchart of the Set Up Disease-Symptom Structure function shown in FIG. 2.

Referring now to FIG. 3, the Set-up Disease-Symptom Structure function 220, which sets up the candidate disease list and actual symptom data structures to be used in the diagnostic loop, will be described. The candidate disease list is generated and then partitioned into three sublists of urgent, serious, and common diseases. This separation allows the system to consider candidate diseases in order of urgency and seriousness before it considers the common diseases.

Function 220 begins with an entry state 302. Moving to state 304, function 220 creates a disease-symptom matrix (DSM), which is a data structure with columns for all the diseases selected by the chief complaint, rows for the maximum number of symptoms used by all candidate diseases, and time slices (Z-axis) for the time intervals used by the diseases. Other disease-symptom structures may be used in other embodiments. Moving to state 306, function 220 extracts all diseases marked 'urgent' from the candidate diseases and sorts these by decreasing urgency. Moving to state 308, function 220 places the most urgent disease as the leftmost column of a Disease-Symptom Matrix (DSM) [which can be considered one time slice of a Disease-Symptom Cube (DSC)]. Moving to state 310, function 220 places the remaining urgent diseases in the next columns of the DSM. Moving to state 312, function 220 extracts all diseases marked 'serious' from the candidate disease list; sorts these serious diseases by decreasing seriousness; places the most serious disease as the next available leftmost column of the DSM, next to the urgent diseases; and places the remaining serious diseases into the next columns of the DSM. Moving to state 314, function 220 sorts the candidate diseases that remain after the urgent and serious diseases were removed by decreasing prevalence, i.e., the probability of occurrence of the disease in the population from which the patient comes, and places the remaining diseases in order of decreasing prevalence as the next available leftmost column of the DSM, next to the serious diseases. Moving to state 316, function 220 returns control to the process that called it, in effect to state 222 of FIG. 2.

Figure 4:
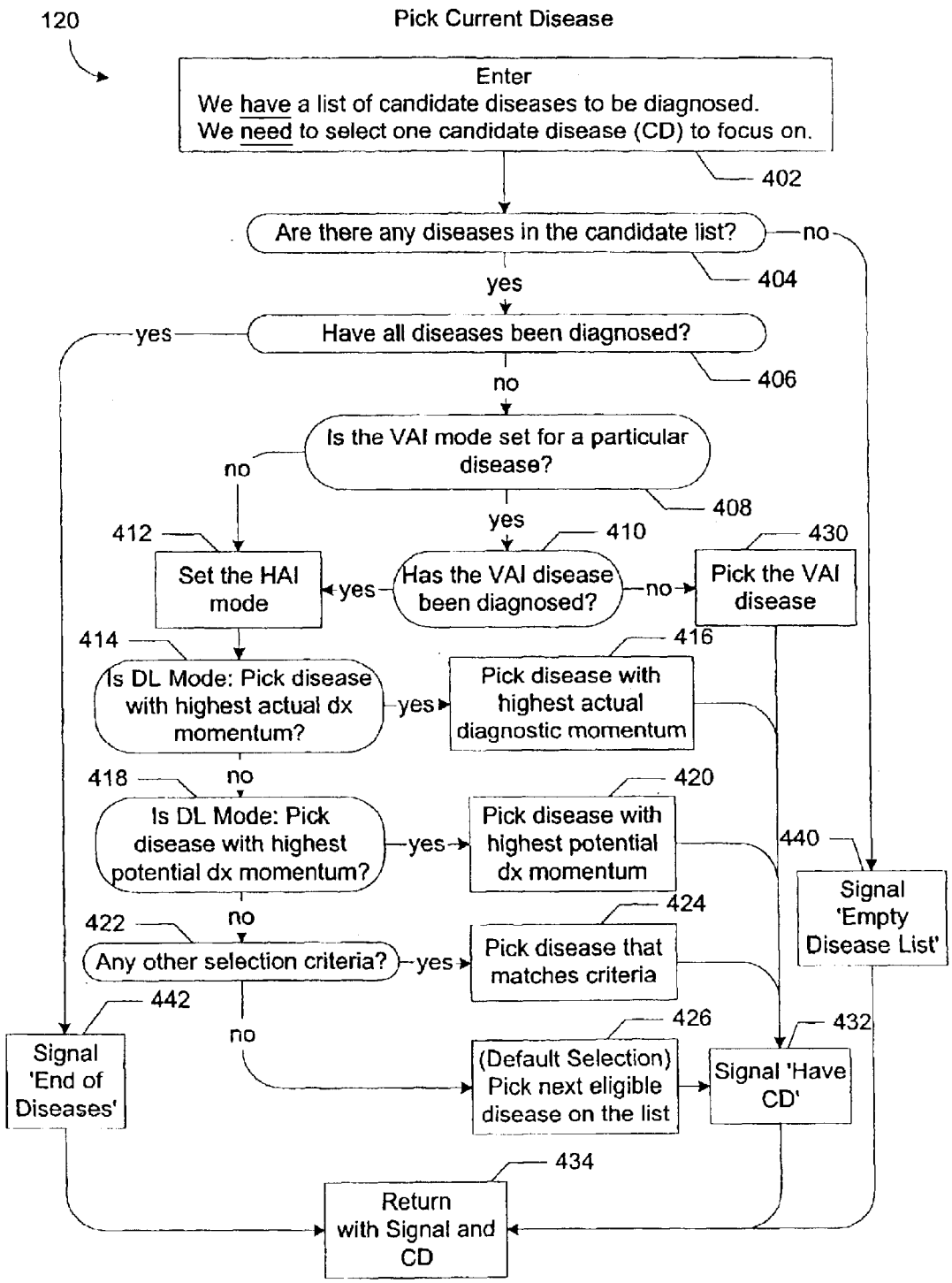
FIG. 4 is a flowchart of the Pick Current Disease function shown in FIG. 1.

Referring now to FIG. 4, the Pick Current Disease function 120, in which the candidate disease list is searched to select one disease as the current focus disease, will be described. The selection criteria can be any computation that can identify diseases with high potential for being the actual disease of the patient, such as selecting diseases based on their performance so far in the current diagnostic session, on high diagnostic score, high rate of change of score (diagnostic momentum), number of positive responses to questions, or best statistical match of disease timelines, which may happen in the HAI mode. In another selection mode (VAI), an external user or process has already selected the focus disease, so that the system has no choice.

Function 120 begins with the entry state 402, where a list of diseases exists that are candidates for diagnosis. Function 120 selects one of these candidate diseases to become the current focus disease. The selection can be made using one of many rules; which rule is used depends on the diagnostic mode. FIG. 4 shows two rules being tested, but any number of rules can be added. Moving to a decision state 404, function 120 first checks whether the candidate disease list is empty. If so, there are no more diseases to examine, and function 120 moves to state 440. At state 440, function 120 sets an outcome signal to indicate that no current disease has been selected and then moves to state 434, where the process returns. If the candidate list is not empty at decision state 404, then there is at least one candidate disease remaining and function 120 moves to a decision state 406 to test whether all candidate diseases have been processed. If so, function 120 moves to state 442, where it sets an outcome signal to that effect and moves to state 434 to return control. However, if, at decision state 406, some diseases remain to be processed, function 120 moves to a decision state 408. At decision state 408, if the selection mode is set to VAI, i.e., forced to use a specific disease, function 120 moves to a decision state 410, otherwise to state 412. At state 410, if the VAI disease has not yet been diagnosed, function 120 moves to state 430, selects the VAI disease as the current disease and moves to state 432. But if, at decision state 410, if the disease that was pre-selected has already been diagnosed, function 120 moves to state 412, to reset processing to the HAI mode.

With state 414 begin the states of actually selecting a disease. The diagnostic mode that is in effect when the diagnostic loop starts specifies or implies a disease selection rule or criterion. This rule is based on either the actual diagnostic progress so far, or the potential progress that could be made, using such diagnostic measures as weighting, momentum, score, and probability. This selection rule can be changed by internal processing or external request, but some selection rule will always be in effect. Function 120 uses the rule to select one of the candidate diseases as focus disease. Moving to a decision state 414, if the selection rule is to select the candidate disease with the highest actual diagnostic momentum, function 120 continues to state 416. At state 416, function 120 selects the candidate disease with the highest current diagnostic momentum and then moves to state 432. But if, at decision state 414, the current rule is otherwise, function 120 moves to a decision state 418.

At decision state 418, if the selection criterion is to select the candidate disease with the highest potential diagnostic momentum, function 120 moves to state 420, selects the candidate disease with the highest potential diagnostic momentum and then moves to state 432. But if, at decision state 418, the current diagnostic mode is otherwise, function 120 moves to a decision state 422. At decision state 422, if the diagnostic mode is to select the candidate disease using some other criterion such as time profile matching or direct patient input, function 120 moves to state 424, which uses some other criterion in a similar manner to select the disease and then moves to state 432. But if, at decision state 422, there are no more criteria to be used, function 120 moves to state 426, applies the default rule that may simply select the next eligible candidate disease and then moves to state 432. At state 432, function 120 sets an outcome signal to indicate that a current focus disease has been selected and then function moves to state 434 to return the outcome signal and the current disease identifier to the process that called function 120, in effect to function 130 of FIG. 1.

Figure 5:
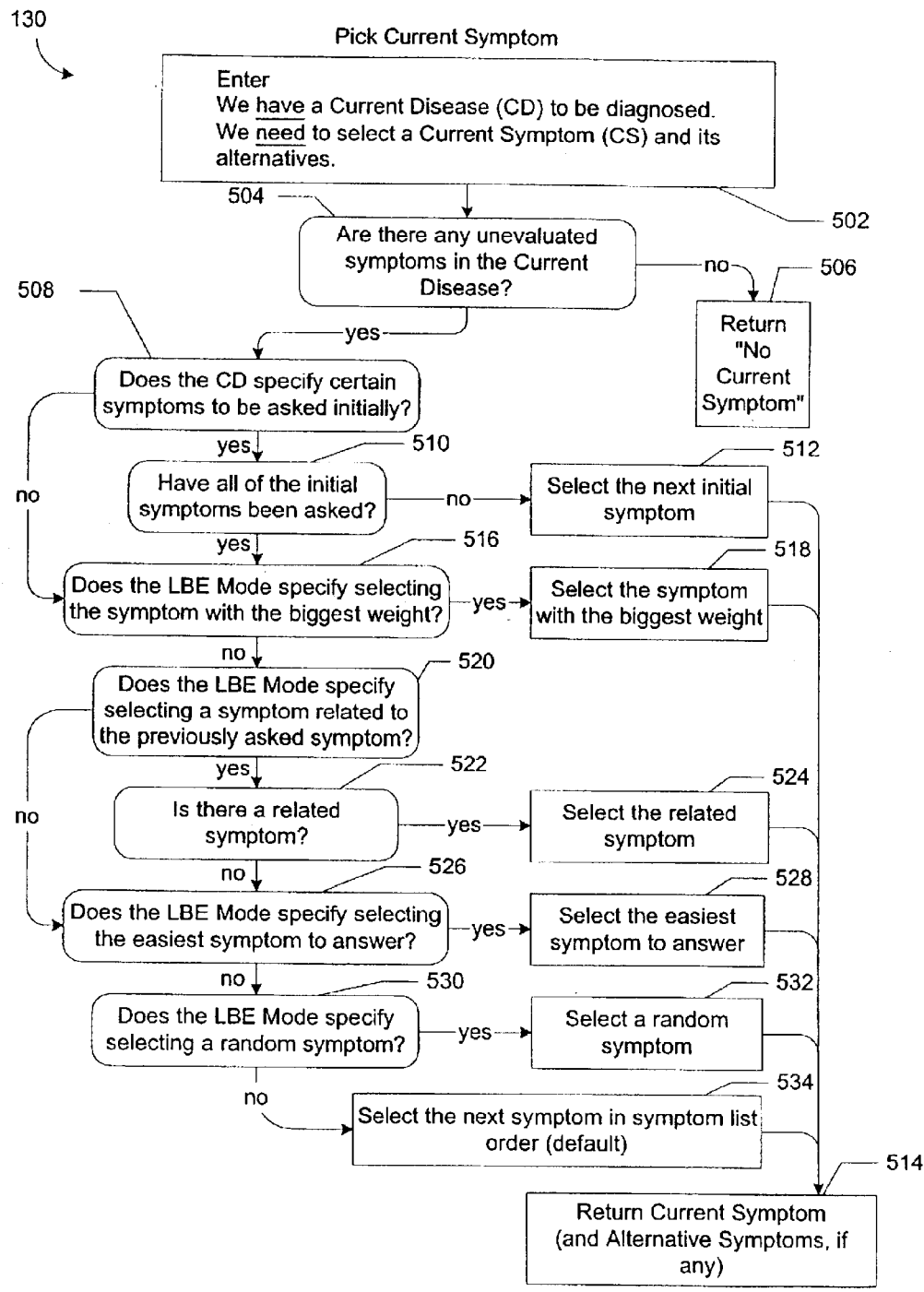
FIG. 5 is a flowchart of the Pick Current Symptom function shown in FIG. 1.

Referring now to FIG. 5, the Pick Current Symptom function 130, which selects a symptom of the current focus disease to become the next current focus symptom, will be described. Here, the system examines the list of symptoms of the current focus disease and uses various criteria to select one of them as the next focus symptom. The goal is to select a symptom that will advance the diagnostic score with the least system or patient effort, which can be achieved in a number of ways such as by selecting a symptom for which the value has already been obtained by another disease, or a symptom that has been specially identified by the author, or a symptom with high diagnostic weight, or one that is likely to rule the disease in or out at once, or symptoms that have high commonality across diseases. Once function 130 has selected a symptom in this manner, it will also select all symptoms that have been identified as acceptable alternatives by the author.

Function 130 begins with the entry state 502, where a current focus disease has been selected and the function must now select from that disease's symptom list a current focus symptom, plus possibly one or more alternative symptoms, if any were specified by the author. The symptom can be selected using one of many rules. Which rule is used depends on the diagnostic mode. Moving to a decision state 504, function 130 first checks whether there are any symptoms remaining in the current disease that have not yet been evaluated for the current patient. If so, function 130 moves to state 506, which returns an outcome signal that indicates that no current symptom has been selected. But if, at decision state 504, there is at least one eligible symptom, function 130 moves to a decision state 508.

Decision state 508 begins the actual selection of a symptom. The diagnostic mode that is in effect when the diagnostic loop starts can specify or imply one of many symptom selection rules or criteria, which can be changed by internal processing or external request. However, in one embodiment, some symptom selection rule will always be in effect. In addition, for any given symptom, a disease can identify one or more alternative symptoms that can be used in its place. The focus symptom returned by state 130 can thus consist of a symptom package that contains at least one symptom plus zero or more alternative symptoms. At decision state 508, function 130 tests whether the disease has symptoms that must be evaluated before other symptoms of that disease. Such symptoms serve to quickly eliminate a disease that does not meet basic criteria. If the disease has such initializing symptoms, function 130 moves to a decision state 510. At decision state 510, if all of the initial symptoms have been evaluated, function 130 moves to a decision state 516. But if, at decision state 510, there are any unevaluated initial symptoms, function 130 moves to state 512, selects the next initial symptom as focus symptom and moves to return state 514. Moving to decision state 516, if the current diagnostic mode specifies selecting symptoms with the largest diagnostic weight, function 130 moves to state 518, selects the symptom with the largest diagnostic weight and moves to return state 514. But if, at decision state 516, the rule is not to select the symptom with the largest weight, function 130 moves to a decision state 520. At decision state 520, function 130 accommodates symptoms that are related to each other in some way such as groups, combinations, or sequences. If the current diagnostic mode indicates that related symptoms are to be considered, function 130 moves to state 522, but if related symptoms are not to be considered, function 130 moves to state 526.

At decision state 522, if there is a symptom related to the previously evaluated symptom, function 130 moves to state 524. At state 524, function 130 selects a symptom that is related to the previously evaluated symptom and moves to return state 514. But if, at decision state 522, there is no related symptom, function 130 moves to state 526. At decision state 526, if the current diagnostic mode indicates that symptoms are to be considered that are easiest to evaluate, function 130 moves to state 528, selects the next symptom that is easiest to evaluate and then moves to return state 514. But if, at decision state 526, the rule is not to select the easiest symptom, function 130 moves to a decision state

530. At decision state 530, if the current diagnostic mode indicates that symptoms are to be selected at random, function 130 moves to state 532, selects the next symptom at random from the current disease's symptom list and then moves to return state 514. But if, at decision state 530, the rule is not to select a random symptom, function 130 moves to state 534, selects the next eligible symptom from the current disease's symptom list and then moves to return state 514. At state 514, function 130 returns the current focus symptom (and all alternative symptoms, if any) to the process that called function 130, in effect to function 140 of FIG. 1.

Figure 6:
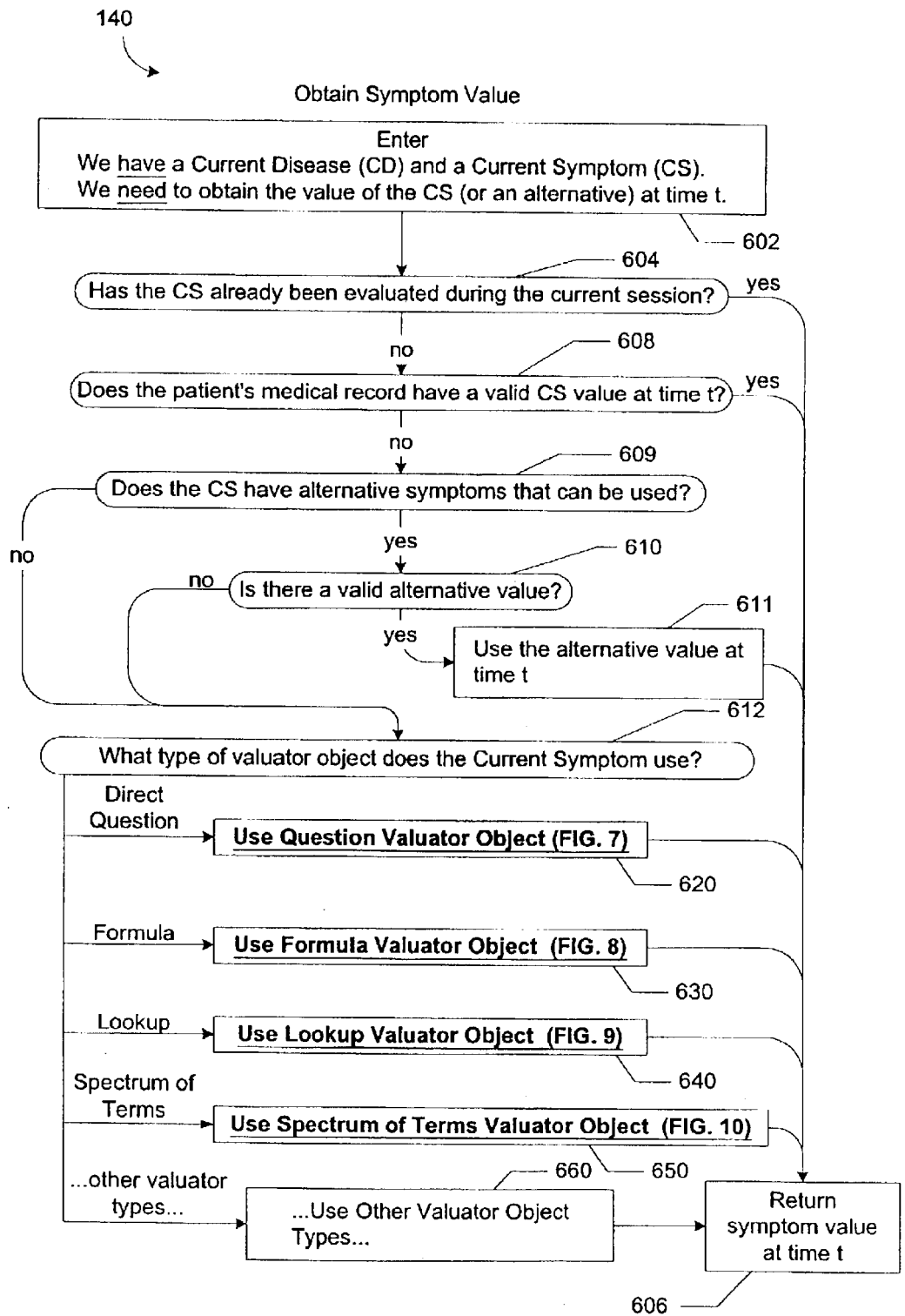
FIG. 6 is a flowchart of the Obtain Symptom Value function shown in FIG. 1.

Referring now to FIG. 6, the Obtain Symptom Value function 140, which evaluates the current focus symptom, i.e., establishes a specific value that occurred or existed at some time t in the patient, will be described. At this point in the diagnostic loop, the system has selected a current focus symptom and must now determine its value at some time t in the on-line patient. Symptom values can be simple (e.g., patient is a smoker) or detailed (e.g., patient has a 12-year, 2-packs/day smoking history); values can be simple numbers or symbols, or complex graphics, photos, or disease timelines (see, for example, FIG. 28).

Function 140 must now select either the current symptom or one of its alternatives, and then obtain its value in the patient at specific times. If the current diagnostic mode permits the use of alternative symptoms, and the current focus symptom has an alternative symptom that has already been evaluated, then the value of that alternative symptom is used at once, without further evaluation. The time saved by this evaluation shortcut is the basic reason for the use of alternative symptoms.

How the value itself is obtained depends on the symptom being evaluated and can use many different methods such as reviewing the patient's medical record, asking the on-line patient direct questions, drawing logical inferences from other symptom values, using mathematical and statistical formulas, using specially prepared lookup tables, even having the patient perform self-examinations. These different evaluation techniques are described here collectively as a 'valuator function'.

Function 140 begins with the entry state 602, where a current focus disease and symptom have been selected by prior processing. Moving to a decision state 604, function 140 first checks whether an acceptable value was already obtained during this session, perhaps by some other disease or some acceptable alternative symptom. If the current focus symptom already has a value, function 140 moves to state 606 to return that value; otherwise, function 140 moves to a decision state 608. At decision state 608, function 140 checks whether the current symptom already has a value in the patient's medical record. If so, function 140 moves to state 606 to return that value; otherwise, function 140 moves to a decision state 609. At decision state 609, if the current symptom has alternative symptoms and the mode permits their use, function 140 moves to a decision state 610; otherwise function 140 moves to a decision state 612. At decision state 610, if the current symptom has an acceptable alternative symptom value then function 140 skips further evaluation and returns the alternative value at time t from state 611 at once at state 606; otherwise function 140 moves to decision state 612.

At decision 612, function 140 begins the process of evaluating the current symptom by determining the valuator type of the current symptom. If the valuator type is a direct question, function 140 moves to function 620 to ask questions of the on-line patient, which is described in FIG. 7 and then moves to state 606. But if, at decision state 612, the valuator type is a mathematical formula, function 140 moves to function 630 for evaluating the formula (described in FIG. 8) and then moves to state 606. But if, at decision state 612, the valuator type is a table lookup, function 140 moves to function 640 to look up the value in a table (described in FIG. 9), and then moves to state 606. But if, at decision state 612, the symptom value is based on analyzing a spectrum of terms, function 140 moves to function 650 to perform the spectrum of terms analysis and obtain a value, which is described in FIG. 9. Then function 140 moves to state 606. Finally, if at decision state 612 the valuator is of some other type, such as disease time profile matching (FIG. 28), function 140 moves to state 660 to invoke that valuator and obtain a value in a similar manner. Then function 140 moves to state 606 to return the current symptom and its value at some time t to the calling process that invoked function 140, in effect to function 150 of FIG. 1.

Figure 7:
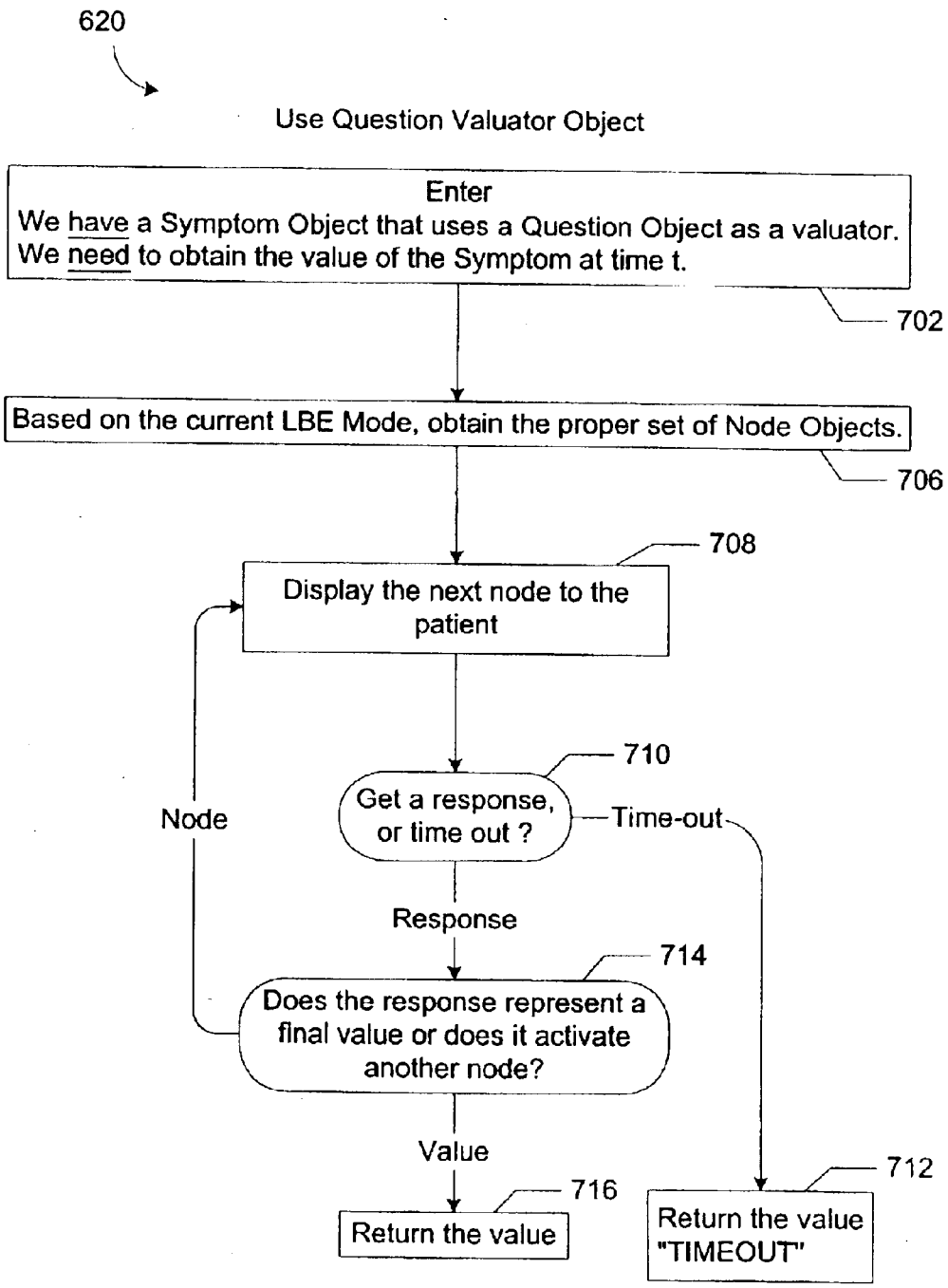
FIG. 7 is a flowchart of the Use Question Valuator Object function shown in FIG. 6.

Referring now to FIG. 7, the Question Valuator function 620, which is part of a question valuator object, will be described. A question valuator object obtains a symptom value at time t by asking an on-line patient one or more questions. To ask the questions, it uses one or more node objects that are pre-programmed by the script author to communicate with the patient in some natural language, using appropriate instructions, definitions, explanations, questions, and response choices. The response selected by the patient is encoded as a symptom value and ultimately returned to the caller of function 620.

Function 620 begins with entry state 702, where the current focus disease, symptom, and question objects have been established by prior processing and are given to the function. Function 620 now questions the on-line patient to obtain a value for the symptom at some time t. Moving to state 706, function 620 retrieves, from a database of node objects, a set of nodes listed in the current valuator object. Moving to state 708, function 620 displays the next node, which includes instructions and a question, to the patient. Moving to a decision state 710, if there is no response within a prescribed time, function 620 moves to return state 712 and returns a signal that the question object has timed out. But if, at decision state 710, function 620 obtains a response from the patient, the function moves to a decision state 714. At decision state 714, function 620 determines whether the response is a final symptom value or a signal to activate another node. If the response activates another node, function 620 moves back to state 708, which repeats the sequence of question and response states with a different node. Over time, the effect of this sequence is to generate a dialog with the patient that culminates in a symptom value being generated at state 714. When, at decision state 714, the patient's response is a value, function 620 moves to state 716 and returns the value obtained from the patient.

Figure 8A:
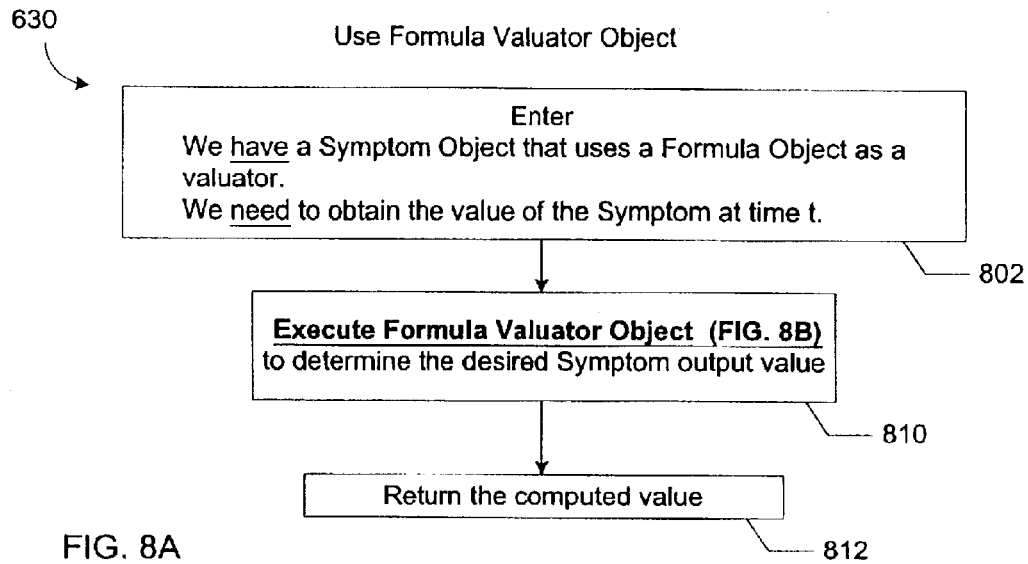
FIG. 8 is a flowchart of the Use Formula Valuator Object function shown in FIG. 6.

Referring now to FIG. 8*a*, the Formula Valuator function 630, which is part of a formula valuator object, will be described. A formula valuator object computes the value of a symptom at some time t by evaluating a given formula. In the object-based embodiment, each formula is embedded in a different formula valuator object, and there are as many different formula valuator objects in the system as there are formulas. Any other object that needs to evaluate a formula can call the appropriate formula valuator. A simple example is to convert an absolute date such as Dec. 7, 1941 into an age in years at some later time t.

Function 630 begins with entry state 802, where current focus disease, symptom, and valuator objects have been selected by prior processing. Function 630 now evaluates the formula to obtain a value for the symptom. Moving to function 810, the formula calculator object is invoked. Moving to state 812, function 630 returns the computed value.

Figure 8B:
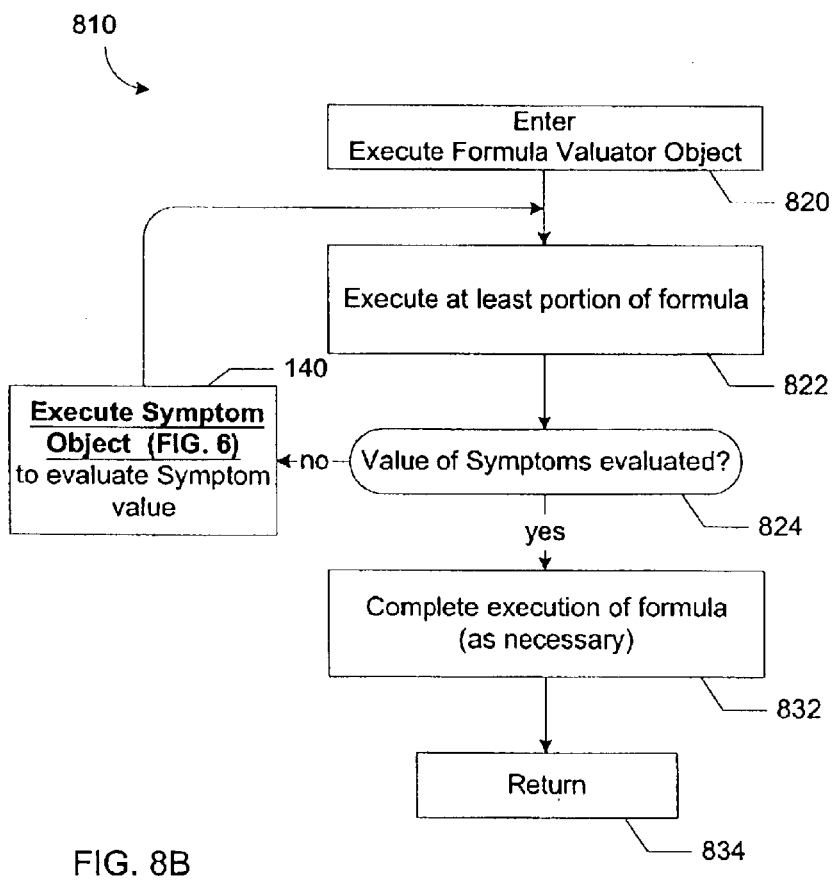

Referring now to FIG. 8b, the Execute Formula Valuator function 810, which evaluates a given formula that may use other symptom values to compute a symptom value at time t. The formula is given to function 810 as a set of suitably encoded operations and operands in some formalized system of mathematics such as arithmetic, geometry, trigonometry, algebra, calculus, probability, or statistics. Function 810 performs the required operations and returns the computed value. One special sub-processing case occurs when an operand of the formula is itself a symptom that still needs to be evaluated, in which case function 810 interrupts the evaluation, causes the operand symptom to be evaluated, and then continues the evaluation of the formula. This is a potentially recursive process, since the evaluation of a symptom can itself involve the evaluation of a different formula. By using this design, any structure of nested formulas, using any symptom objects can be specified by a script author and evaluated when needed.

Function 810 begins with the entry state 820, where the formula and its arguments are known. Moving to state 822, the formula is evaluated as far as is possible with the given arguments. In some cases, this will completely evaluate the formula; in others, it will encounter an argument that is itself a symptom that still needs to be evaluated. Moving to a decision state 824, if an argument requires further evaluation, function 810 moves to the Execute Symptom Object function 140; otherwise it moves to state 832. At function 140, the argument symptom is evaluated by calling the appropriate symptom object (FIG. 6); then function 810 moves back to state 822 to continue evaluating the formula. At state 832, function 810 continues to evaluate the formula until the final value has been computed. Moving to state 834, the final value is returned.

Figure 9:
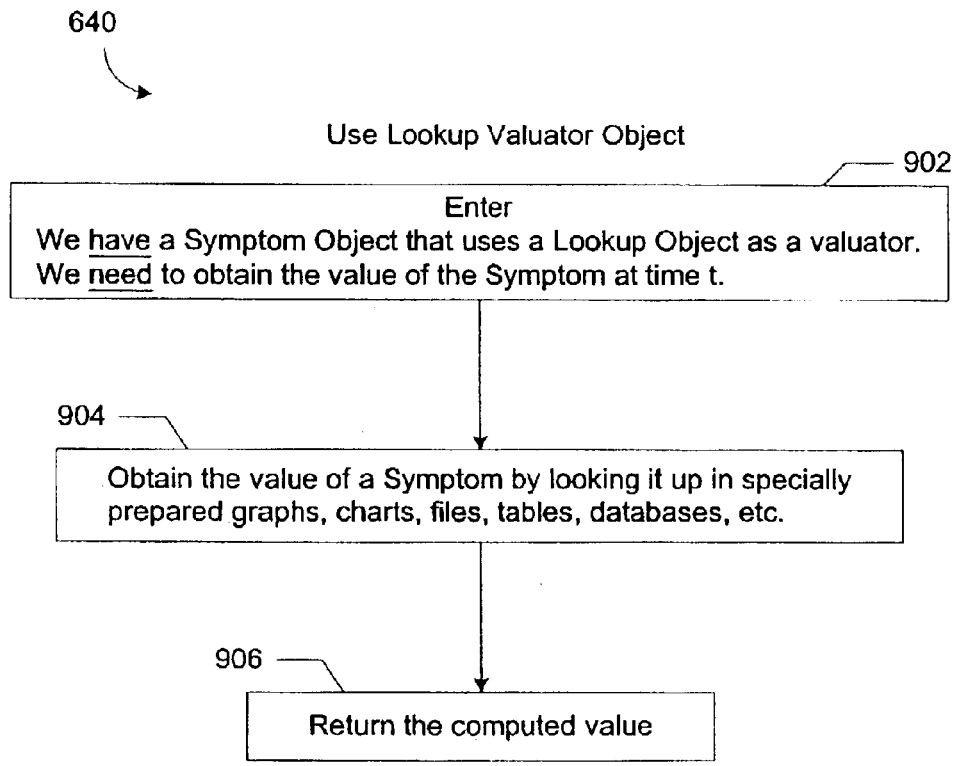
FIG. 9 is a flowchart of the Use Lookup Valuator Object function shown in FIG. 6.

Referring now to FIG. 9, the Lookup Valuator function 640, which is part of a lookup valuator object, will be described. A lookup valuator object computes the value at time t of a symptom by looking it up in a table or chart. It is often the case that the value of a symptom is known to the system indirectly, perhaps from some other context in which a chart or table was prepared. One simple example is a time-based temperature chart that can be used to retrieve the value of fever at time t. Alternatively, function 640 could use statistical computations based on a chart, such as counting certain occurrences, finding the area under a disease timeline between two given times, or matching disease timelines.

Function 640 begins with entry state 902, where a symptom has been selected for evaluation. Moving to state 904, the symptom is looked up in a prepared lookup medium such as a graph, chart, or database table. Moving to state 906, function 640 returns the value to the process that called function 640.

Figure 10:
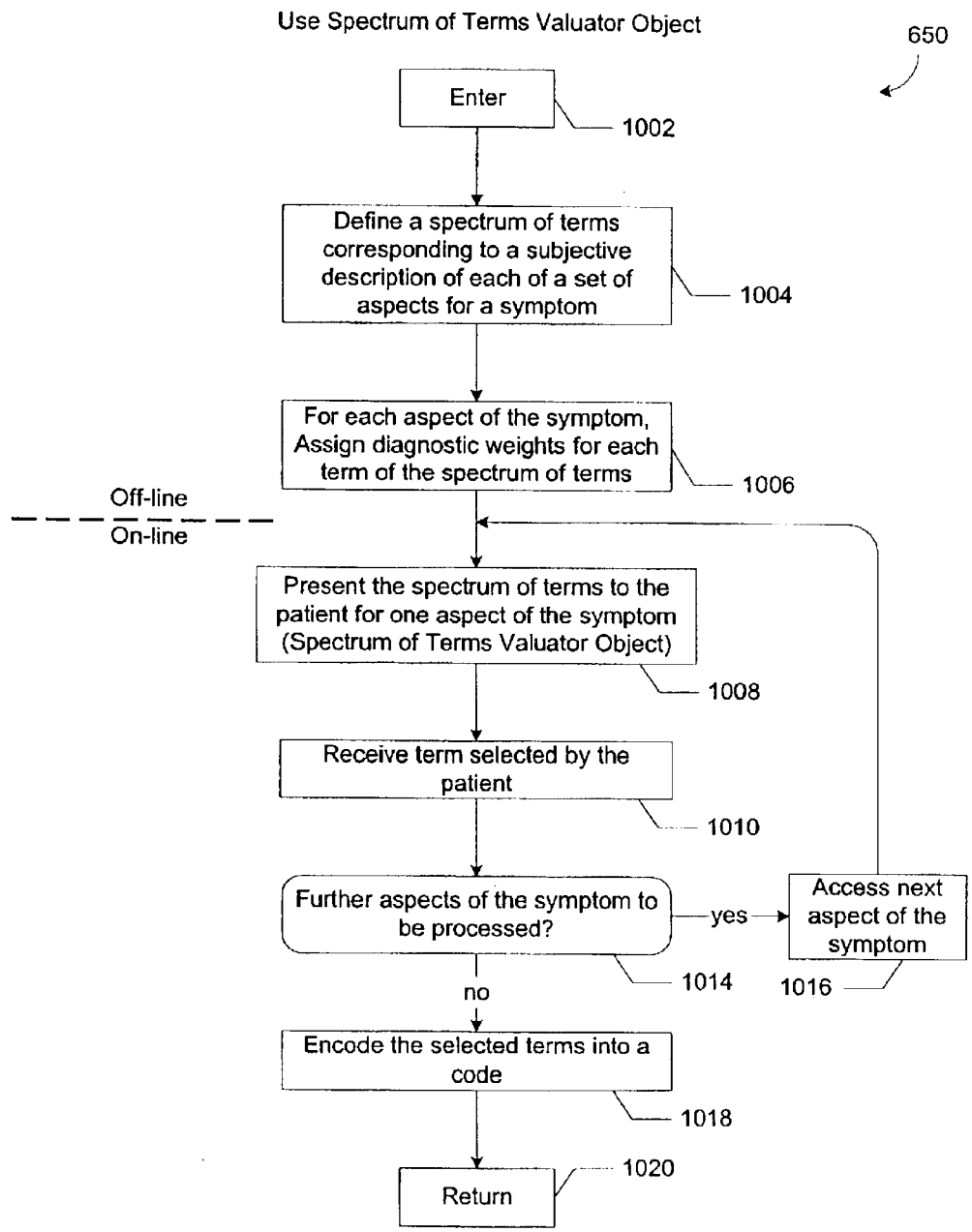
FIG. 10 is a flowchart of the Use Spectrum of Terms Valuator Object function shown in FIG. 6.

Referring now to FIG. 10, the Spectrum of Terms Valuator function 650, which is used for symptoms that depend on the patient's subjective description, will be described. Function 650 converts a patient's subjective description of a symptom at time t into a specially encoded token that is returned by the function and processed by the system like any other value. Function 650 provides a list of key descriptor words to the patient, lets the patient select one or more words, and encodes the selected words into a token that is returned.

States 1004 and 1006 of the figure show that the spectrum of descriptor terms is prepared, and weights are assigned to the various terms in an off-line preparation process of the symptom object. These data are typically prepared and stored in a database that is accessed during on-line diagnosis.

In the on-line diagnostic system, function 650 begins at state 1008, where the function presents the spectrum of terms to the patient in some manner that allows the patient to select a set of descriptive terms for time t. Moving to state 1010, function 650 obtains and processes the term(s) selected by the patient. Moving to a decision state 1014, if other aspects of the symptom are to be processed, function 650 moves to state 1016; otherwise the function moves to state 1018. At state 1016, function 650 prepares to process the next aspect of the symptom's term spectrum and then moves back to state 1008. At state 1018, function 650 collects and saves the terms collected for time t into a suitable code that can be returned as a value. Moving to state 1020, function 650 encodes the terms collected from the patient and returns them as the value to the process that called function 650.

Figure 11:
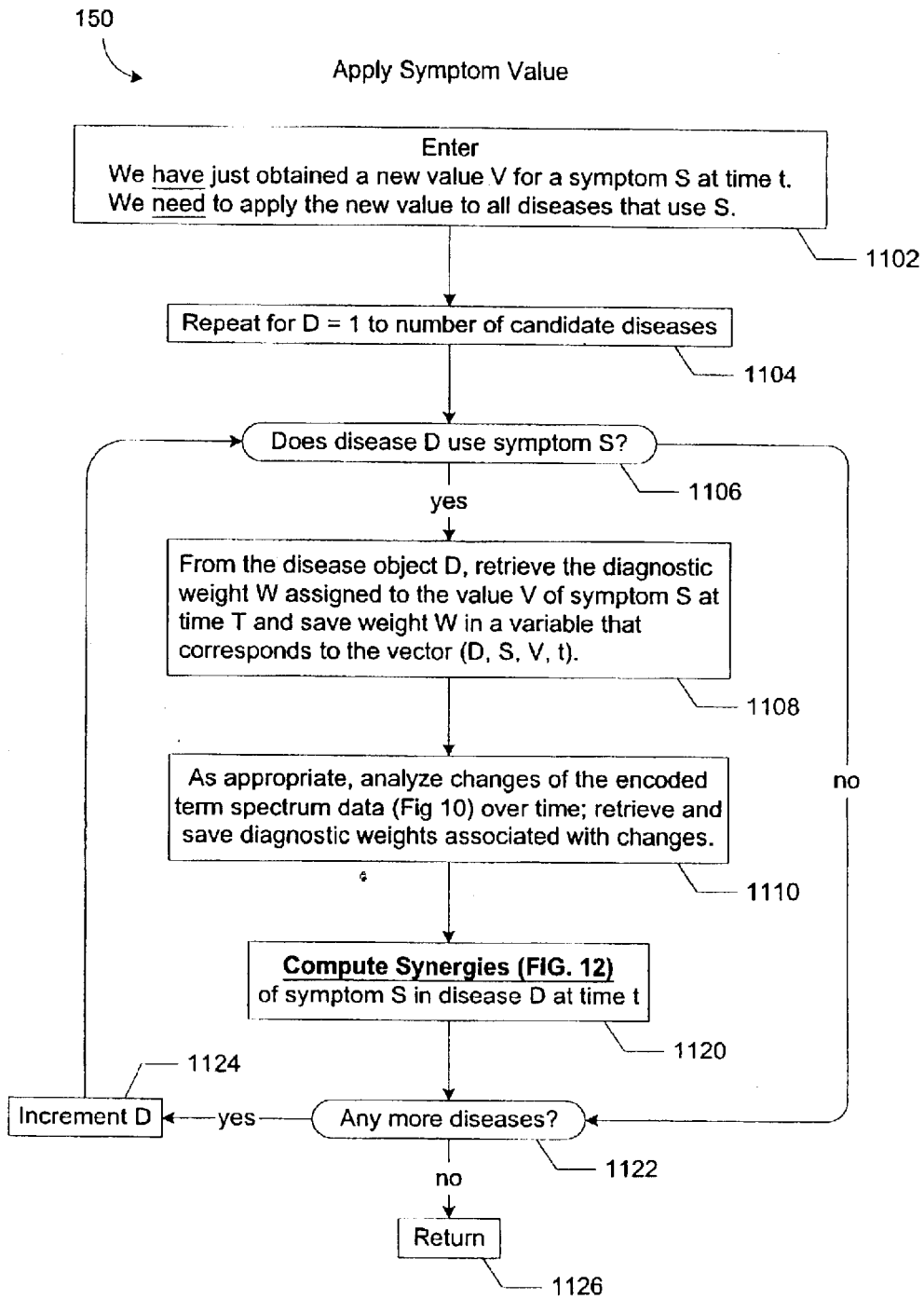
FIG. 11 is a flowchart of the Apply Symptom Value function shown in FIG. 1.

Referring now to FIG. 11, the Apply Symptom Value function 150, which receives a symptom value that has just been elicited or computed and applies it and its effects to various candidate diseases, will be described. In one embodiment, using a central system, function 150 loops through the candidate disease list and applies to each disease D the effects of the new value. For each disease D, it retrieves the appropriate diagnostic weights, computes the applicable synergistic weights, computes the applicable synergy weights, and notes any other effects mandated by the disease author, such as mandatory score changes, disease status changes due to rule-ins and rule-outs, and changes required to handle value changes of symptoms that are acting as alternative symptoms in other diseases.

In an alternative, object-based embodiment, each disease object has a built-in method that processes new symptom values; and function 150 calls that method to "notify" each disease object of the new symptom value. Each disease object is programmed to apply the effects of the new value to its own data, which simplifies the handling of certain highly disease-specific updating rules. However, in either embodiment, the same logical processing takes place.

Figure 21:
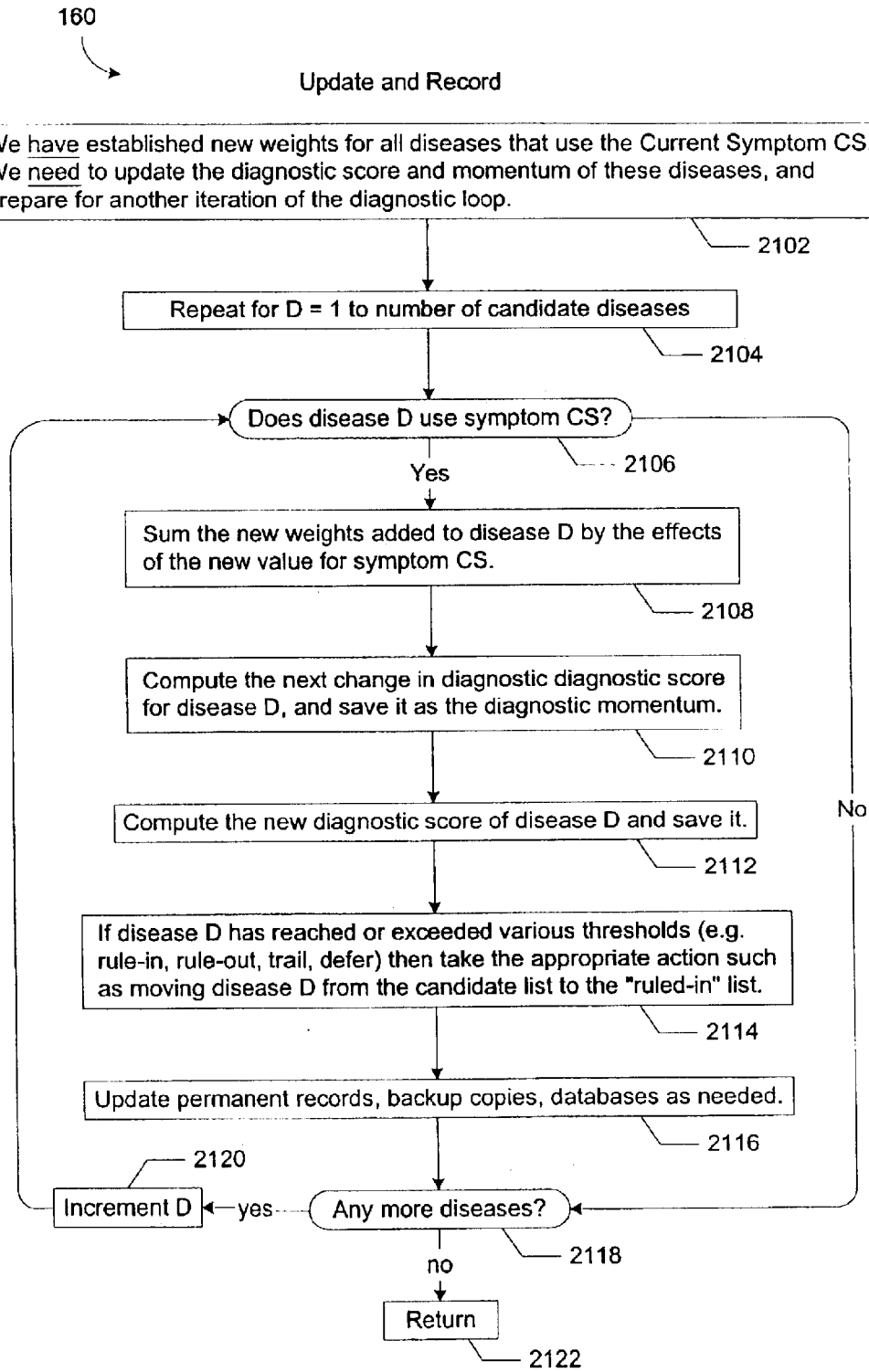
FIG. 21 is a flowchart of the Update and Record function shown in FIG. 1.

Note, in one embodiment, that the diagnostic weight changes computed as a result of the new value are merely saved, but are not added to the diagnostic scores until after all candidate disease changes have been computed and all diseases can be updated in unison (see FIG. 21). This is necessary to prevent changes in scores, rulings, alternative symptom weights, and synergistic effects of diseases near the beginning of the candidate list from influencing and distorting computations for diseases further down the list. Computing score changes and incrementing scores is a two-pass process to insure correct advancing of all diseases scores as a single generation.

Function 150 begins with entry state 1102, where a new symptom value has been computed and must be applied to all candidate diseases that use this symptom. Moving to state 1104, function 150 initiates a loop that processes every disease D in the candidate disease list. Moving to a decision state 1106, if disease D does not use the new symptom, function 150 ignores disease D and moves to a decision state 1122 for another iteration of the loop. But if, at decision state 1106, disease D does use the current symptom, function 150 moves to state 1108 to process it. At state 1108, function 150 retrieves, from the weights table for disease D, the diagnostic weight specified for the value of the current symptom at time t. This new weight is stored in the disease object for D for later processing.

Proceeding to state 1110, if the diagnostic weighting for the current symptom depends on analyzing incremental changes in symptom values over a time interval, function 150 computes the effect of the changes, retrieves a corresponding weight, and saves it for later updating. Advancing to a Compute Synergies function 1120, the impact of the new symptom value on disease D is computed, as further described in conjunction with FIG. 12. Moving to decision state 1122, function 150 checks if there are more candidate diseases to be processed. If so, function 150 moves to state 1124, increments the loop index D and moves back to state 1106 to start another iteration of the loop. But if, at decision state 1122, all candidate diseases have been processed, function 150 moves to state 1126 and returns to the calling process.

Figure 12:
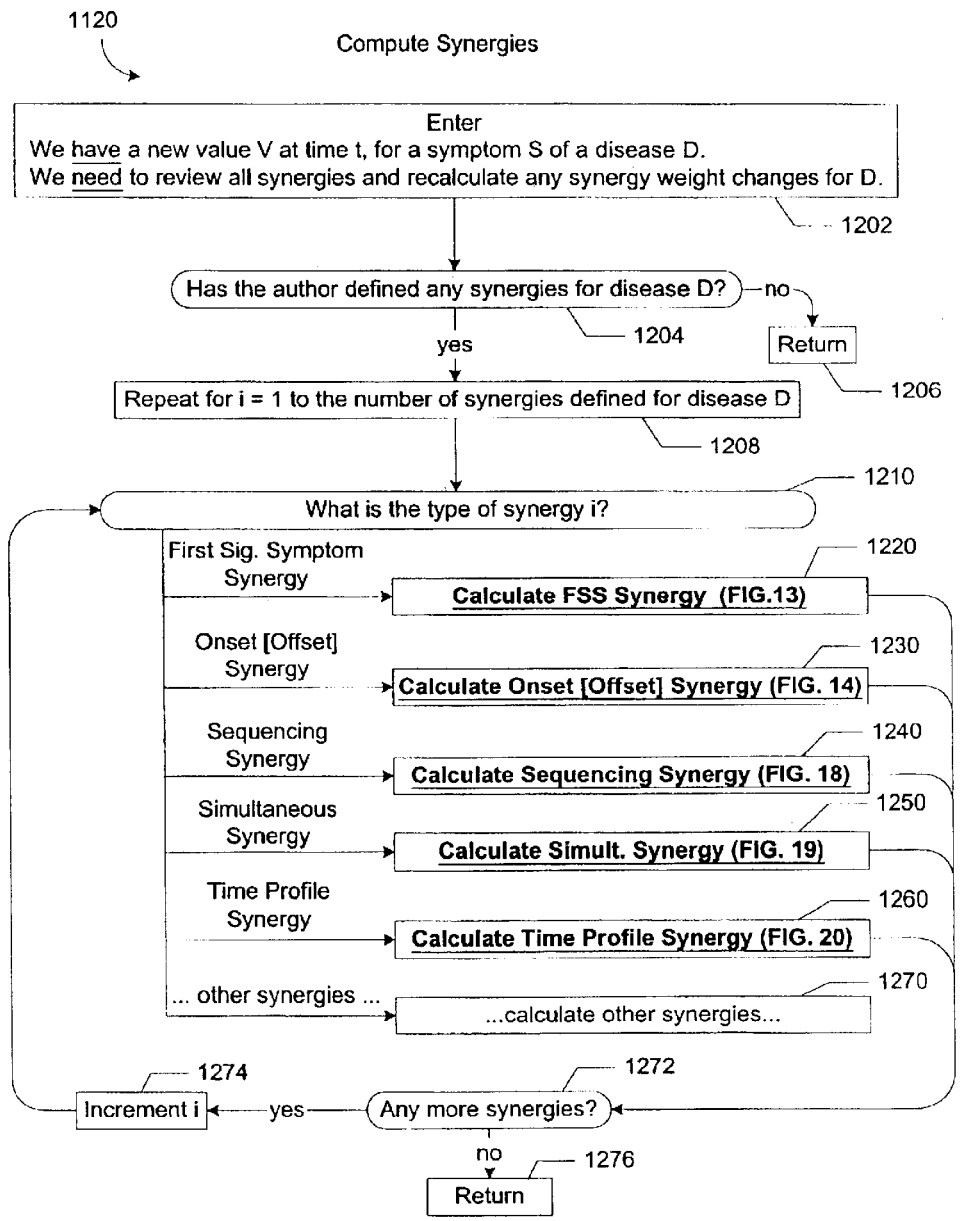
FIG. 12 is a flowchart of the Compute Synergies function shown in FIG. 11.

Referring now to FIG. 12, the Compute Synergies function 1120 (used in FIG. 11), which computes the synergistic weight, if any, of a given symptom value, will be described. Synergy here refers to special predefined qualities of symptoms as well as time-based relationships and interactions among different symptoms, which often have a significant diagnostic impact. Whereas the use of diagnostic weights for simple symptom values is a first-order effect, the use of time-based synergistic values is a second-order effect, a mathematical "fine-tuning" that helps to differentiate competing diagnoses and distinguishes the MDATA system from other automated diagnostic systems. Note that only a few of the major synergy types are shown; there are many possible synergy types that can all be analyzed in a similar manner as shown here.

Figure 13:
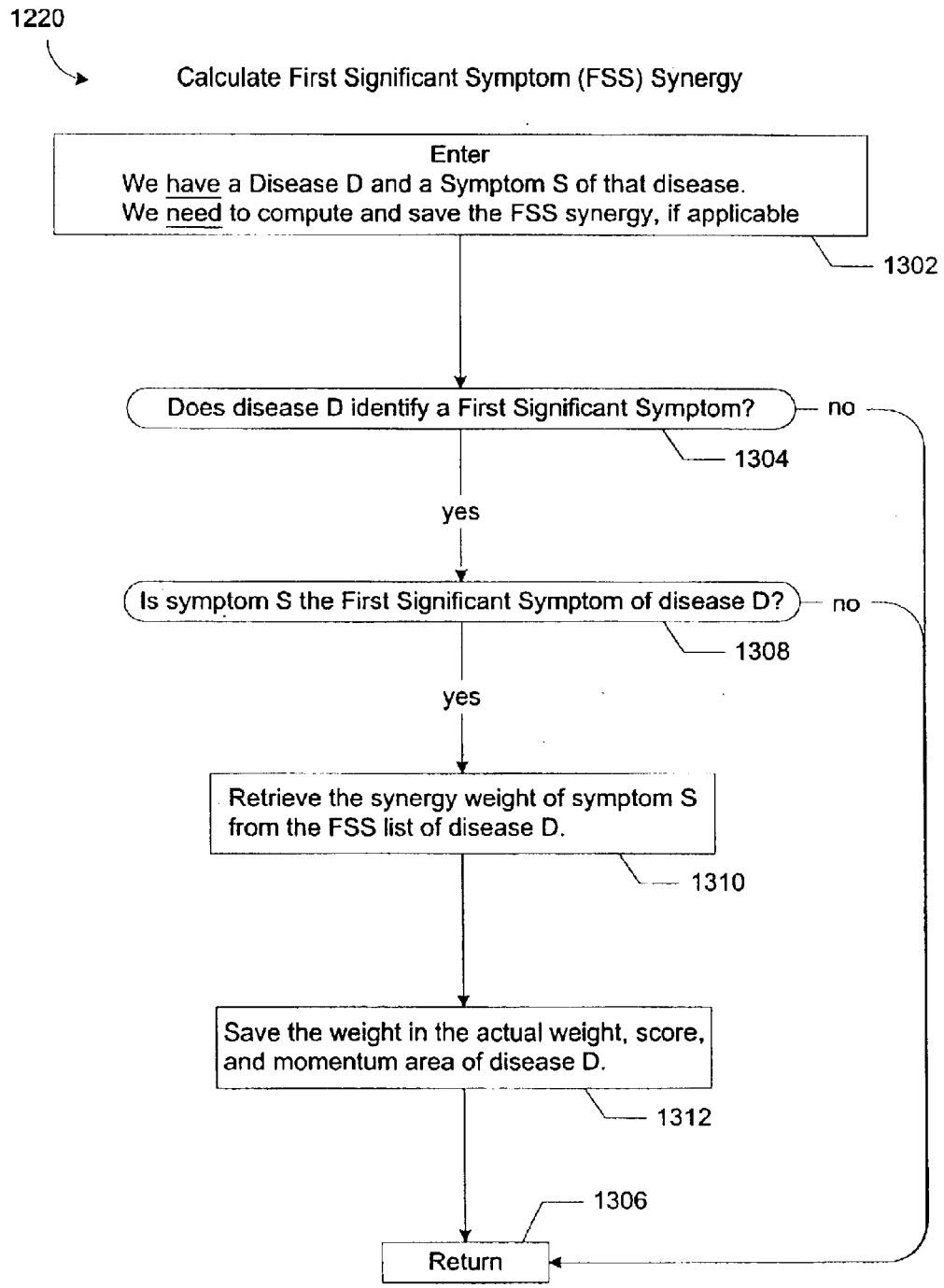
FIG. 13 is a flowchart of the Calculate FSS Synergy function shown in FIG. 12.

Function 1120 begins with entry state 1202, where a new symptom value has been computed and must now be applied to all synergistic symptoms for a given disease. Moving to a decision state 1204, function 1120 tests whether the given disease has any symptoms that involve synergies. If not, function 1120 returns at state 1206; otherwise, function 1120 moves to state 1208 and initializes a loop that processes every synergy i defined for the given disease. Continuing at a decision state 1210, function 1120 obtains the next synergy i of the disease and reviews its type. Depending on the type of synergy i, function 1120 computes the synergy as follows:

If the type of synergy i is First Significant Synergy, function 1120 moves to function 1220 to compute the FSS Synergy, which is further described in conjunction with FIG. 13. Then function 1120 moves to a decision state 1272. If, at decision state 1210, the synergy type is Onset or Offset Synergy, function 1120 moves to function 1230 to compute the Onset or Offset Synergy, which is further described in conjunction with FIG. 14. Then function 1120 moves to decision state 1272. If, at decision state 1210, the synergy type is Sequencing Synergy, function 1120 moves to function 1240 to compute the Sequencing Synergy, which is further described in conjunction with FIG. 18. Then function 1120 moves to decision state 1272. If, at decision state 1210, the synergy type is Simultaneous Synergy, function 1120 moves to function 1250 to compute the Simultaneous Synergy, which is further described in conjunction with FIG. 19. Then function 1120 moves to decision state 1272. If, at decision state 1210, the synergy type is Time Profile Synergy, function 1120 moves to function 1260 to compute the Time Profile Synergy, which is further described in conjunction with FIG. 20. Then function 1120 moves to decision state 1272. If, at decision state 1210, the synergy type is some other synergy, function 1120 moves to state 1270 to compute the synergy. State 1270 is intended to show that there may be many other symptom combinations that exhibit synergy, which would be computed in like manner as functions 1220 through 1260.

After any one synergy symptom has been computed, function 1120 moves to decision state 1272 and checks whether there are more synergies to process. If so, function 1120 moves to state 1274 where it increments the index that selects the next synergy and then moves back to state 1210 to initiate another iteration of the loop. But if, at decision state 1272, there are no more synergies to compute, function 1120 moves to state 1276 and returns to the calling process.

Referring now to FIG. 13, the Calculate First Significant Symptom (FSS) function 1220 (FIG. 12) will be described. The FSS function 1220 determines if a given actual symptom value belongs to the first significant symptom of a given disease in order to add extra diagnostic weight to that disease. The meaning of "first significant symptom" is illustrated in and described in conjunction with FIG. 28 as the earliest symptom in the disease process.

Function 1220 begins with entry state 1302, where a new value has been computed for a symptom and function 1220 must now retrieve the extra diagnostic weight associated with the symptom being the First Significant Symptom of the disease. Moving to a decision state 1304, function 1220 tests whether the given disease identifies any first significant symptoms. If not, function 1220 returns at once at state 1306, otherwise function 1220 moves to a decision state 1308 and checks whether the given symptom is identified as a First Significant Symptom of the given disease's timeline. If not, function 1220 returns at once at state 1306, otherwise function 1220 moves to state 1310. At state 1310, function 1220 retrieves the diagnostic weight specified for the given symptom value for the disease and moves to state 1312. At state 1312, function 1220 saves the diagnostic weight, moves to state 1306 and returns to function 1120 (FIG. 12).

Figure 14:
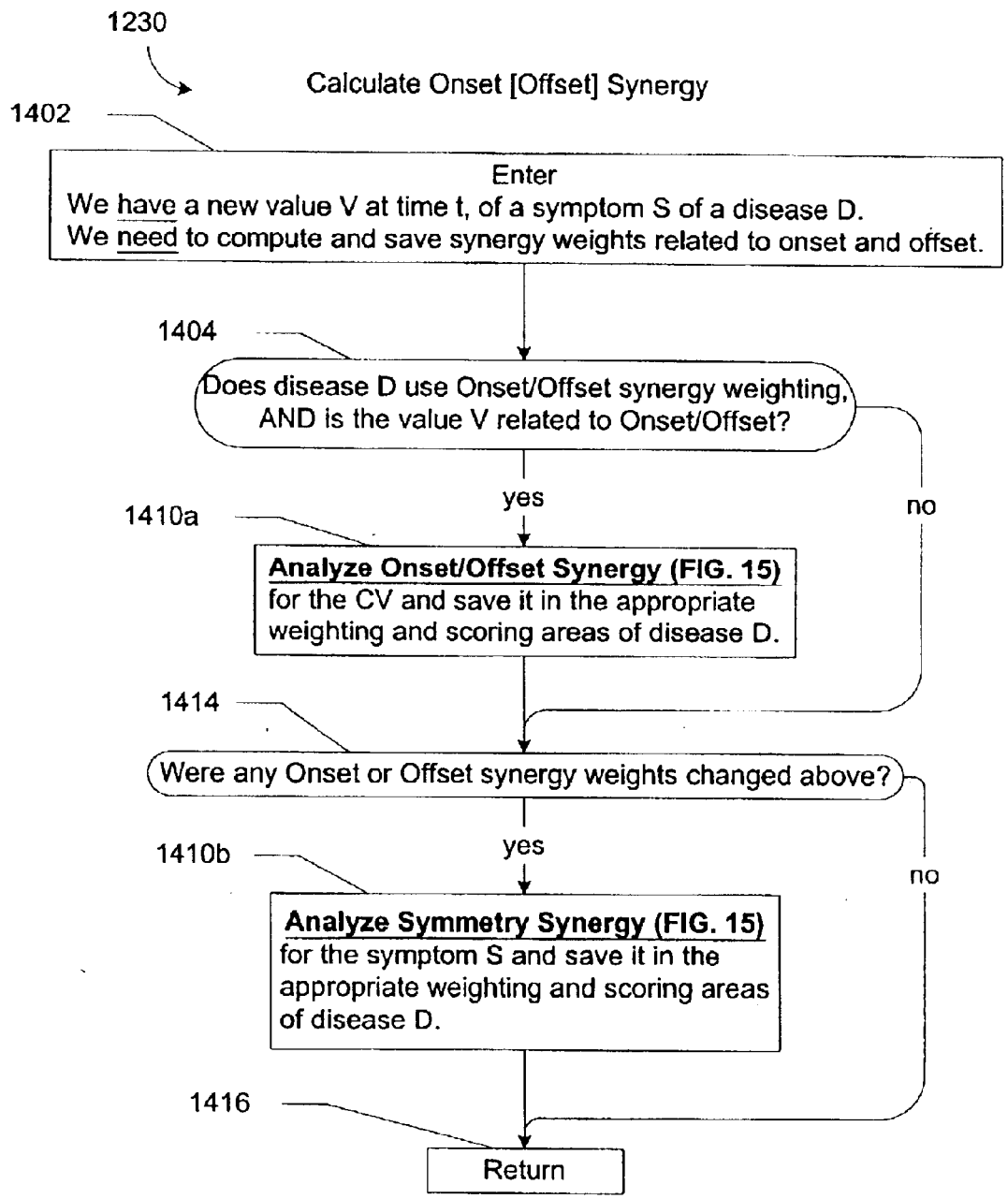
FIG. 14 is a flowchart of the Calculate Onset [Offset] Synergy function shown in FIG. 12.

Referring now to FIG. 14, the Calculate Onset [Offset] Synergy function 1230 (used in FIG. 12) will be described. Function 1230 analyzes if and how the values of a given symptom exhibit special onset (or offset) characteristics that have medical significance and thus add extra diagnostic weight to the disease.

Function 1230 begins with entry state 1402, where a new value has been computed for a symptom and the function must now retrieve the extra diagnostic weight associated with special onset and offset values of the given symptom. Moving to a decision state 1404, function 1230 tests whether the disease uses onset/offset analysis and whether it identifies the given symptom value as a special onset or offset value.

If the given symptom does not use onset/offset analysis, function 1230 moves to state 1416 to return at once (at state 1416); otherwise it moves to function 1410*a*. At function 1410*a*, the onset or offset synergy of the new symptom value is analyzed (as described at FIG. 15) and then moves to a decision state 1414. At decision state 1414, function 1230 checks whether its previous processing has changed any onset or offset values. If so, the function moves to function 1410*b*, or otherwise to state 1416. At function 1410*b*, the symmetry between onset and offset is analyzed and synergy weight is assigned (as described at FIG. 15). At the completion of function 1410*b*, function 1230 moves to state 1416 and returns to the calling function 1120 (FIG. 12).

Figure 15:
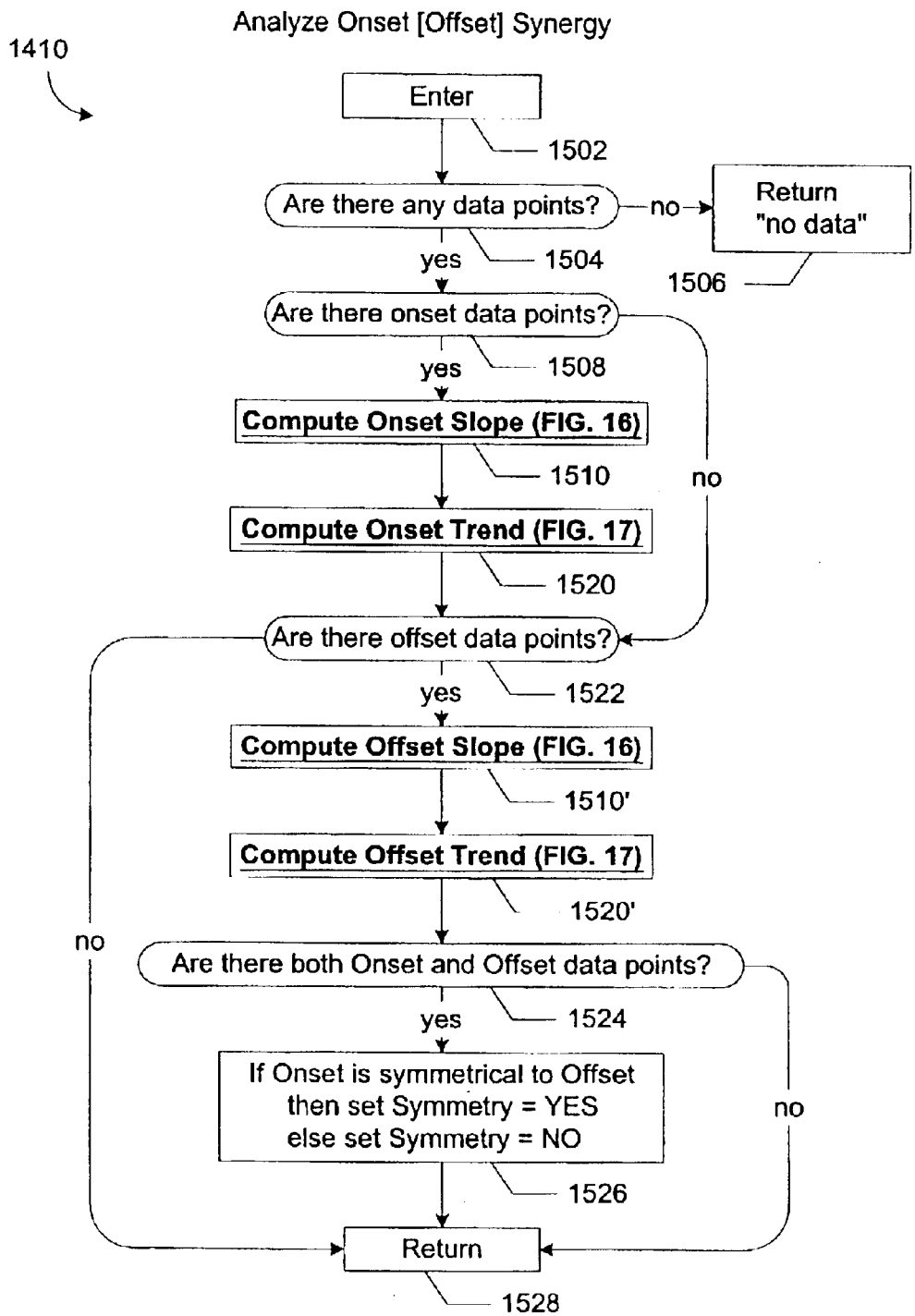
FIG. 15 is a flowchart of the Analyze Onset [Offset] Synergy function shown in FIG. 14.

Referring now to FIG. 15, function 1410, which analyzes the onset and offset values of a given symptom and determines their characteristics with respect to time, will be described. Function 1410 includes a portion 1410*a* to analyze an onset or offset synergy and a portion 1410b to analyze symmetry synergy.

Function 1410 begins with entry state 1502, where the new symptom values are given. Moving to a decision state 1504, if the given values are not related to onset or offset, the function returns a "no data" signal at decision state 1504; otherwise function 1410 can perform portion 1410a to analyze an onset or offset synergy and moves to a decision state 1508. At decision state 1508, if there are new values related to symptom onset, function 1410 moves to function 1510, or otherwise to a decision state 1522. At function 1510, the diagnostic weight of the slope of symptom onset with respect to time is computed as further described in FIG. 16. Moving to function 1520, the diagnostic weight of the trend, i.e., the change of slope of symptom onset with respect to time is computed, as further described in FIG. 17. Moving to decision state 1522, if there are new offset values, function 1410 moves to function 1510', otherwise function 1410 returns at state 1528. At function 1510', diagnostic weight of the slope of symptom offset with respect to time is computed, as further described in FIG. 16. Moving to function 1520', the diagnostic weight of the trend, i.e., the change of slope of symptom offset with respect to time is computed, as further described in FIG. 17. Moving to a decision state 1524, if there are both onset and offset values in the symptom, function 1410 can perform portion 1410b to analyze symmetry synergy and proceeds to state 1526; otherwise function 1410 returns at state 1528. At state 1526, the function portion 1410b computes the diagnostic weight of the symptom onset/offset symmetry. Moving to state 1528, function 1410 returns to the calling function 1230 (FIG. 14).

Figure 16:
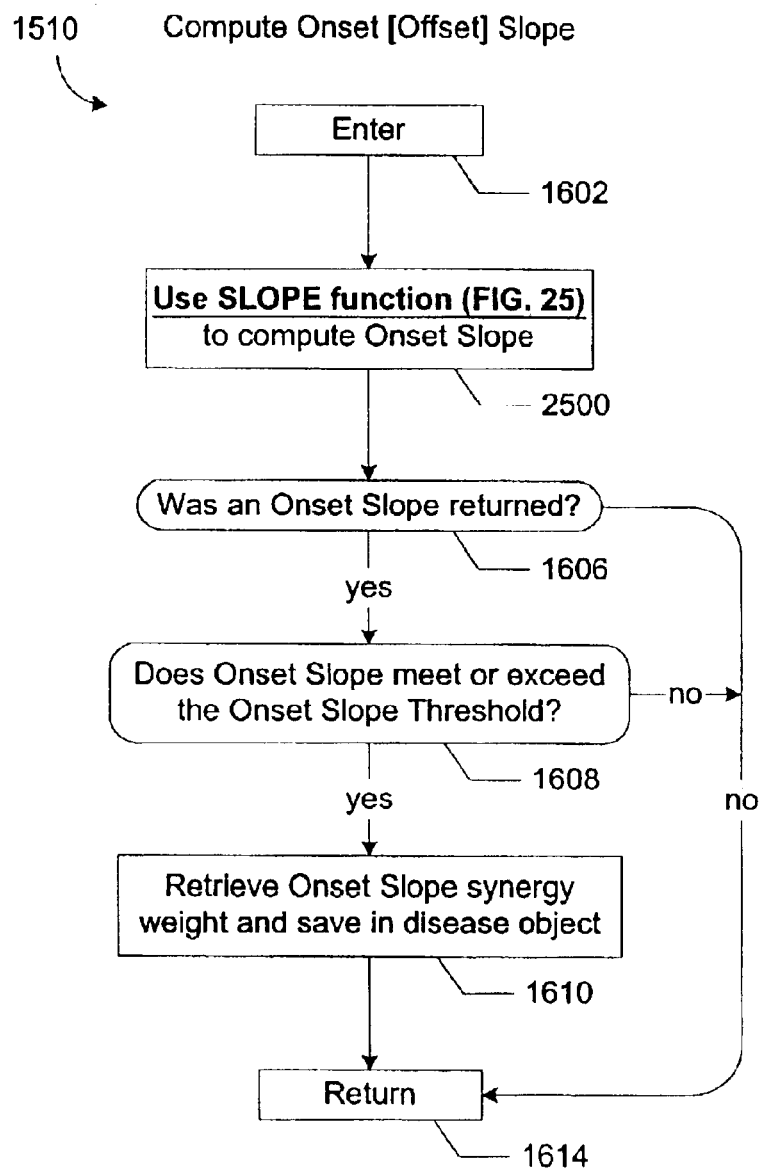
FIG. 16 is a flowchart of the Compute Onset [Offset] Slope function shown in FIG. 15.

Referring now to FIG. 16, function 1510, which computes the diagnostic weight of onset and offset slopes for a symptom, will be described. This description is for symptom onset (1510); a similar description applies for symptom offset (1510'). Function 1510 begins with entry state 1602, where new symptom values are given. Moving to a function 2500, the slope with respect to time of the given onset or offset value is computed, as further described in conjunction with FIG. 25. Moving to a decision state 1606, if no valid slope was returned by function 2500, function 1510 returns at state 1614; otherwise it moves to a decision state 1608. At decision state 1608, if the onset slope does not reach or exceed the onset slope threshold, function 1510 returns at state 1614; otherwise function 1510 moves to state 1610. At state 1610, function 1510 retrieves the weight assigned to the onset slope value for the given symptom and saves it for later analysis in the disease object. Moving to state 1614, function 1510 returns to function 1410 (FIG. 15).

Figure 17:
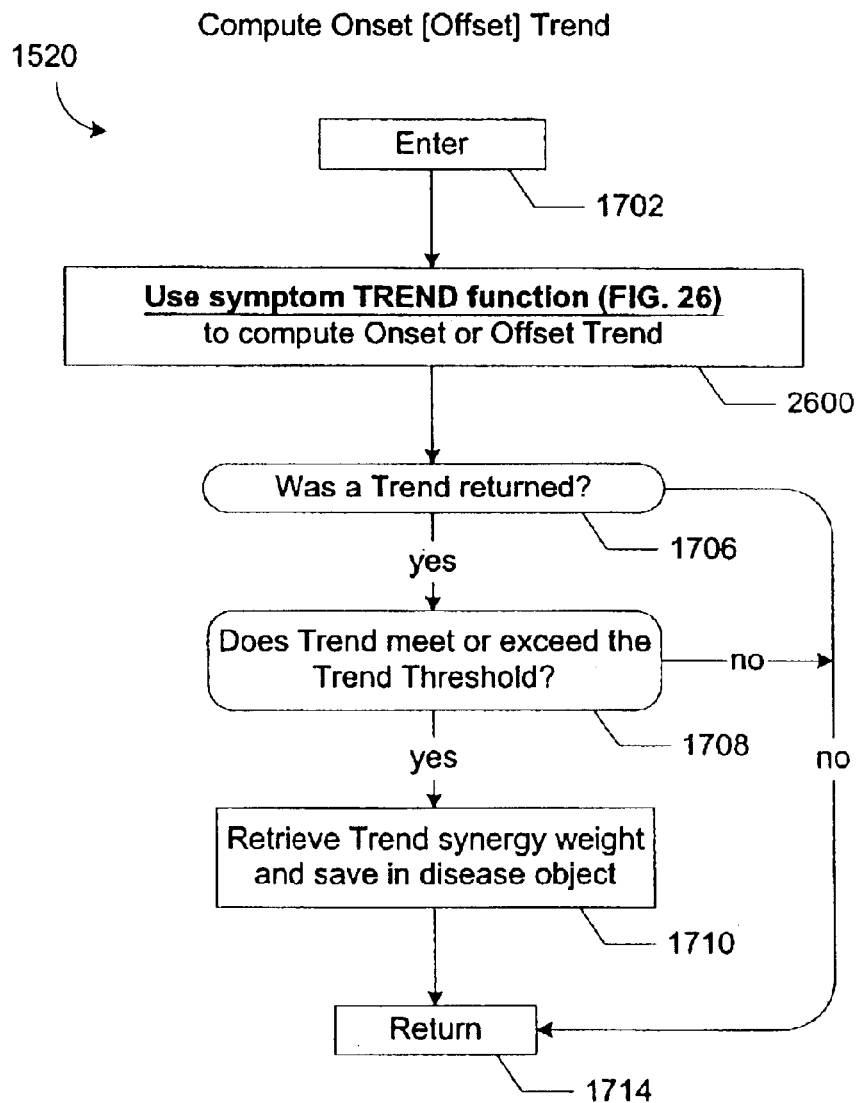
FIG. 17 is a flowchart of the Compute Onset [Offset] Trend function shown in FIG. 15.

Referring now to FIG. 17, function 1520, which computes the diagnostic weight of onset (1520) and offset (1520') trends for a symptom, will be described. The speed with which a symptom begins or ends in a patient has diagnostic significance, which is determined and weighted by this function. This description is for symptom onset trend (1520); a similar description applies for symptom offset trend (1520').

Function 1520 begins with entry state 1702, where new symptom values are given. Moving to a function 2600, the trend with respect to time of the given onset value is computed, as further described in conjunction with FIG. 26. Moving to a decision state 1706, if no valid trend was returned by function 2600, function 1520 returns at state 1714; otherwise it moves to a decision state 1708. At decision state 1708, if the onset trend is less than the onset trend threshold, function 1520 returns at state 1714; otherwise function 1520 moves to state 1710. At state 1710, function 1520 retrieves the weight assigned to the onset trend value and saves it for later analysis in the disease object. Moving to state 1714, function 1520 returns to the caller function 1410 (FIG. 15).

Figure 18:
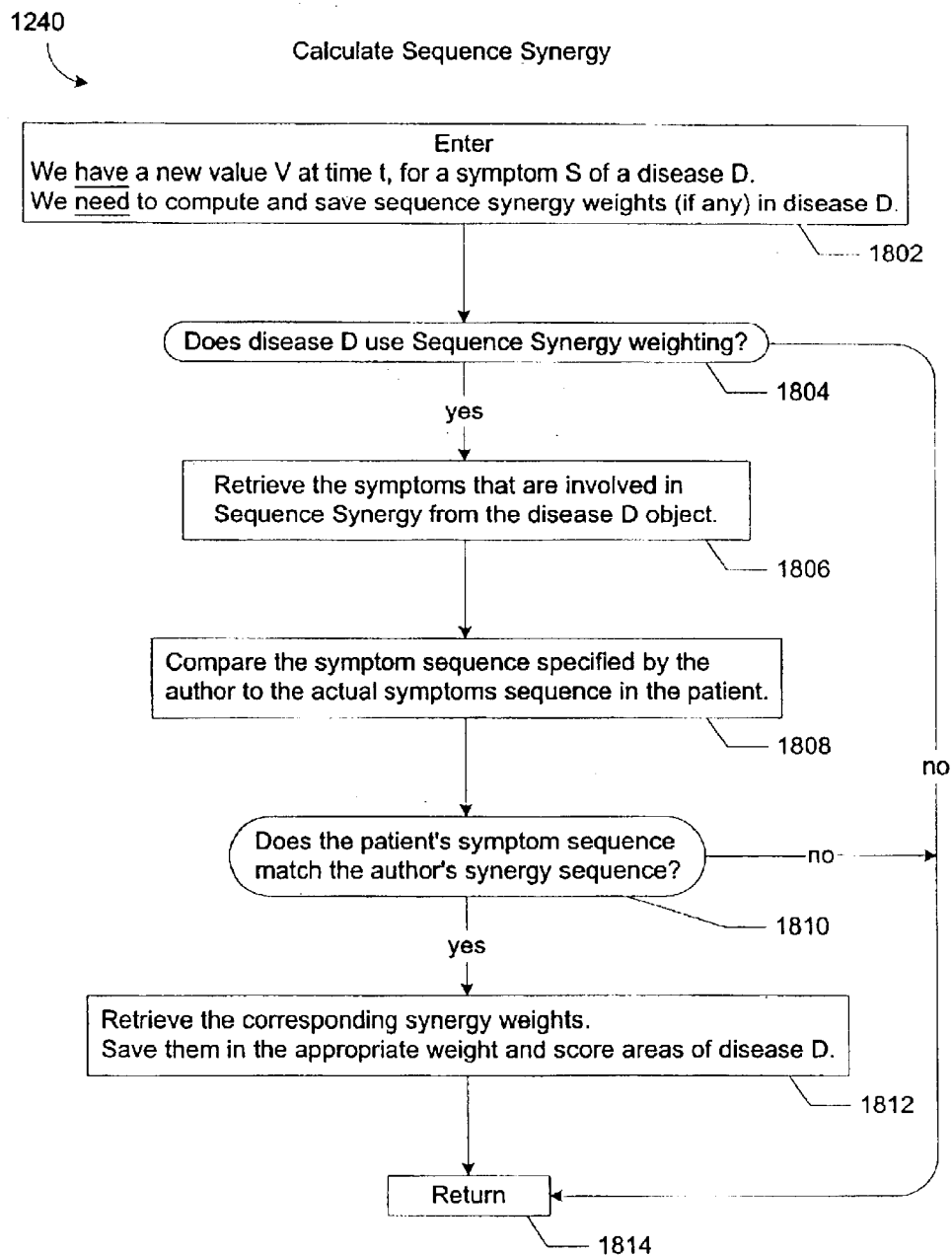
FIG. 18 is a flowchart of the Calculate Sequencing Synergy function shown in FIG. 12.

Referring now to FIG. 18, the Calculate Sequence Synergy function 1240 (FIG. 12) will be described. Function 1240 checks whether a specific, author-defined sequence of symptom values occurred in the patient being diagnosed for a given disease. If so, function 1240 retrieves the extra diagnostic synergy weight associated with that special symptom sequence and saves it for later analysis.

Function 1240 begins with entry state 1802, where a disease and a symptom value at some time t is given to the function. Moving to a decision state 1804, function 1240 tests whether the disease author defined any sequence synergy weighting at all. If so, function 1240 moves to state 1806, otherwise it returns at once at return state 1814. At state 1806, function 1240 retrieves from the disease object all symptom values that are involved in the sequence synergy computation. Moving to state 1808, function 1240 compares the time sequence of symptom values actually reported in the patient to the author's time sequence of symptoms. Moving to a decision state 1810, if the patient's symptom sequence matches the author's, function 1240 moves to state 1812; otherwise the function returns at state 1814. At state 1812, function 1240 retrieves the diagnostic weight associated with the symptom time sequence from the given disease's weight table and saves the weight with any other actual weights of the given disease. Moving to state 1814, function 1240 returns to its caller function 1120 (FIG. 12).

Figure 19:
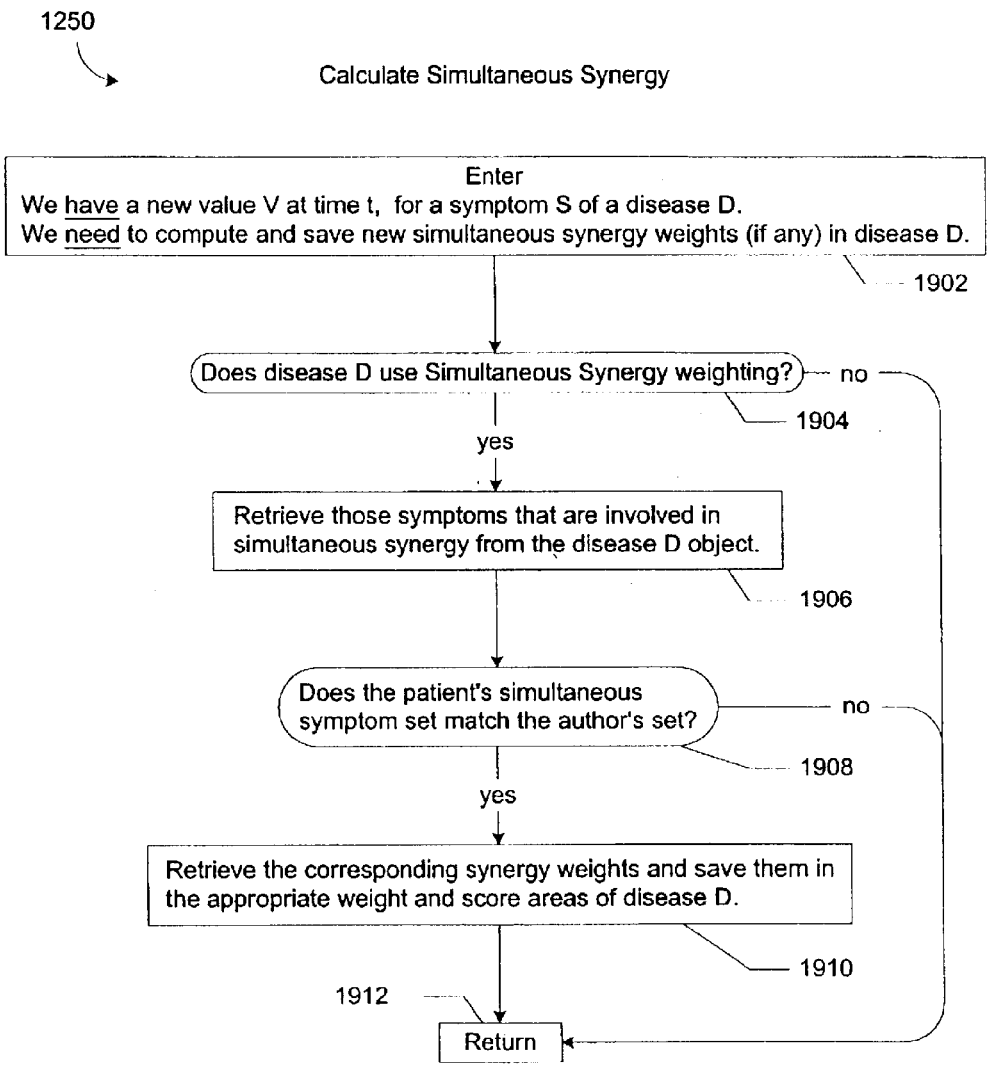
FIG. 19 is a flowchart of the Calculate Simultaneous Synergy function shown in FIG. 12.

Referring now to FIG. 19, the Calculate Simultaneous Synergy function 1250 (FIG. 12) will be described. Function 1250 checks whether a specific, author-defined set of symptom values occurred at the same time or over the same time period in the patient being diagnosed for a given disease. If so, function 1250 retrieves the extra diagnostic weight associated with that special set of simultaneous symptoms and adds it to the list of actual diagnostic weights of the disease.

Function 1250 begins with entry state 1902, where a disease and a symptom value at some time t is given to the function. Moving to a decision state 1904, function 1250 tests whether the disease author defined any simultaneous synergy weighting at all. If so, function 1250 moves to state 1906, otherwise it returns at once at return state 1912. At state 1906, function 1250 retrieves from the disease object all symptom values that are involved in the simultaneous synergy computation. Moving to a decision state 1908, if the patient's symptom set at time t matches the author's predefined symptom set, function 1250 moves to state 1910; otherwise the function returns at state 1912. At state 1910, function 1250 retrieves the diagnostic weight associated with the simultaneous symptom set from the given disease's weight table and saves the weight with any other actual weights of the given disease. Moving to state 1912, function 1250 returns to its caller function 1120 (FIG. 12).

Figure 20:
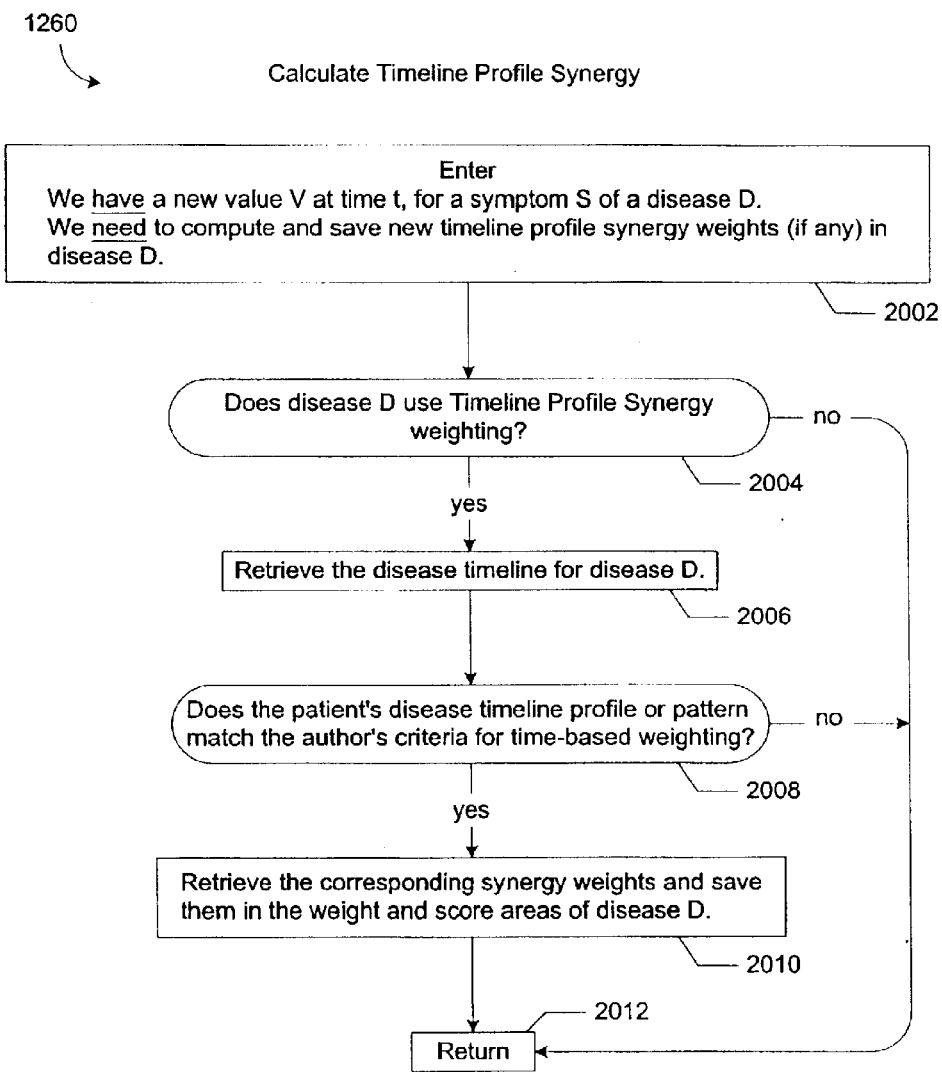
FIG. 20 is a flowchart of the Calculate Time Profile Synergy function shown in FIG. 12.

Referring now to FIG. 20, the Calculate Timeline Profile Synergy function 1260 (FIG. 12) will be described. Function 1260 checks whether the patient being diagnosed for a given disease has reported a symptom time profile (FIG. 28) or individual symptom values occurring at time t such that they match or "fit into" a specific, author-defined disease time profile or disease timeline. If the given symptom occurred in the patient with predefined values at times that correspond to a disease time profile defined by the author, function 1260 retrieves the extra diagnostic weight that the author associated with the symptom time profile and adds it to the list of actual diagnostic weights of the disease.

Function 1260 begins with entry state 2002, where a disease and a symptom value at time t is given to the function. Moving to a decision state 2004, function 1260 tests whether the disease author defined any symptom time profile weights at all. If so, function 1260 moves to state 2006, otherwise it returns at once at return state 2012. At state 2006, function 1260 retrieves from the disease object the symptom time profile that is involved in the computation. Moving to a decision state 2008, if the patient's symptom time profile matches the author-defined time profile, function 1260 moves to state 2010; otherwise the function returns at state 2012. At state 2010, function 1260 retrieves the diagnostic weight associated with the time profile from the given disease's weight table and saves the weight with any other actual weights of the given disease. Moving to state 2012, function 1260 returns to its caller function 1120 (FIG. 12).

Referring now to FIG. 21, the Update and Record function 160 (FIG. 1) will be described. Prior to entry into Function 160, the diagnostic loop 100 has just recomputed the diagnostic weights of all candidate diseases based on some new value for the current focus symptom. Function 160 now allows each candidate disease to take one small incremental diagnostic step, based on the new value. Function 160 updates the diagnostic momentum, score, and status of each candidate disease, and modifies and reviews their diagnostic ranking. If this latest step causes one or more diseases to reach a diagnostic decision point, function 160 processes that decision. Function 160 then prepares the candidate disease list for another iteration of the diagnostic loop.

Function 160 begins with entry state 2102, where new weights have been established in all candidate diseases that use the current symptom. Moving to state 2104, function 160 initializes a loop to process each disease in the candidate disease list in turn, as disease D. Moving to a decision state 2106, if disease D does not use the current symptom, then it cannot have been affected by the latest weight changes, so function 160 skips the rest of the loop and moves to a decision state 2118. But if, at decision state 2106, disease D does use the current symptom, then function 160 moves to state 2108. At state 2108, function 160 sums all of the diagnostic weights added by the new symptom value D. This includes the basic weight of the symptom value and all extra, incremental weights added by the various synergy functions. Moving to state 2110, function 160 computes the diagnostic momentum of disease D, which, in one embodiment, is simply the sum computed at state 2108. This momentum is the incremental diagnostic progress made by disease D for the current question. It is saved and used in another context to evaluate how fast disease D is advancing compared to other candidate diseases. Moving to state 2112, function 160 updates the diagnostic score of disease D by adding to it the momentum computed in state 2110.

Moving to state 2114, function 160 reviews and adjusts the diagnostic status of disease D. Function 160 compares the new diagnostic score to various author-defined thresholds that signal status changes such as ruling disease D 'in' or 'out', or changing the diagnostic rank of disease D so that it will receive more or less attention in the next iteration of the diagnostic loop. Moving to state 2116, function 160 updates various working lists and databases to record the actions and decisions taken with respect to disease D.

Moving to decision state 2118, if there are more candidate diseases to be processed, function 160 moves to state 2120 which increments the loop index D and then moves back to state 2106 which starts another iteration. But if, at decision state 2118, there are no more diseases to be processed, function 160 moves to state 2122 and returns to the caller, which in this case is function 170 of FIG. 1.

Figure 22:
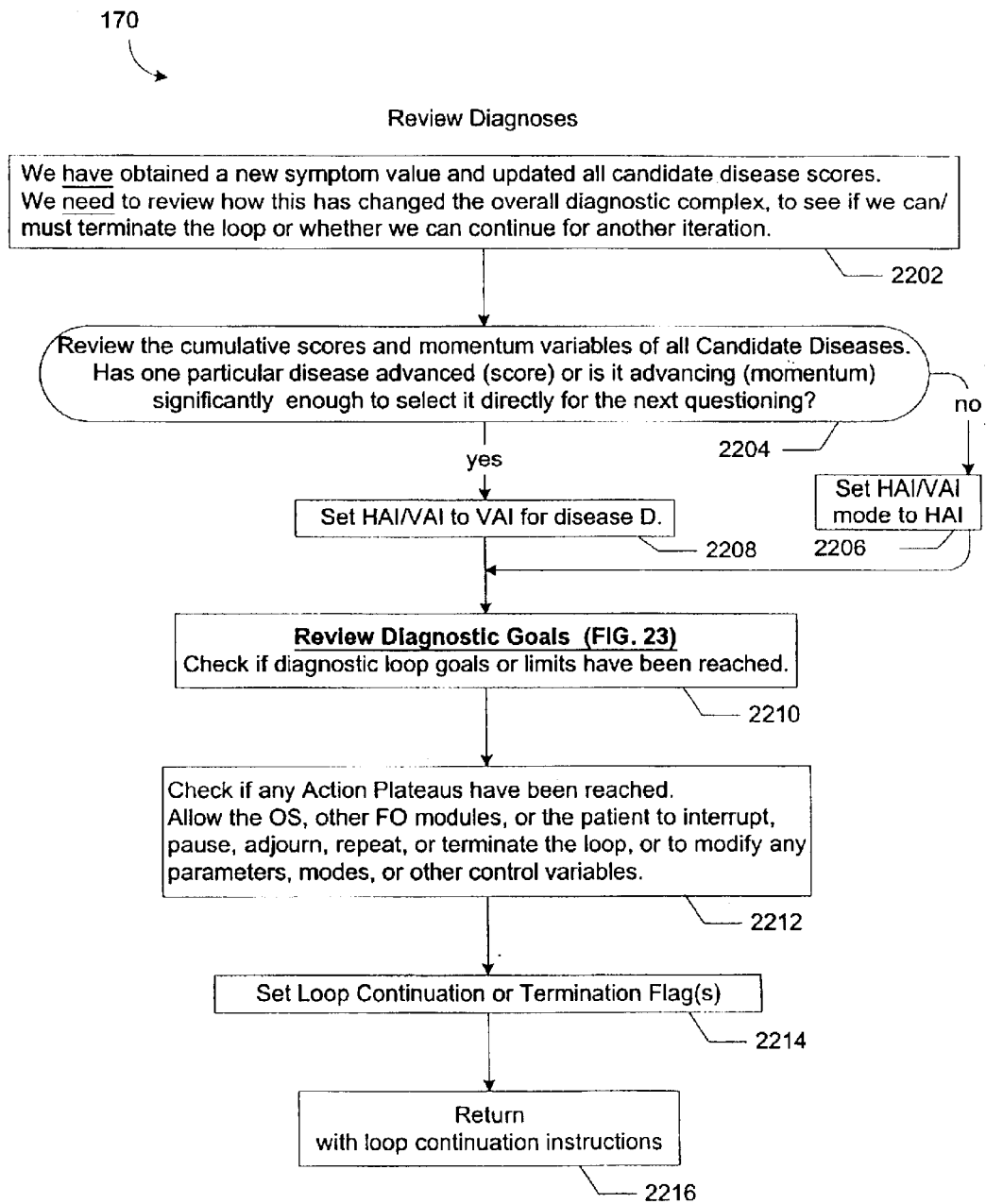
FIG. 22 is a flowchart of the Review Diagnoses function shown in FIG. 1.

Referring now to FIG. 22, the Review Diagnoses function 170 as used in the diagnostic loop (FIG. 1) will be described. At the entry to function 170, the system has just updated all candidate diseases with new diagnostic weights and scores, and function 170 now reviews the candidate diseases to see if another iteration of the diagnostic loop is in order, or if diagnostic session goals or limits have been reached.

Function 170 begins with entry state 2202, where all candidate diseases have just been updated. Moving to a decision state 2204, function 170 reviews the diagnostic momentum and score of each candidate disease. If any one disease has advanced significantly enough to be selected as the next current disease, function 170 moves to state 2208 to set the diagnostic mode to VAI for that disease, and then function 170 moves to function 2210. But if, at decision state 2204, no one disease has made special progress toward a diagnosis, function 170 moves to state 2206 to set the diagnostic mode to HAI, and then moves to function 2210. Function 2210 reviews the diagnostic goals and limits, which is further described in conjunction with FIG. 23. At the completion of function 2210, function 170 advances to state 2212 and checks to see if any process in the loop has requested termination, adjournment or other interruption, or has modified the diagnostic mode or parameters or options used in the diagnostic loop 100. State 2212 also processes actions requests triggered by the action plateau feature, which allows any disease object to request premature termination of the loop in favor of performing some other action such as is sometimes required in emergency cases. Moving to state 2214, function 170 sets internal flags to either continue or terminate the diagnostic loop. Moving to state 2216, function 170 returns to the caller, which in this case is state 172 of FIG. 1.

Figure 23:
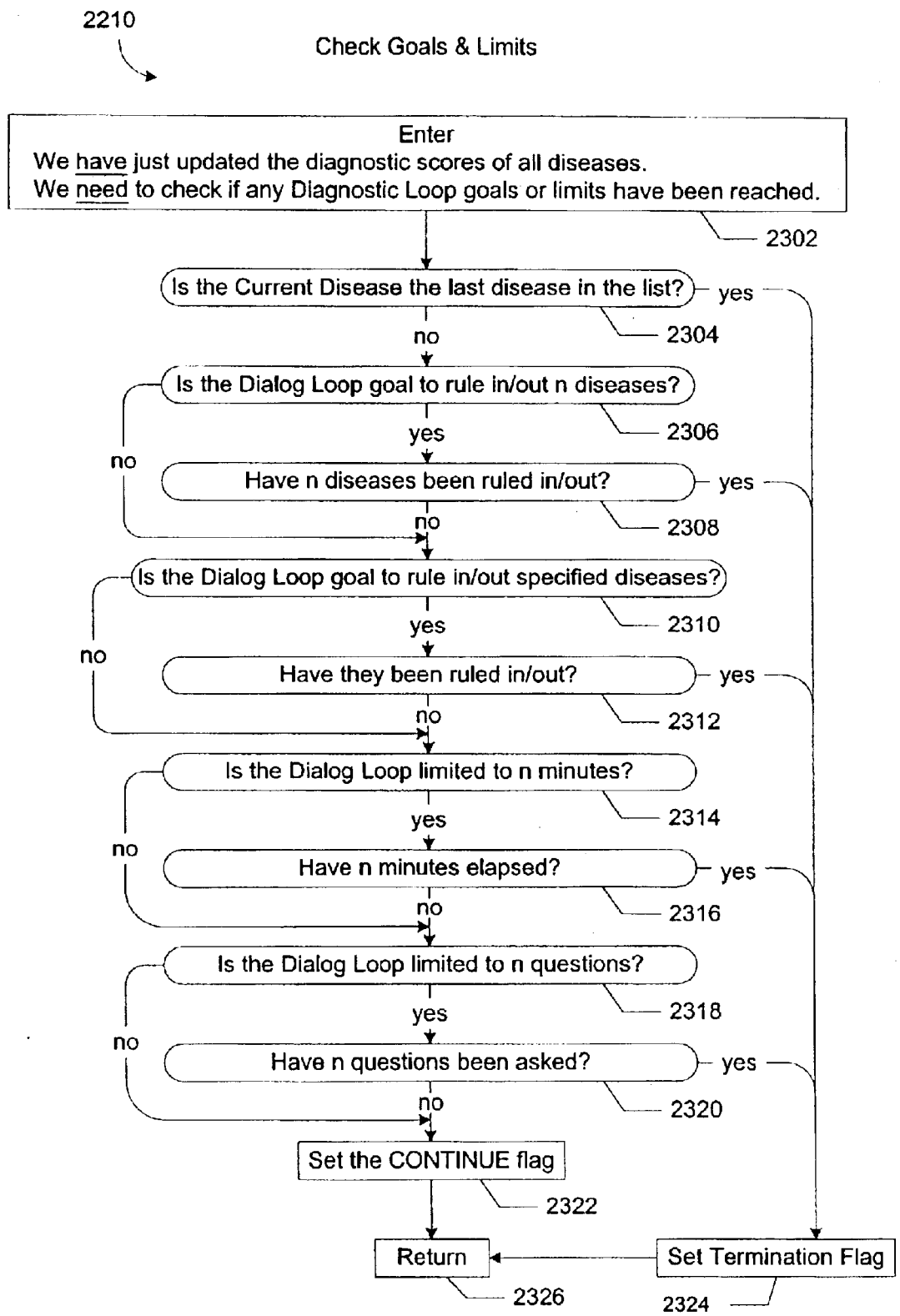
FIG. 23 is a flowchart of the Review Diagnostic Goals function shown in FIG. 22.

Referring now to FIG. 23, the Check Goals and Limits function 2210, as used in the diagnostic loop (FIG. 22), will be described. In function 2210, all candidate disease scores and diagnostic rankings have just been updated, and the function must now review the candidate diseases to see if global diagnostic session goals or limits have been reached. The diagnostic system is poised for another iteration of the diagnostic loop 100, and in function 2210 it determines whether another iteration is in fact required or advisable.

Function 2210 begins with entry state 2302, where all candidate diseases have just been updated. Moving to a decision state 2304, if there are no more candidate diseases to be diagnosed, function 2210 moves to state 2324 to set the loop termination flag. But if, at decision state 2304, there are more candidate diseases, function 2210 moves to a decision state 2306. At decision state 2306, if the diagnostic goal is to rule some given number n of diseases in (or out), function 2210 moves to a decision state 2308; otherwise it moves to a decision state 2310. At decision state 2308, if at least n diseases have indeed been ruled in (or out), function 2210 moves to state 2324 to set the loop termination flag; otherwise function 2210 moves to decision state 2310. At decision state 2310, if the diagnostic goal is to rule certain specified diseases in (or out), function 2210 moves to a decision state 2312; otherwise it moves to a decision state 2314. At decision state 2312, if the specified diseases have indeed been ruled in (or out), function 2210 moves to state 2324 to set the loop termination flag; otherwise function 2210 moves to decision state 2314.

At decision state 2314, if the diagnostic loop is limited to some given time interval, function 2210 moves to a decision state 2316; otherwise it moves to a decision state 2318. At decision state 2316, if the specified time interval has elapsed, function 2210 moves to state 2324 to set the loop termination flag; otherwise function 2210 moves to decision state 2318. At decision state 2318, if the diagnostic loop is limited to some given number of questions, function 2210 moves to a decision state 2320; otherwise it moves to state 2322. At decision state 2320, if the specified number of questions have been asked, function 2210 moves to state 2324 to set the loop termination flag; otherwise function 2210 moves to state 2322. At state 2322, function 2210 sets an internal flag to continue the diagnostic loop and moves to return state 2326. At state 2324, function 2210 sets an internal flag to terminate the diagnostic loop and moves to state 2326 and returns to function 170 (FIG. 22).

Figure 24:
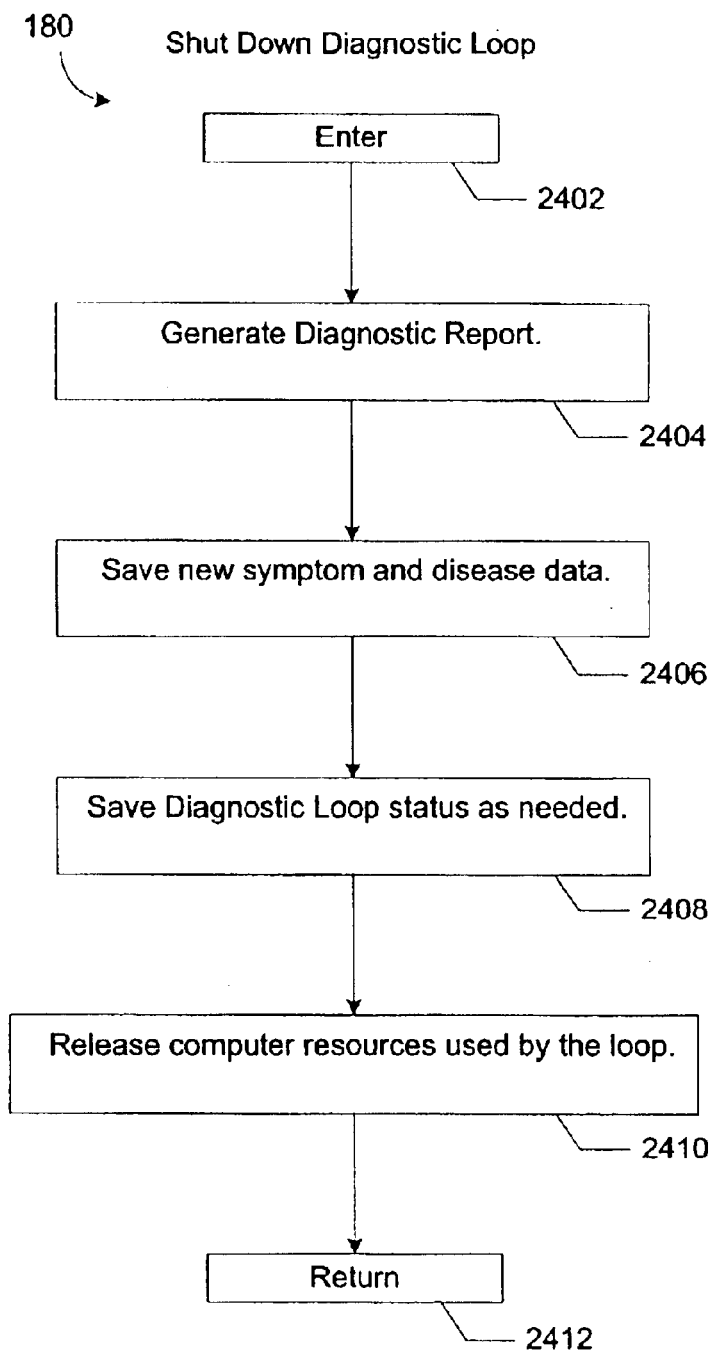
FIG. 24 is a flowchart of the Shut Down Diagnostic Loop function shown in FIG. 1.

Referring now to FIG. 24, the Shut Down Diagnostic Loop function 180 (FIG. 1) of the diagnostic loop 100 will be described. At the entry to function 180, the diagnostic loop is being terminated, and function 180 now performs the actions that are part of an orderly termination and shut-down of the loop.

Function 180 begins with entry state 2402. Moving to state 2404, function 180 generates the required diagnostic reports. Moving to state 2406, function 180 saves newly generated disease and symptom data. Moving to state 2408, function 180 saves the diagnostic loop "state" at termination, which enables the system to continue the loop at a future time by resetting all variables to the same "state". Moving to state 2410, function 180 releases all computer and system resources that were allocated to the diagnostic loop 100. Moving to state 2412, function 180 returns to state 182 of FIG. 1.

Figure 25:
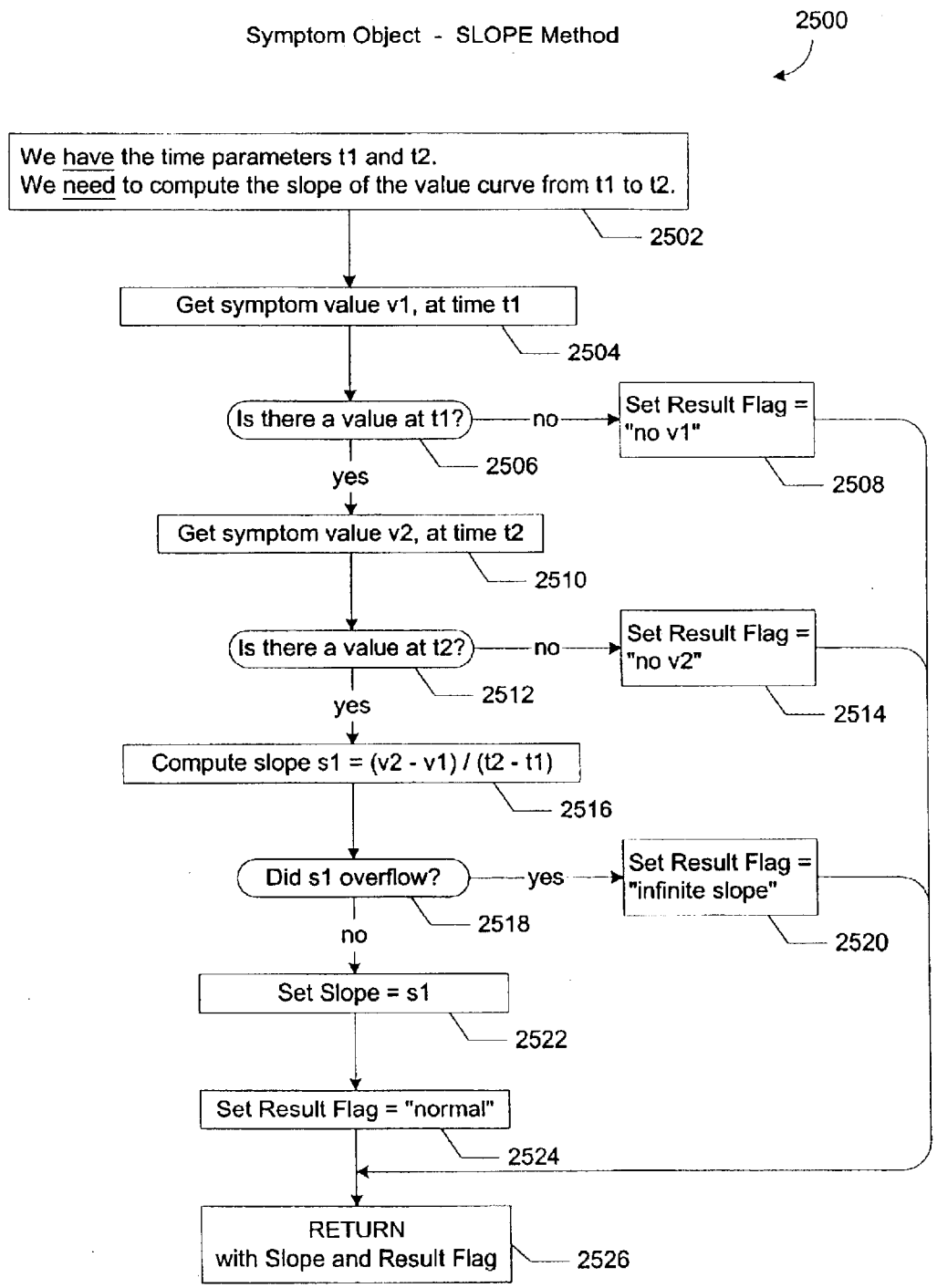
FIG. 25 is a flowchart of the Symptom Slope function shown in FIGS. 16 and 26.

Referring now to FIG. 25, the Slope function 2500 that computes the slope of two values with respect to time will be described. The slope of an angle is its tangent, and the time slope of two values v1 and v2 is $(v2-v1)/(t2-t1)$. When $t1=t2$, this value is arithmetically undefined, and when t1 approaches t2, it will raise overflow conditions in digital computers. This function uses an auxiliary result flag that is suitably coded to inform the caller about any special problems encountered during the calculation.

Function 2500 begins with entry state 2502, where the arguments t1, t2, v1, and v2 are assumed to be available to the function. Moving to state 2504, function 2500 examines data value v1. Proceeding to a decision state 2506, if no value v1 is given, function 2500 moves to state 2508. At state 2508, function 2500 sets the result flag to indicate "no value v1" and returns at return state 2526. But if, at decision state 2506, there is a value v1, function 2600 moves to state 2510 and retrieves data value v2. Moving to a decision state 2512, if no value v2 is given, function 2500 moves to state 2514, sets the result flag to indicate "no value v2" and then returns at state 2526. But if, at decision state 2512, there is a value v2, function 2500 moves to state 2516 and computes the tangent $(v2-v1)/(t2-t1)$. Continuing to a decision state 2518, if the result of state 2516 raised an overflow error condition, function 2500 moves to state 2520, sets the result flag to indicate "infinite slope" and returns at state 2526. But if, at decision state 2518, the result did not overflow, function 2500 moves to state 2522 and sets the result slope to the slope computed in state 2516. Moving to state 2524, function 2500 sets the result flag to indicate "normal slope". Moving to state 2526, function 2500 returns the result slope and flag to the function (2600, FIG. 26 or 1510, FIG. 16) that called it.

Figure 26:
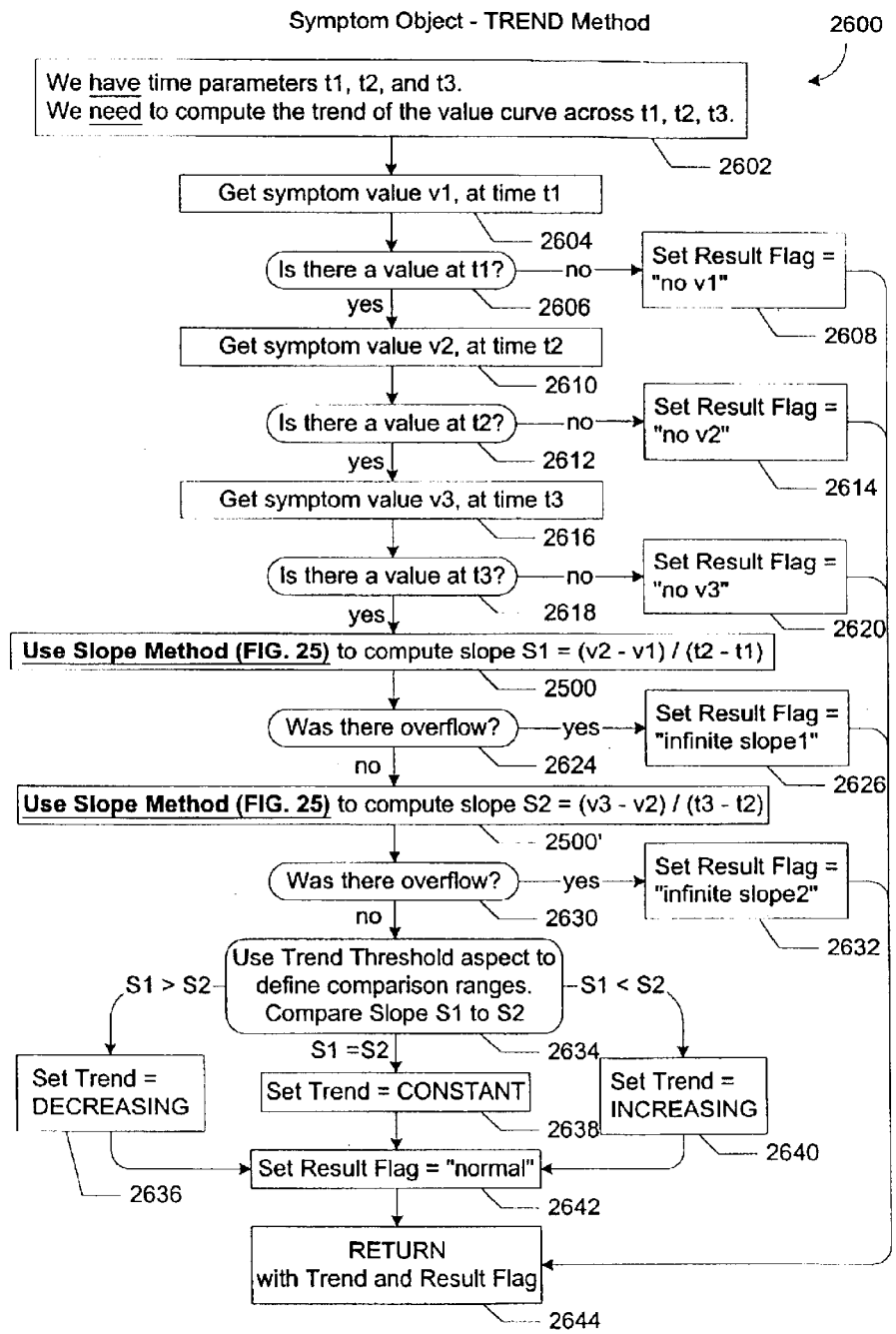
FIG. 26 is a flowchart of the Symptom Trend function shown in FIG. 17.

Referring now to FIG. 26, the Trend function 2600, which computes the trend of three points with respect to time, will be described. As computed here, the time trend has three possible values: DECREASING, CONSTANT, and INCREASING, depending on whether the slope from point 2 to point 3 is less than, equal to, or greater than the slope from point 1 to point 2, respectively. For various values of t1, t2, and t3, computing these slopes may be arithmetically undefined or raise overflow conditions in digital computers; the function uses an auxiliary result flag that is suitably coded to inform the caller about such special conditions encountered during the calculation.

The Trend function 2600 begins with entry state 2602, where the arguments t1, t2, t3, v1, v2, and v3 are assumed to be available to the function. Moving to state 2604, function 2600 examines data value v1. Advancing to a decision state 2606, if no value v1 is given, function 2600 moves to state 2608, sets the result flag to indicate "no value v1" and returns at return state 2644. But if, at decision state 2606, there is a value v1, function 2600 moves to state 2610 and retrieves data value v2. Moving to a decision state 2612, if no value v2 is given, function 2600 moves to state 2614, sets the result flag to indicate "no value v2" and returns at state 2644. But if, at decision state 2612, there is a value v2, function 2600 moves to state 2616 and retrieves data value v3. Moving to a decision state 2618, if no value v3 is given, function 2600 moves to state 2620, sets the result flag to indicate "no value v3" and returns at state 2644. But if, at decision state 2618, there is a value v3, function 2600 moves to execute function 2500 (FIG. 25).

At function 2500, the slope from point 1 to point 2 is computed as $(v2-v1)/(t2-t1)$. Moving to a decision state 2624, if the result of executing function 2500 raised an overflow error condition, function 2600 moves to state 2626. At state 2626, function 2600 sets the result flag to indicate "infinite slope 1" and returns at state 2644. But if, at decision state 2624, the result did not overflow, function 2600 moves to execute function 2500' (FIG. 25). At function 2500', the slope from point 2 to point 3 is computed as $(v3-v2)/(t3-t2)$. Moving to a decision state 2630, if the result of function 2500' raised an overflow error condition, function 2600 moves to state 2632. At state 2632, function 2600 sets the result flag to indicate "infinite slope 2" and returns at state 2644. But if, at decision state 2630, the result did not overflow, function 2600 moves to a decision state 2634 and compares slope 1 to slope 2, using predefined comparison ranges. If, at decision state 2634, slope 1 is greater than slope 2, function 2600 moves to state 2636; if slope 1 is less than slope 2, function 2600 moves to state 2640; if slope 1 is equal to slope 2, function 2600 moves to state 2638. At state 2636, function 2600 sets the result trend to indicate a decreasing trend, and then moves to state 2642. At state 2638, function 2600 sets the result trend to indicate a constant trend, and then moves to state 2642. At state 2640, function 2600 sets the result trend to indicate an increasing trend, and then moves to state 2642. At state 2642, function 2600 sets the result flag to indicate a normal result. Moving to state 2644, function 2600 returns the computed trend and the result flag to the calling function 1520 (FIG. 17).

Referring to FIG. 27, a simple conceptual way of showing the use of actual and alternative symptom weights in arriving at a diagnostic score will now be described. Although the actual implementation may differ, the diagram illustrates the relationships among the diseases, symptoms and weights. In one embodiment, a disease-symptom matrix is used where a plurality of diseases are listed in the columns and a plurality of related symptoms are listed in the rows. In a partial exemplary headache disease-symptom matrix 2700, the column 2702 lists symptoms in the rows marked as 2732 and at 2742. Several exemplary diseases are shown at the columns marked as 2704 (common migraine), 2706 (classic migraine), 2708 (cluster headache), and 2710 (subarachnoid hemorrhage). For each disease, there is a column for holding an "actual" value (columns 2714, 2716, 2718, and 2720) or an "alternative" value (columns 2715, 2717, 2719, 2721). As described above, a consultation begins in HAI mode in the area marked 2730. Questions to elicit exemplary symptoms in the area marked 2732 are asked of the patient. As questions associated with the symptoms are asked of the patient, a value for the particular symptom is placed in either the actual column or the alternative column for each applicable disease as assigned by the author of a particular disease. For example, a symptom "Nausea2" is defined by the author of Common Migraine to be an "actual" symptom and has a value of 35 as determined by the answer of the patient. However, the symptom "Nausea2" is defined by the author of Cluster Headache to be an "alternative" symptom and has a value of −20 as determined by the answer of the patient. Therefore, while in HAI mode, some diseases will have actual symptoms elicited and some diseases will have alternative symptoms elicited.

After one of several possible criteria is reached, the mode is switched from HAI mode (2730) to VAI mode (2740) by the system, such as shown at 2734. From that point forward, the system concentrates on asking the symptoms for a focus disease based on reaching the criteria. In one embodiment, the "actual" symptoms for the focus disease (classic migraine in this example) are then elicited as shown at 2742. For example, the criteria may include the fact that a particular diagnostic score is reached or passed, a particular diagnostic momentum is achieved, a probability of diagnosis is achieved, or the user may ask to switch modes. The user may request to have the actual symptoms for the focus disease to be elicited, or even have the system go back and re-ask only the actual symptoms for the focus disease as shown at 2744. Other weights (not shown), such as for various types of synergies, are added in for the diseases in the area marked 2746. The exemplary diagnostic scores for each disease column are shown at row 2750 and a total score for each disease, which sums the actual and alternative scores for each disease, is shown in row 2752. A diagnosis may be declared for a disease having a total score that meets or exceeds a particular threshold. In this example, the system diagnoses the patient as having classic migraine, with a score of 480.

Referring now to FIG. 28, this figure depicts a form or screen display that lets a patient arrange a set of symptoms into the time order in which they actually occurred in the patient. This is one embodiment that uses a graphic user interface and input form to obtain the patient's input. Other embodiments use other techniques to obtain the same information from the patient. In the diagnostic loop 100 (FIG. 1), the system uses a valuator object (FIG. 6) to obtain the patient's disease timeline as a value. The valuator object then builds a time profile of the patient's symptoms, compares it to time profiles previously stored in a database, and adds extra diagnostic weight to diseases that match the patient (FIG. 20). In another part of the diagnostic loop, the patient's disease timeline profile can be used, by well-known pattern matching techniques, to filter the candidate disease list and thus reduce it to the most likely candidate diseases (FIG. 3). In another part of the diagnostic loop, the patient's disease timeline can be used to identify the First Significant Symptom (FIG. 13). In another part of the diagnostic loop, the patient's disease timeline can be used to select a disease that closely matches the patient time profile as the next focus disease (FIG. 4). Disease timelines, therefore, can be used to both reduce the set of candidate diseases as well as to help diagnose a particular candidate disease.

FIG. 28 shows a chart 2800 that plots symptom onset and duration against time for four different symptoms. The time scale (line 2810) is shown in hours and runs from left to right, so that symptoms that appear earlier are placed more to the left than symptoms that occur later. As an example, four symptoms (Anorexia, Nausea, Epigastric Pain, and Right-Lower-Quadrant Pain) are shown to depict the chronological sequence in which they typically appear in the disease Appendicitis. Other diseases may, of course, also exhibit this same time line or time profile of symptoms. The chart shows (line 2812) that classic Appendicitis typically begins with Anorexia (loss of appetite), which is therefore placed at the very left of the time line, to mark the origin or start of the disease process in the patient. One hour after the onset of Anorexia, a patient with Appendicitis will typically experience Nausea, which is therefore shown as starting at the 1-hour mark (line 2814). About 2.5 hours into the disease, a patient will typically experience Epigastric Pain (discomfort in the stomach area), and so that symptom is shown (line 2816) as starting between time 2 and 3 on the time scale. Similarly, RLQ Pain (pain in the right lower quarter of the abdomen) is shown as beginning about 4 hours after the disease starts (line 2818). Assuming that the patient has previously indicated the presence of the symptoms Anorexia, Nausea, Epigastric Pain, and RLQ Pain, the diagnostic system offers this type of chart to the patient. The patient then uses a mouse to move the symptom blocks left and right until they are in a position that indicates when they appeared. The blocks themselves can be stretched or shrunk to indicate how long they lasted. Then the patient submits the selections by clicking on a Submit (or similar) button 2820.

Figure 29A:
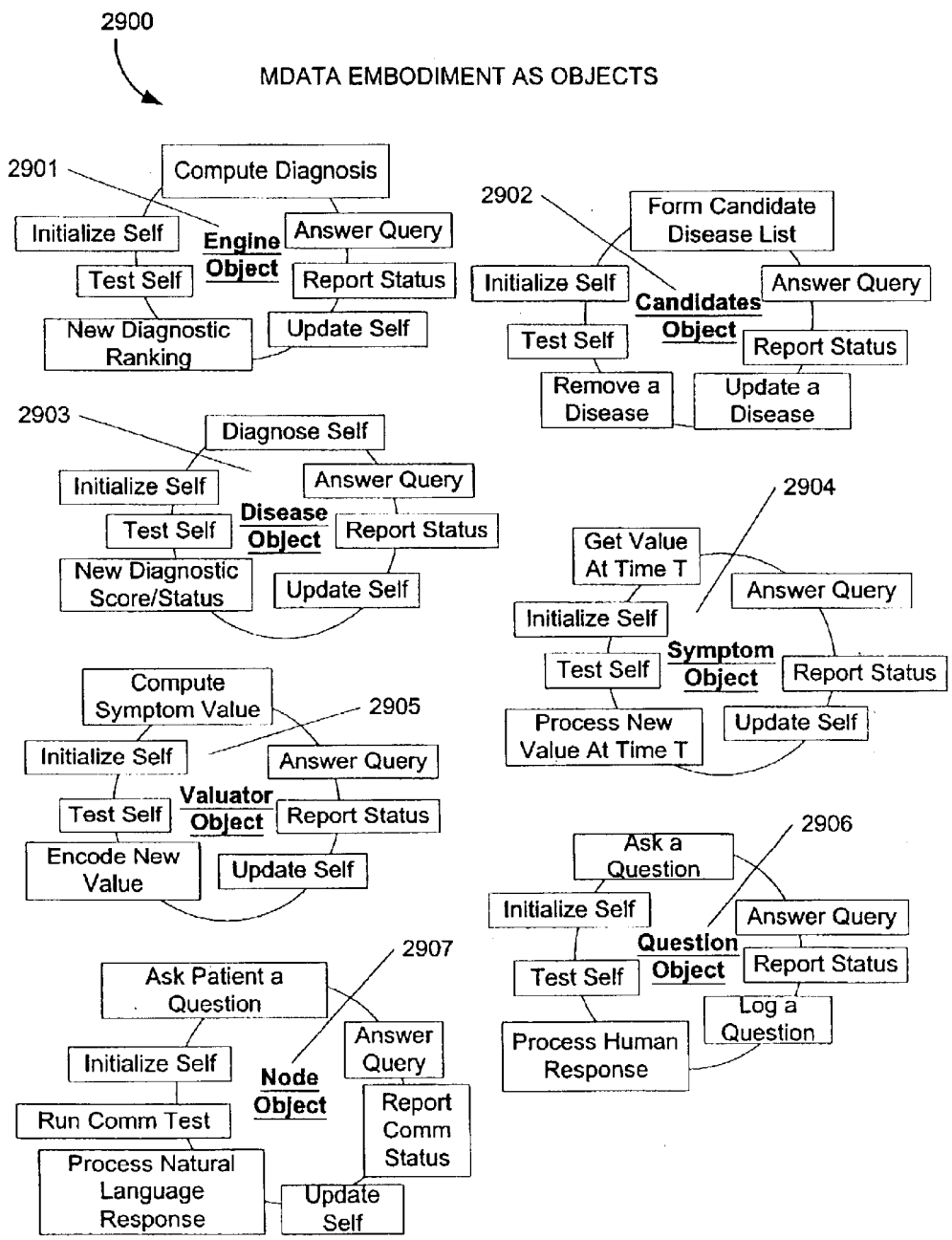
FIG. 29a is a diagram of one configuration of objects used by an embodiment of the medical diagnostic and treatment advice system.

Referring now to FIG. 29a, an object embodiment 2900 of the entire MDATA system using techniques of object-oriented programming, i.e., as a collection of software objects that are capable of diagnosing a patient. In this embodiment 2900, all data is converted into "objects" by surrounding the data (now called "members") with software procedures and functions (now called "methods") that manipulate and maintain the data. Programs outside of the object are only permitted to access member data by using an object method or by special permission. This object-oriented embodiment represents a rearrangement and redistribution of data and processes that has several benefits. First, the object-oriented embodiment guarantees the validity of the object's data, data formats, and data structures at all times, regardless of the unpredictable dynamics of the surrounding diagnostic environment. Second, each object of a system can accumulate data, thus tracking both its own processing history and that of its neighboring objects. It can therefore assess its current status, compare itself to other objects, and acquire an awareness that it can use to make intelligent decisions. Third, given a memory, an awareness, and methods for acting on its environment permits an object to be used as an agent that can act independently to perform a task which is useful to the system as a whole.

The object-oriented embodiment is well known in the programming industry, but is used here in a novel and non-obvious manner to perform automated medical diagnosis. In other diagnostic systems, diseases and objects are treated as inanimate data records that are manipulated by a central program to compute a diagnosis. In the embodiment described in FIGS. 29a and 29b, diseases and symptoms are designed as objects that can behave as intelligent actors that organize themselves at various logical levels, cooperate competitively for diagnosis, and ultimately sort themselves into a differential diagnosis. For the purpose of illustration, a software object is represented as a simple circle that is assumed to encapsulate all of the object's data, and several rectangles that represent object functions that belong to the object but can be accessed by the outside world. Seen as such, a software object can be used as a "smart data record" that can act independently of other objects and can retain a memory of its actions for future reference.

FIG. 29a shows several such objects, as they would be designed to participate in the object embodiment 2900 of the MDATA system. Object 2901 may represent a portion of the system, e.g., the list-based engine, whose actions are detailed in FIGS. 1 to 26. The functions performed by the system in the object embodiment are shown grouped around the object. For example, the function INITIALIZE SELF would be called by the external system to cause the system to prepare for a diagnostic session, and the function REPORT STATUS would be called by any process requiring some information about the current status of the system. Object 2902 represents the Candidate Disease List; its functions perform services related to that list. For example, the function FORM CANDIDATE DISEASE LIST would be called by the system object to begin a diagnostic session as shown in FIG. 2. Object 2903 is a Disease Object, which represents all of the medical knowledge the system has about a single disease. Its functions provide services related to diseases, such as performing a diagnosis or updating itself with a new diagnostic score. Object 2904 is a Symptom Object, which represents the data and functions related to a single symptom. For example, one of its functions is to GET VALUE AT TIME T, which activates the appropriate valuator functions needed to obtain a value, by computation, table lookup, or questioning of the patient. Object 2905 is a Valuator Object, whose role is to perform the detailed actions required to obtain a value. Object 2906 is a Question Object, which handles the tasks required to question a human patient. Object 2907 is a Node Object, whose role is to handle the actual interface between the digital computer and the human patient. In one embodiment, the node object is the only object in the entire MDATA system that actually communicates with the patient.

Figure 29B:
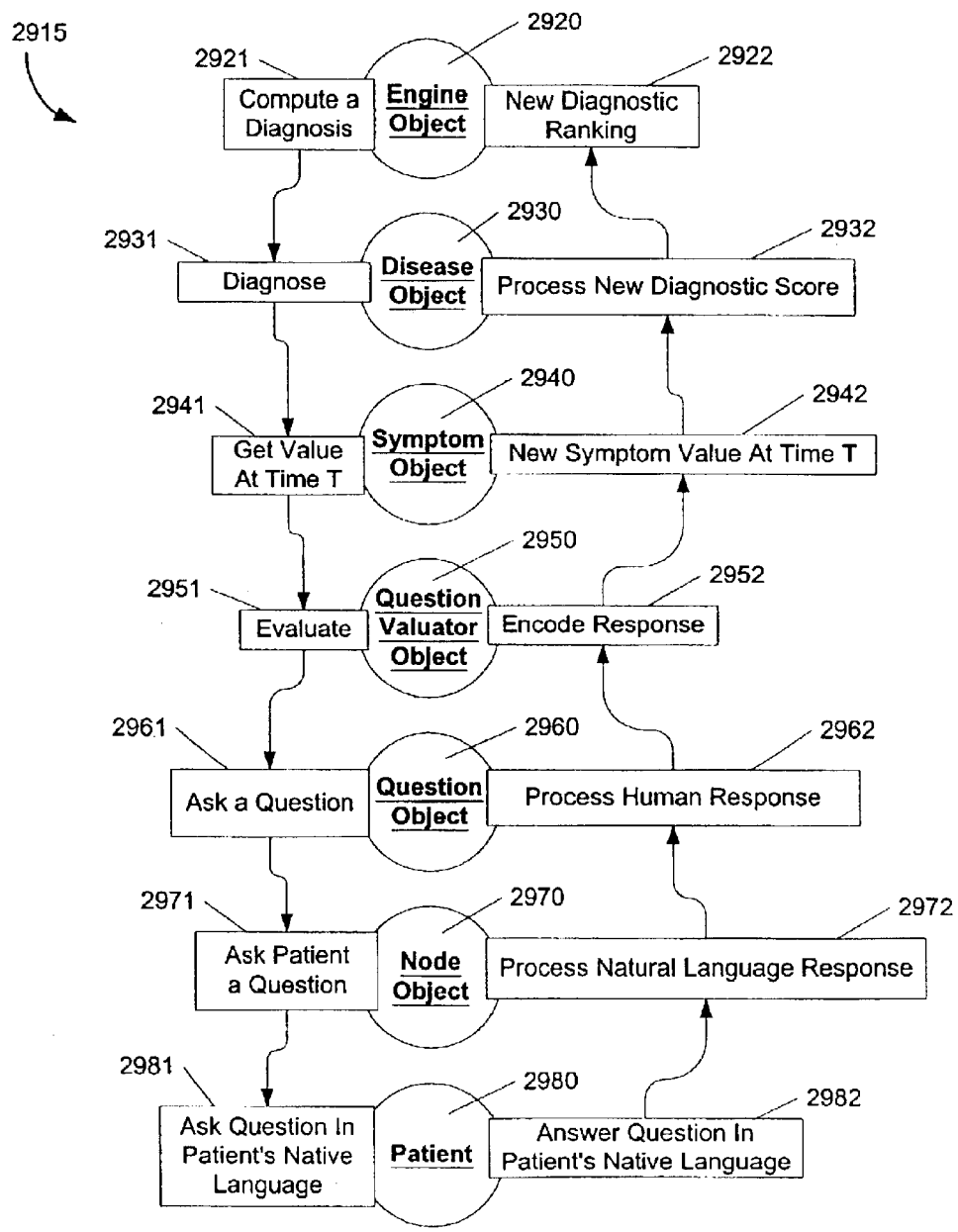
FIG. 29b is a diagram of an exemplary on-line use of the configuration of objects shown in FIG. 29a to develop a diagnosis.

Referring now to FIG. 29b, an object-oriented embodiment of how the MDATA system (FIG. 29a) might use a collection of objects to perform a single iteration of the Diagnostic Loop (FIG. 1) will be abstractly described. Instead of using a single program or engine that contains a set of central functions that perform operations on data (FIG. 1), the object-oriented embodiment of FIG. 29b uses functions distributed as 'methods' into various objects that either perform the functions themselves or delegate operations to still other objects. For example, whereas in FIG. 1, the system calls a function to select the next focus symptom, in FIG. 29b, it is the current disease object that selects the next symptom.

In general, each object performs its own tasks and calls upon other objects to perform their tasks at the appropriate time. Over time, the sequence of operations creates a natural task hierarchy, from higher to lower levels of detail, using as many or as few levels as is required to perform the main task. At the same time, the hierarchy represents logical interpretations and meanings at different levels. Thus, at the lowest level, a patient is answering a single question; at the middle level, this is interpreted as a change in symptom information about the patient; at the highest level, it may result in a reranking of the tentative diagnosis of several competing diseases.

The ability to capture and embody the complex interpretive and analytical tasks of medical diagnosis into software is what gives the MDATA design a major advantage over other automated diagnostic systems, which tend to operate at a single level of action and meaning. What is gained by the object embodiment is the self-organizing and self-assessment ability that emerges from a system whose data are allowed to have the autonomy to organize themselves, based on certain globally controlling principles.

FIG. 29b summarizes a process 2915 that may take place in an object-oriented embodiment of the MDATA system in order to perform the same processes that are detailed in FIGS. 1 through 26, with the added complication that questions are posed to an on-line patient in the patient's native language or other desired language, for example, French. The process 2915 starts when an external process has assembled a set of candidate diseases and now calls method 2921 to compute a differential diagnosis based on the candidate diseases. Note that the further processing by the system occurs to output a particular diagnosis. Method 2921 is one of many method functions of Engine Object 2920. Engine Object 2920 encapsulates all data and processes of at least a portion of the system and its numerous methods, of which only methods 2921 and 2922 are shown here for illustration. The main purpose of the Engine Object is to accept external system and user requests and initiate the appropriate internal processing. At the appropriate time, process 2915 advances to method 2931, which is a method of a Disease Object 2930. Disease Object 2930 encapsulates all data and processes of a typical Disease Object. It has numerous methods; only methods 2931 and 2932 are shown here for illustration. A Disease Object represents all that is known about one given medical disease; its main function is to accept requests for disease information and to carry out external requests for action. In the case being illustrated, the Disease Object 2930 selects one of its Symptom Objects and moves to method 2941 to obtain the value of that symptom in the on-line patient. Symptom Object 2940 contains all data and processes of a typical Symptom Object, with many methods of which only methods 2941 and 2942 are shown here for illustration. A Symptom Object represents all that is known about one given symptom; its main function is to accept requests for symptom information. The Symptom Object initiates internal processing to obtain actual symptom values and proceeds to method 2951.

Method 2951 is one method of a Question Valuator Object 2950. Valuator Object 2950 has numerous methods, but only methods 2951 and 2952 are shown here. In general, a Valuator Object is responsible for performing the computations required to compute the value of a symptom at some time t. A question valuator object initializes the processing required to select and ask a human questions and then advances to method 2961. Method 2961 is a method of Question Object 2960, which represents the members and methods of a typical Question Object and its many methods, of which only methods 2961 and 2962 are shown here. A Question Object represents all of the data involved in asking a human a question, such as the natural language to be used or the education level of the patient. The object's main function is to handle the stream of detailed questions that are usually required to pose a question and elicit a valid response from a human. This question object selects the node objects that are written to display questions in the patient's native language. Process 2915 then moves to method 2971 of Node Object 2970. Node Object 2970 encapsulates all data and processes of a typical node object and its methods (only methods 2971 and 2972 are shown here). This node object handles the physical details of a single question/response exchange between a human and a computer, including special hardware, video, and audio problems, time delays, time-outs, and any need to repeat. The Node Object initiates the requisite processing, and then moves to method 2981. Method 2981 asks a question of a patient who may be accessing the system over a data communications network, the Internet, for example. Assuming a GUI embodiment, the question will be displayed on a screen as a dialog, with appropriate buttons for a response from the patient via a patient object 2980.

When the patient responds at state 2982, a reverse sequence of methods begins as the process 2915 backs up the object hierarchy. From state 2982, process 2915 moves to method 2972, where the patient's response is noted and time-stamped. Proceeding to method 2962, the response is noted as the final response in a possible question stream. Moving to method 2952, the response is encoded for internal processing, so that it loses its native language aspect here. Moving to method 2942, the response is processed as a new symptom value at time t. Moving to method 2932, the response is processed as an increment in the disease's diagnostic score. Moving to method 2922, the response activates a reranking of the relative disease positions in a differential diagnosis and then performs thresholding to determine a diagnosis. Finally, the engine object 2920 can now repeat the process or terminate, depending on the external option settings. Other functions and objects associated with the LBE which are expected before, during or after this control flow may be included in various embodiments. For instance, once a disease ranking is computed, thresholding may occur to determine a diagnosis of one disease. Furthermore, actions may occur such as updating a patient's electronic medical record or notifying a doctor or other healthcare practitioner of a diagnostic event, e.g., a situation requiring immediate treatment.

Figure 30:
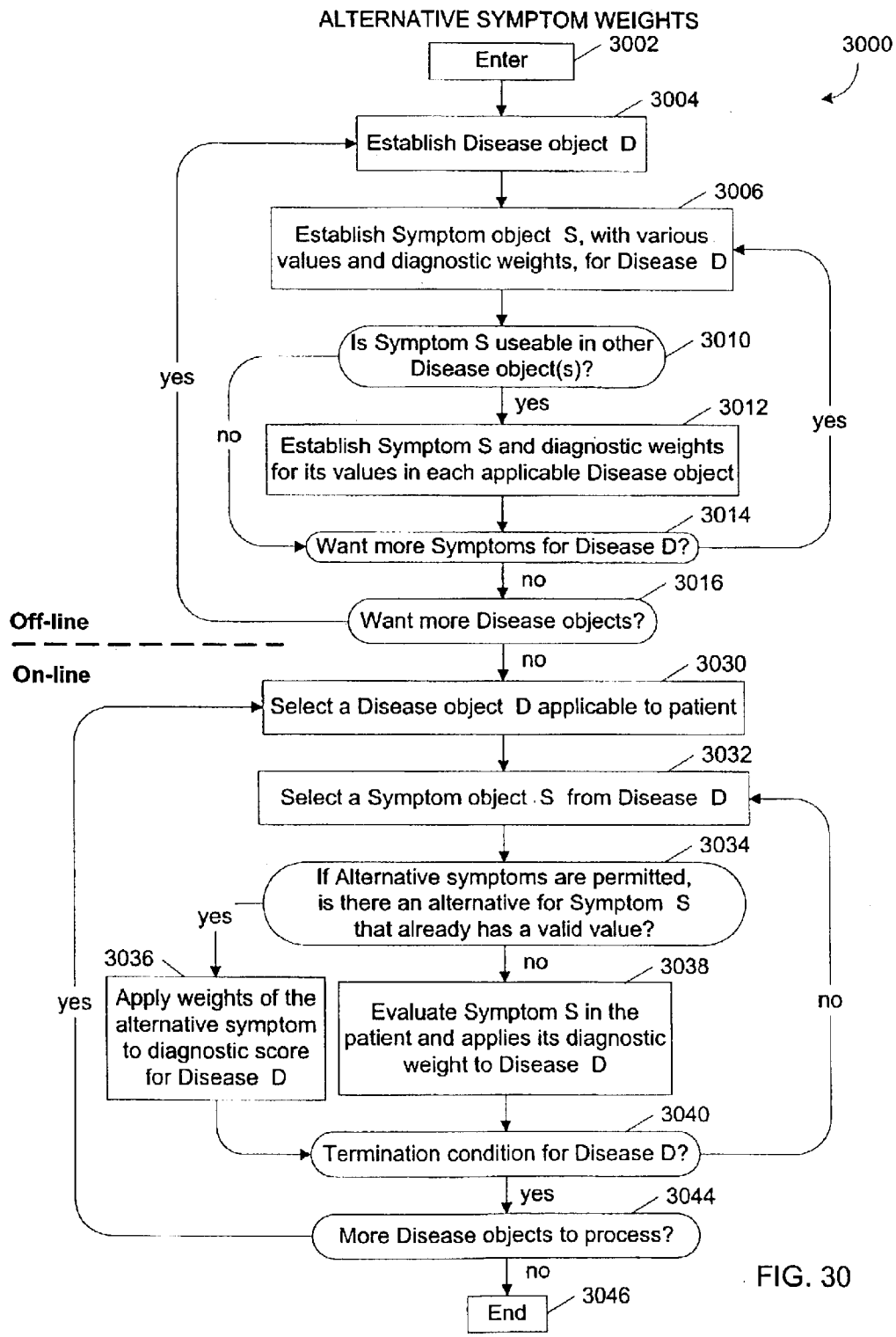
FIG. 30 is a flowchart of an alternative symptom weights feature of the medical diagnostic and treatment advice system.

Referring now to FIG. 30, a process 3000 describes how alternative symptoms are established in an off-line preparation mode and later used to diagnose a patient in an on-line mode. The off-line and on-line modes are shown here as if they occur in sequence; but in practice they are typically separated by additional preparation steps such as testing, approval, auditing, and final integration into a production database.

Process 3000 begins at state 3002, where one or more disease objects are to be created by a medical author. Moving to state 3004, one disease object D is established by defining its member functions and data. One major data structure of disease D is the list of symptoms that characterize the disease. Each symptom S of that list must be defined and described. Moving to state 3006, one symptom S of the list is established and defined in terms of its values and their diagnostic weights. Moving to a decision state 3010, if the symptom object can perhaps be used as alternative symptoms in other disease objects, the diagram moves to state 3012; otherwise it moves to a decision state 3014. At state 3012, the symptom is established as an alternative symptom in the applicable disease objects. Moving to decision state 3014, if there are more symptom objects to be established for disease D, the diagram moves back to state 3006; otherwise it moves to a decision state 3016. At decision state 3016, if there are more disease objects to be established, the diagram moves back to state 3004; otherwise it terminates the off-line phase.

For the on-line phase, process 3000 describes how alternative symptoms are processed inside the diagnostic loop 100 during an automated diagnostic session with a patient (or a patient's agent) who is on-line and able to respond to questions posed by the system (FIG. 1). Moving to state 3030, a disease D is selected as the focus for diagnosis (FIG. 4). Moving to state 3032, one symptom object S of disease D is selected as the focus for diagnosis (FIG. 5). Symptom S must now be evaluated, which may be a complex, time-consuming process (FIG. 6). Moving to a decision state 3034, process 3000 shows a portion of the evaluation process that deals with the use of alternative symptoms, which are used to save on-line time. It may be the case that, for disease D, symptom S has an acceptable alternative symptom that has already been evaluated. If so, the diagram bypasses evaluation of symptom S and instead moves to state 3036. But if, at decision state 3034, there is no alternative symptom, process 3000 moves to state 3038 for evaluation of symptom S. At state 3036, the weights of the alternative to symptom S are retrieved and applied to the diagnostic score of disease D, and then process 3000 moves to a decision state 3040. However, at state 3038, symptom S is evaluated (FIG. 6), the diagnostic weights of symptom S are retrieved and applied to the diagnostic score of disease D (FIGS. 11 and 21), and then process 3000 moves to state 3040. At state 3040, if some terminating condition is reached for disease D (FIG. 22), process 3000 moves to a decision state 3044; else it moves to state 3032. At decision state 3044, if there are other disease objects to process, process 3000 moves back to state 3030; otherwise it moves to the end state 3046.

Figure 31:
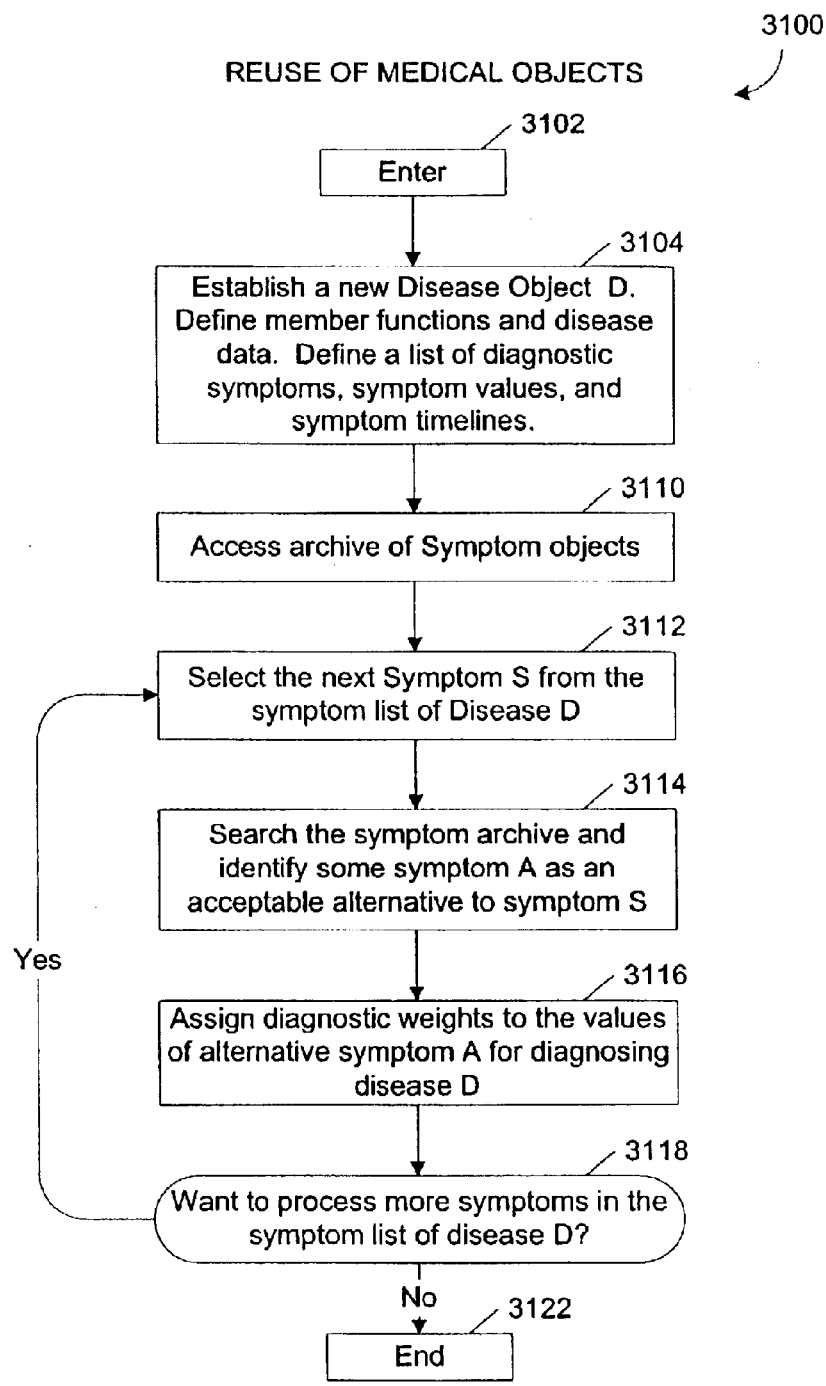
FIG. 31 is a flowchart of a reuse of medical objects feature of the medical diagnostic and treatment advice system.

Referring now to FIG. 31, a process 3100 describes how symptom objects can be re-used as alternative symptoms in a disease object. The Alternative Symptoms feature allows the diagnostic system to substitute specified symptom values for others in order to bypass time-consuming evaluation of a given symptom when acceptable alternative symptom values are already available. The feature accommodates the individual preferences of medical authors, simplifies the processing of symptoms stored in various equivalent formats, and allows the sequencing of symptom evaluation to be more adaptive to the dynamics of an on-line diagnostic session, instead of depending on prescribed sequence of symptom evaluation.

Process 3100 only shows the general steps of the off-line preparation of one disease object. How the disease is diagnosed on-line is shown in FIG. 1, and how alternative symptoms are used is described in conjunction with FIGS. 6 and 30. Process 3100 begins at state 3102, where an author wants to create and describe a disease object D. Moving to state 3104, the disease object D is established and its member functions and data are defined. One major data structure of disease D is the list of symptoms, symptom values, and symptom timelines that characterize the disease. Each symptom of that list is identified and described. Moving to state 3110, a database of all existing symptom objects is accessed for the purpose of locating possible alternative symptoms. Advancing to state 3112, one symptom S of disease D's symptom list is selected. Proceeding to state 3114, the symptom database is searched, and some symptom A is identified as an acceptable alternative to symptom S for diagnosing the disease D. Moving to state 3116, diagnostic weights are assigned to the values of alternative symptom A. Moving to a decision state 3118, if more symptoms of disease D are to be processed, process 3100 moves back to state 3112; otherwise it moves to end state 3122.

Figure 32A:
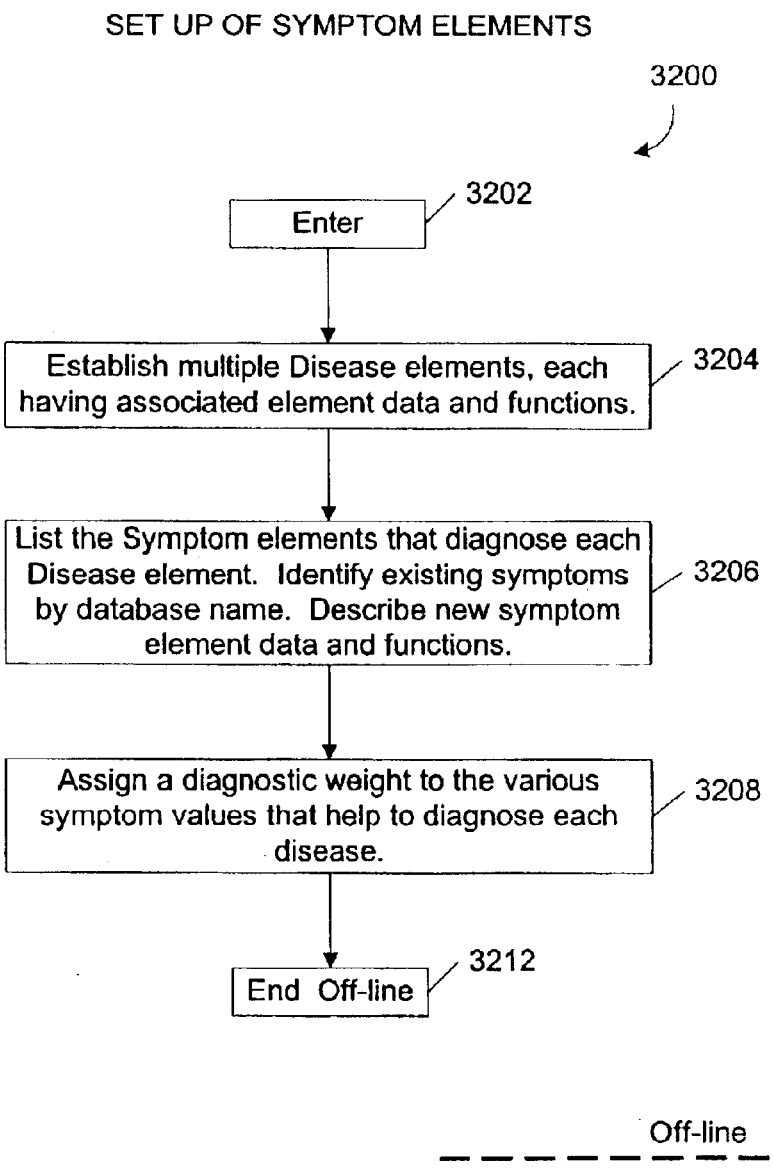
FIG. 32a is a flowchart of a setup of symptom elements aspect of the medical diagnostic and treatment advice system.

Referring now to FIG. 32a, a process 3200 used by an author to establish disease and symptom objects or elements will be described. Note that the diagram shows processing that is performed off-line, at data preparation and testing time, and not on-line at diagnostic time.

Process 3200 begins at state 3202, where the author wants to define one or more disease objects and their symptom objects. Moving to state 3204, multiple disease objects are established, each with the requisite disease object data and disease object processing functions. Proceeding to state 3206, multiple symptom objects are identified for each disease object. Symptoms that already exist in a symptom database are identified. New symptoms are described, including a list of their possible values. Advancing to state 3208, a diagnostic weight is assigned to some or all values of each symptom object. Each symptom object typically has many possible values, and each value may have an assigned diagnostic weight toward the diagnosis of its associated disease. Moving to state 3212, process 3200 ends the off-line portion at state 3212.

Figure 32B:
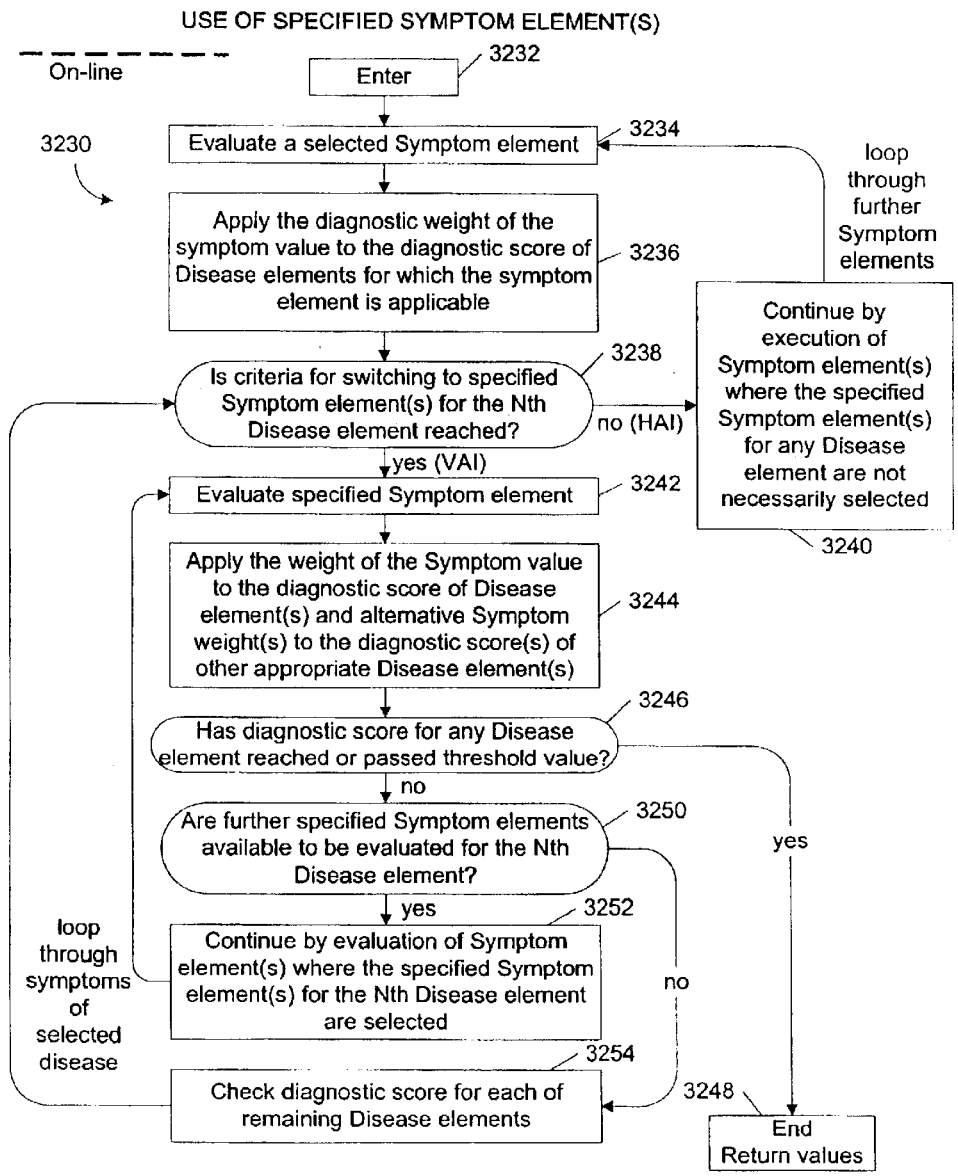

Referring to FIG. 32b, one embodiment of the use of specified symptom elements or objects for disease elements or objects will now be described by on-line process 3230. The off-line portion (process 3200) was previously described in conjunction with FIG. 32a. Process 3230 illustrates one embodiment of the HAI and VAI concepts along with the use of specified symptom elements.

Process 3230 begins at an enter state 3232 in the HAI mode previously described. Process 3230 advances to state 3234 where a selected symptom element is evaluated, such as performed by the Obtain Symptom Value function 140 (FIG. 6). Proceeding to state 3236, process 3230 applies the diagnostic weight of the symptom value to the diagnostic score of disease elements for which the symptom element is applicable. Moving to a decision state 3238, process 3230 determines if the criteria for switching to the evaluation of specified symptom elements (i.e., in the VAI mode) for one of the disease elements (the Nth disease element) is reached. Examples of criteria are a high diagnostic momentum, a high diagnostic score, a high diagnostic probability, some external process requested the switch or a human requested the switch to the use of specified symptoms. If the criteria is not reached at decision state 3238, process 3230 proceeds to state 3240 to continue evaluation of symptom elements where the specified symptom elements for any disease element are not necessarily selected. Process 3230 moves back to state 3234 to loop through further symptom elements until the criteria at decision state 3238 is reached.

If the criteria is reached at decision state 3238, process 3230 proceeds in the VAI mode to state 3242 where a specified symptom element for the Nth disease element is evaluated. Continuing at state 3244, process 3230 applies the weight of the evaluated symptom element to the diagnostic score of the Nth disease (and any other disease for which it is a specified symptom element) and alternative symptom weight(s) to the diagnostic score(s) of other appropriate disease element(s). Advancing to a decision state 3246, process 3230 determines if the diagnostic score for any disease element has reached or passed a threshold for diagnosis. If so, the diagnostic scores for the relevant diseases (those being currently evaluated) are returned at end state 3248. If the diagnostic score for any disease element has not reached or passed the threshold, as determined at decision state 3246, process 3230 proceeds to a decision state 3250 to determine if further specified symptom elements are available to be evaluated for the Nth disease element. If so, process 3230 continues at state 3252 to continue evaluation of symptom elements where the specified symptom elements for the Nth disease element are selected. Process 3230 moves back to state 3242 to loop through specified symptom elements of the Nth disease until there are no further specified symptom elements available, as determined at decision state 3250. When decision state 3250 determines there are no further specified symptom elements available, process 3230 advances to state 3254 to check the diagnostic score for each of the remaining disease that are currently being evaluated. Process 3230 then moves back to decision state 3238 to determine if the VAI mode should be established any other disease element or if further processing should continue in HAI mode, as previously described.

Figure 33:
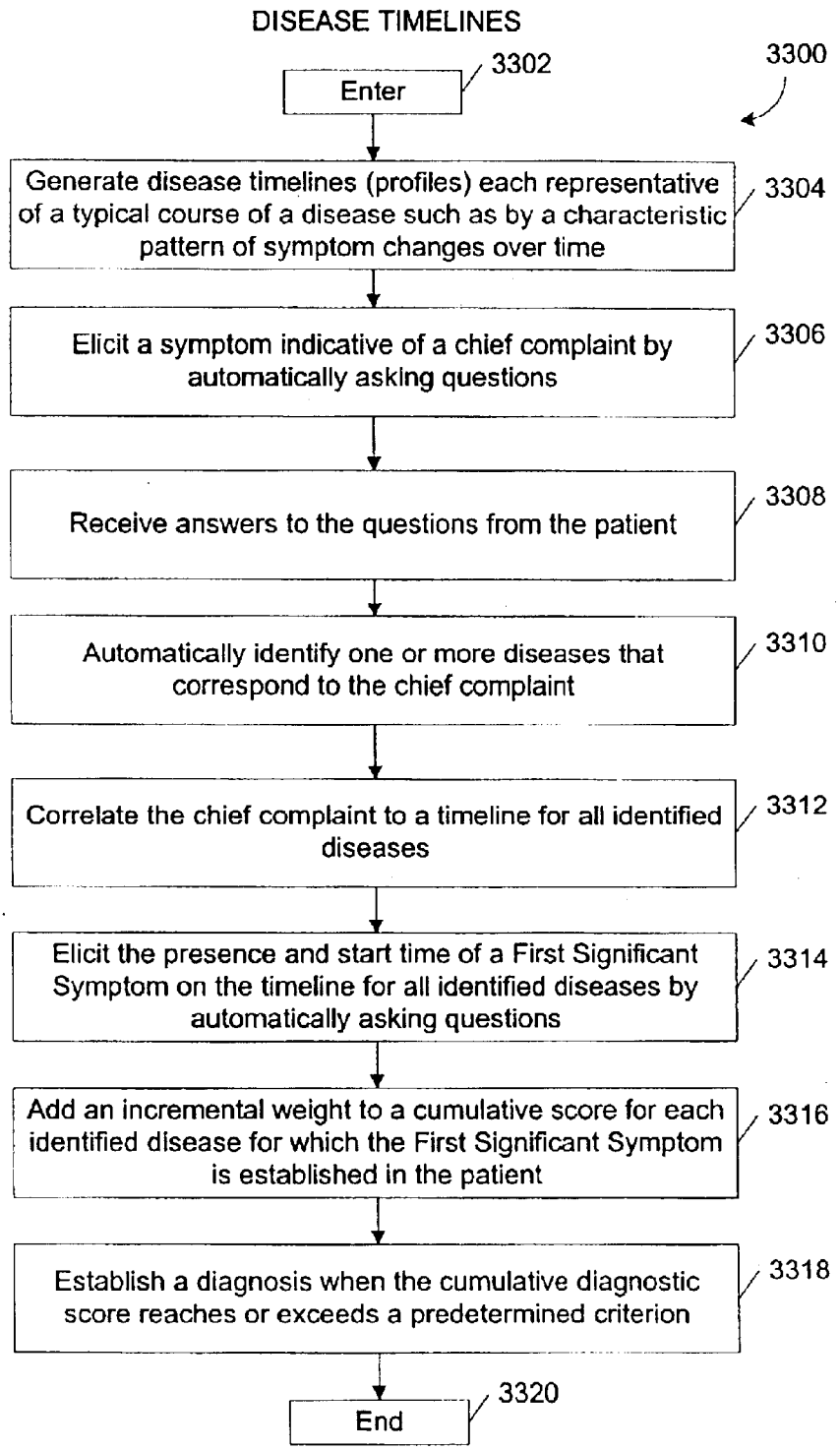
FIG. 33 is a flowchart of one embodiment of a disease timelines aspect of the medical diagnostic and treatment advice system.

Referring now to FIG. 33, a process 3300 summarizes the major steps of a fully automated method that uses the novel concept of disease timeline matching to diagnose a patient's medical condition. A disease timeline is a data structure that records the symptoms of a specific disease in chronological order and describes the key symptom characteristics such as onset, duration, magnitude, and offset of each symptom. Disease timelines can be generic or actual. Generic timelines describe the disease statistically, as it evolves in a typical population; actual timelines describe the symptoms of a specific patient being diagnosed. Timelines are abstract data structures that can be represented in various ways such as graphs, charts, calendars, lists, tables, spreadsheets, or software objects. A simple example is an hour-by-hour description of a disease process in the form of a Gantt Chart, as shown in FIG. 28.

The diagnostic process 3300 outlined in FIG. 33 exploits the fact that it is possible to take an actual disease timeline, use well-known mathematical techniques to match it to a database of generic disease timelines, and thus identify a relatively small set of diseases that are strong candidates for further analysis and ultimate diagnostic ranking. As outlined in FIG. 33, the process has two separate phases. In the first phase (states 3302 to 3304), a computer program assists physician authors as they prepare a database of generic disease timelines. In the second phase (states 3306 to 3320), another program uses various symptom characteristics to match the timeline of an on-line patient to the generic timelines in the database and to appropriately increment the diagnostic score of matching diseases.

State 3302 is the start of the process 3300. Moving to state 3304, using an off-line program, medical authors generate a database of generic disease timelines. This state may represent several years of professional labor to generate a massive database of thousands of diseases and their symptoms. It may also include further extensive labor to format and test the data and to prepare it for use in a fully automated diagnostic system such as described in states 3306 through 3320.

Proceeding to state 3306, a patient is on-line to a computer program which elicits a chief complaint from a patient by asking questions. Moving to state 3308, the program receives answers from the patient. Advancing to state 3310, the program uses the responses to identify one or more diseases that correspond to the chief complaint. Moving to state 3312, the program correlates the chief complaint to a timeline for all identified diseases.

Continuing at state 3314, the program asks the patient questions to determine the patient's FSS time parameters and locates this on the disease timeline. Moving to state 3316, the program adds a pre-determined incremental diagnostic weight to the diagnostic score of all identified diseases if the patient's FSS matches the disease FSS. Proceeding to state 3318, the program establishes a diagnosis for one or more of the identified diseases when its cumulative diagnostic score reaches or exceeds a threshold. The process 3300 ends at state 3320.

Figure 34:
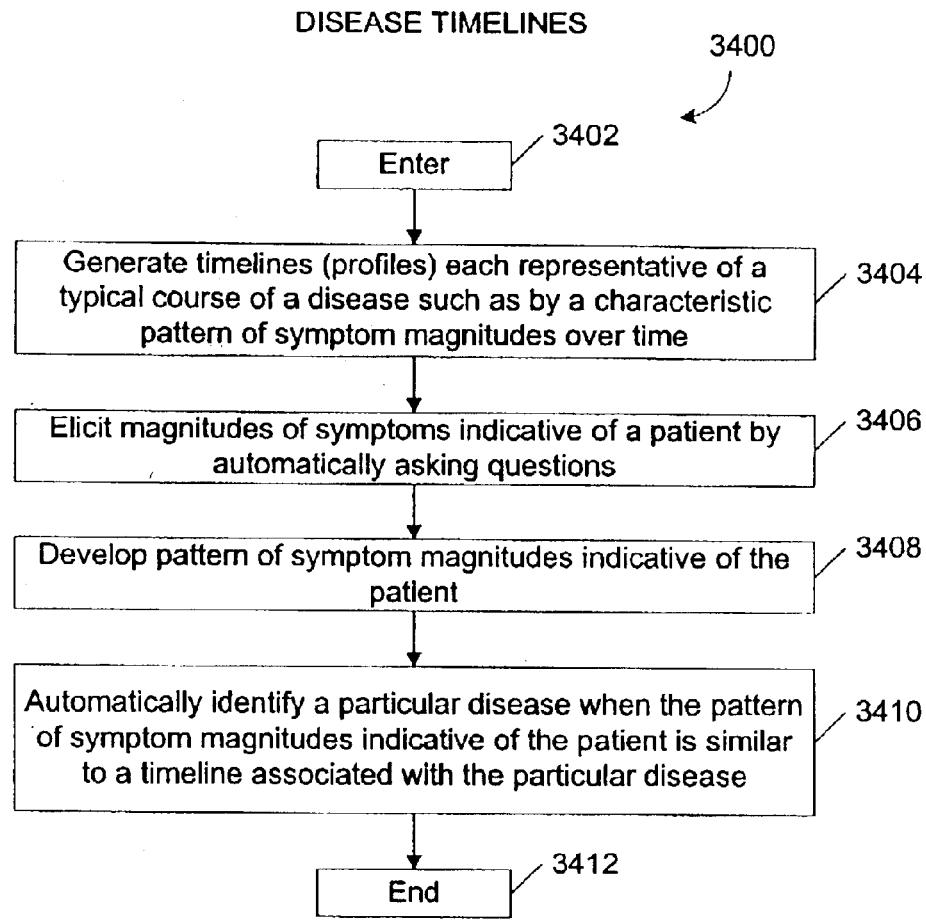
FIG. 34 is a flowchart of another embodiment of a disease timelines aspect of the medical diagnostic and treatment advice system.

Referring now to FIG. 34, a fully automated process 3400 that diagnoses a patient's medical condition using symptom magnitude patterns, which identify the changes in magnitudes of each symptoms of a specific disease in chronological order, will be described. A magnitude pattern is, in effect, a disease timeline with magnitudes of the symptoms, creating a disease profile. Like a disease timeline, a symptom magnitude pattern can be can be generic or actual, i.e., typical or patient-specific.

Process 3400 begins at state 3402. Moving to state 3404, using an off-line program, medical authors generate a database of generic symptom magnitude patterns, analogous to the disease timelines described for FIG. 33. Proceeding to state 3406, a computer program asks an on-line patient questions to elicit the magnitude of the patient's symptom.

Continuing at state 3408, the program develops a pattern or profile of the patient's symptoms and their magnitudes. Moving to state 3410, the program compares the patient's symptom magnitude pattern to its database of symptom magnitude patterns, to (attempt to) identify the patient's disease. Process 3400 ends at state 3412.

Figure 35:
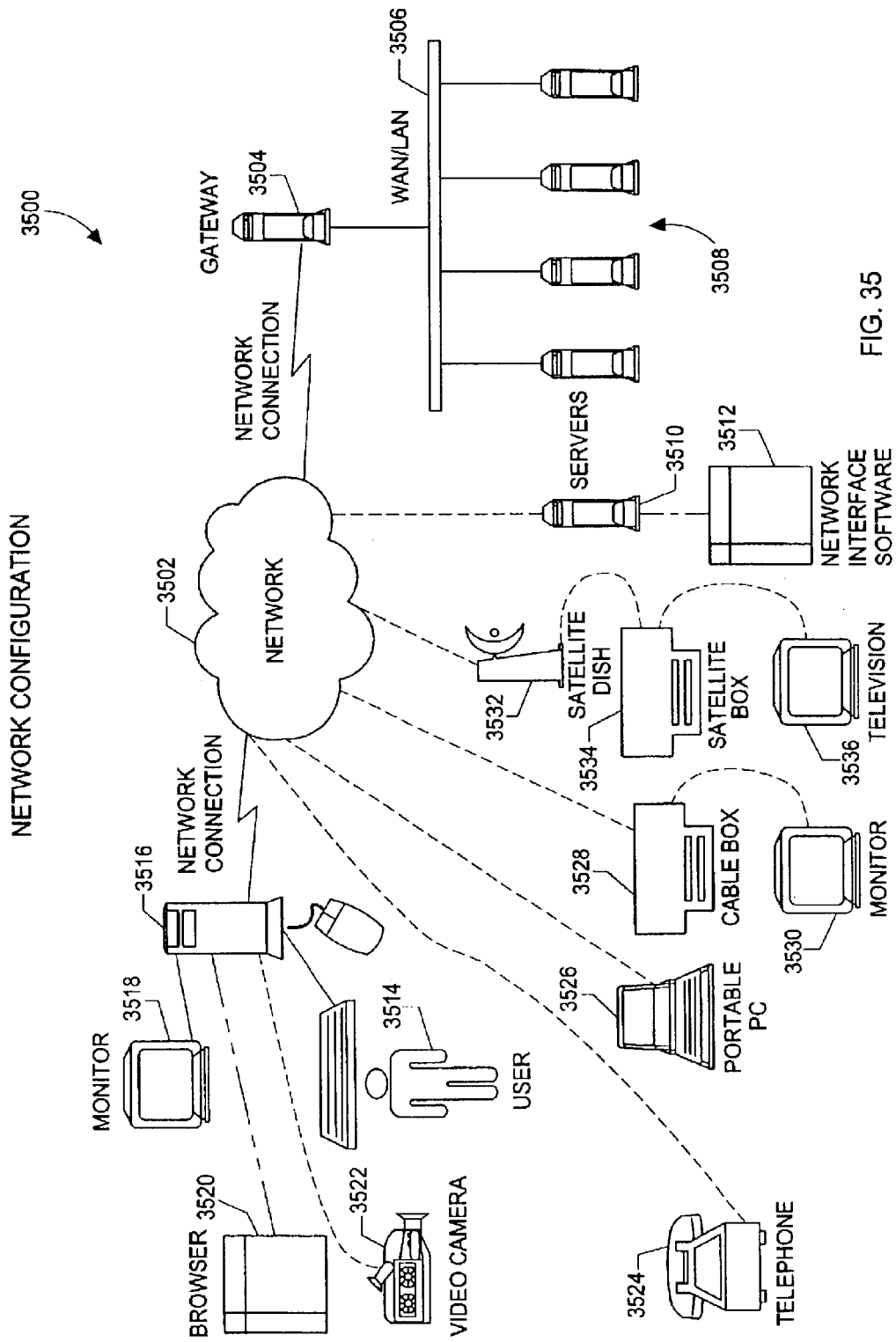
FIG. 35 is a block diagram illustrating components of one embodiment of the computerized medical diagnostic and treatment advice (MDATA) system of the present invention.

Referring to FIG. 35, a block diagram of one embodiment of the MDATA system 3500 will be described. The MDATA system 3500 includes a network cloud 3502, which may represent a local area network (LAN), a wide area network (WAN), the Internet, or another network capable of handling data communication.

In one embodiment, the MDATA programs and databases may reside on a group of servers 3508 that may be interconnected by a LAN 3506 and a gateway 3504 to the network 3502. Alternatively, in another embodiment, the MDATA programs and databases reside on a single server 3510 that utilizes network interface hardware and software 3512. The MDATA servers 3508/3510 store the disease/symptom/question lists or objects described above.

The network 3502 may connect to a user computer 3516, for example, by use of a modem or by use of a network interface card. A user 3514 at computer 3516 may utilize a browser 3520 to remotely access the MDATA programs using a keyboard and/or pointing device and a visual display, such as monitor 3518. Alternatively, the browser 3520 is not utilized when the MDATA programs are executed in a local mode on computer 3516. A video camera 3522 may be optionally connected to the computer 3516 to provide visual input, such as visual symptoms.

Various other devices may be used to communicate with the MDATA servers 3508/3510. If the servers are equipped with voice recognition or DTMF hardware, the user can communicate with the MDATA program by use of a telephone 3524. A telecommunications embodiment, e.g., using a telephone, is described in Applicant's U.S. patent entitled "Computerized Medical Diagnostic and Treatment Advice System," U.S. Pat. No. 5,660,176, which is hereby incorporated by reference. Other connection devices for communicating with the MDATA servers 3508/3510 include a portable personal computer 3526 with a modem or wireless connection interface, a cable interface device 3528 connected to a visual display 3530, or a satellite dish 3532 connected to a satellite receiver 3534 and a television 3536. Other ways of allowing communication between the user 3514 and the automated diagnostic system 3508/3510 are envisioned.

VI. Conclusion

Specific blocks, sections, devices, functions and modules may have been set forth. However, a skilled technologist will realize that there are many ways to partition the system of the present invention, and that there are many parts, components, modules or functions that may be substituted for those listed above.

As should be appreciated by a skilled technologist, the processes that are undergone by the by the above described software may be arbitrarily redistributed to other modules, or combined together in a single module, or made available in a shareable dynamic link library. The software may be written in any programming language such as C, C++, BASIC, Pascal, Java, and FORTRAN and executed under a well-known operating system, such as variants of Windows, Macintosh, Unix, Linux, VxWorks, or other operating system. C, C++, BASIC, Pascal, Java, and FORTRAN are industry standard programming languages for which many commercial compilers can be used to create executable code.

While the above detailed description has shown, described, and pointed out the fundamental novel features of the invention as applied to various embodiments, it will be understood that various omissions and substitutions and changes in the form and details of the system illustrated may be made by those skilled in the art, without departing from the intent of the invention.

What is claimed is:

1. A method of automatically diagnosing a medical condition by use of a predicted timeline of symptoms, the method comprising:

accessing a plurality of timelines which are each representative of a typical pattern of a disease;

automatically asking one or more questions of a patient so as to elicit a chief complaint;

automatically receiving answers from the patient in response to the questions;

automatically identifying a disease corresponding to the chief complaint;

correlating the chief complaint to a timeline for the disease;

automatically asking one or more questions to elicit the onset time of a symptom on the timeline for the disease;

adding an incremental weight to a cumulative score for the disease if the symptom is established; and establishing the diagnosis when the cumulative score exceeds a predetermined threshold.

2. The method defined in claim 1, wherein the chief complaint includes a symptom and a severity for the symptom.

3. The method defined in claim 1, wherein each disease is associated with one timeline.

4. The method defined in claim 1, wherein the symptom includes one of a sign, laboratory test result, or interpretation of an imaging modality.

5. The method defined in claim 1, additionally comprising automatically asking one or more questions to elicit the offset time of the symptom on the timeline for the disease.

6. A method of automatically diagnosing a medical condition of a patient by use of a predicted timeline of symptoms, the method comprising:

generating a plurality of timelines which are each representative of a typical course of a disease via a characteristic pattern of symptom attributes over time; and automatically selecting a particular disease based on a pattern of symptom attributes associated with a patient being similar to the timeline associated with the particular disease.

7. The method defined in claim 6, wherein each disease is associated with one timeline.

8. The method defined in claim 6, additionally comprising automatically asking questions of the patient.

9. The method defined in claim 8, additionally comprising creating a timeline of symptom attributes indicative of the patient based on answers to the questions.

* * * * *